US012559528B2

(12) United States Patent
Yagi et al.

(10) Patent No.: US 12,559,528 B2
(45) Date of Patent: Feb. 24, 2026

(54) PPR PROTEIN CAUSING LESS AGGREGATION AND USE OF THE SAME

(71) Applicants: EditForce, Inc., Fukuoka (JP); KYUSHU UNIVERSITY, NATIONAL UNIVERSITY CORPORATION, Fukuoka (JP)

(72) Inventors: Yusuke Yagi, Fukuoka (JP); Takayoshi Imai, Fukuoka (JP); Takayuki Tamai, Fukuoka (JP); Takahiro Nakamura, Fukuoka (JP); Takamasa Teramoto, Fukuoka (JP)

(73) Assignees: EditForce, Inc., Fukuoka (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 1042 days.

(21) Appl. No.: 17/614,236

(22) PCT Filed: May 29, 2020

(86) PCT No.: PCT/JP2020/021473
§ 371 (c)(1),
(2) Date: Nov. 24, 2021

(87) PCT Pub. No.: WO2020/241877
PCT Pub. Date: Dec. 3, 2020

(65) Prior Publication Data

US 2022/0220166 A1     Jul. 14, 2022

(30) Foreign Application Priority Data

May 29, 2019     (JP) ................................. 2019-100553

(51) Int. Cl.
| | |
|---|---|
| *C07K 14/00* | (2006.01) |
| *C07K 7/06* | (2006.01) |
| *C07K 7/08* | (2006.01) |
| *C07K 14/46* | (2006.01) |
| *C07K 19/00* | (2006.01) |
| *C12N 5/10* | (2006.01) |
| *C12N 15/63* | (2006.01) |

(52) U.S. Cl.
CPC ................ *C07K 14/46* (2013.01); *C07K 7/06* (2013.01); *C07K 7/08* (2013.01); *C07K 19/00* (2013.01); *C12N 5/10* (2013.01); *C12N 15/63* (2013.01)

(58) Field of Classification Search
CPC ...... A61K 38/28; A61K 47/549; A61K 47/65; A61P 3/10; C07K 5/0215; C07K 14/62
See application file for complete search history.

(56) References Cited

U.S. PATENT DOCUMENTS

2014/0335521 A1     11/2014     Nakamura et al.

FOREIGN PATENT DOCUMENTS

| CN | 109563137 A | 4/2019 |
|---|---|---|
| EP | 2784157 A1 | 10/2014 |
| EP | 3020722 A1 | 5/2016 |
| EP | 3978513 A1 | 4/2022 |
| JP | 2006188507 A | 7/2006 |
| JP | 2019-100551 A | 6/2019 |
| WO | 2013/058404 A1 | 4/2013 |
| WO | 2014/175284 A1 | 10/2014 |
| WO | 2020/241876 A1 | 12/2020 |

OTHER PUBLICATIONS

Banks et al. Science. May 20, 2011; 332(6032): 960-963.*
Office Action dated Apr. 4, 2024, issued in counterpart RU application No. 2021139146, with English translation. (19 pages).
Office Action dated May 17, 2024, issued in counterpart AU application No. 2020283367. (3 pages).
Office Action dated May 30, 2024, issued in counterpart NZ application No. 783357. (4 pages).
Office Action dated May 30, 2024, issued in counterpart CN application No. 202080040065.2, with English translation. (18 pages).
Office Action dated Sep. 3, 2024, issued in counterpart RU application No. 2021139146, with English translation. (12 pages).
Nakamura, T. et al., "Mechanistic Insight into Pentatricopeptide Repeat Proteins as Sequence-Specific RNA-Binding Proteins for Organellar RNAs in Plants", Plant Cell Physiol, 2012, vol. 53, No. 7, pp. 1171-1179. (9 pages).
Extended European Search Report dated Jun. 1, 2023 issued in the corresponding European patent application No. 20812826.4 (11 pages).
Ban, Ting et al., "Structure of a PLS-class Pentatricopeptide Repeat Protein Provides Insight into Mechanism of RNA Recognition", Journal of Biological Chemistry, vol. 288, No. 44, 2013; Cited in Extended European Search Report dated Jun. 1, 2023. (10 pages).
Kobayashi, K. et al., "Identification and characterization of the RNA biding surface of the pentatricopeptide repeat protein", Nucleic Acids Research, vol. 40, No. 6; 2012; Cited in Extended European Search Report dated Jun. 1, 2023. (12 pages).
Yagi, Yusuke et al., "Elucidation of the RNA Recognition Code for Pentatricopeptide Repeat Proteins Involved in Organlle RNA Editing in Plants", PLOS ONE, vol. 8, No. 3, 2013; Cited in Extended European Search Report dated Jun. 1, 2023. (8 pages).

(Continued)

*Primary Examiner* — Jeanette M Lieb
(74) *Attorney, Agent, or Firm* — WHDA, LLP

(57) ABSTRACT

In order to improve aggregation property of a PPR protein, the $A_6$ amino acid of the 1st PPR motif from the N-terminus $(M_1)$ is made more hydrophilic. Further, the $A_9$ amino acid of $M_1$ is made to be a hydrophilic amino acid or glycine. The $A_6$ amino acid is preferably asparagine or aspartic acid, and the $A_9$ amino acid is preferably glutamine, glutamic acid, lysine, or glycine. Proteins containing such a PPR motif as $M_1$ motif may have not only improved aggregation property, but also high binding power to a target nucleic acid.

6 Claims, 4 Drawing Sheets

Specification includes a Sequence Listing.

(56) References Cited

OTHER PUBLICATIONS

Yagi, Yusuke et al., "Construction of a Versatile, Programmable RNA-Binding Protein Using Designer of PPR Proteins and Its Application for Splicing Control Mammalian Cells", Cells, vol. 11, No. 22, 2022; Cited in Extended European Search Report dated Jun. 1, 2023. (17 pages).

Office Action dated Jun. 14, 2022, issued in counterpart JP application No. 2021-521908, with English translation. (6 pages).

Fujiwara et al., "Selection of inhibitory peptides for Aurora-A kinase from phage-displayed library of helix-loop-helix peptides", Bioorganic & Medicinal Chemistry Letters, 2010, vol. 20, pp. 1776-1778, cited in JP Office Action dated Jun. 14, 2022. (3 pages).

Fukui et al., "A metabonomic approach identifies human urinary phenylacetylglutamine as a novel marker of Interstitial cystitis", Journal of Chromatography B, 2009, vol. 877, No. 30, pp. 3806-3812, cited in JP Office Action dated Jun. 14, 2022. (7 pages).

Coquille, S. et al., "An artificial PPR scaffold for programmable RNA recognition", Nature Communications, 2014, vol. 5, Article No. 6729, pp. 1-9, cited in specification. (9 pages).

Shen, C. et al., "Specific RNA Recognition by Designer Pentatricopeptide Repeat Protein", Molecular Plant, 2015, vol. 3, pp. 667-670, cited in specification. (4 pages).

Shen, C. et al., "Structural basis for specific single-stranded RNA recognition by designer pentatricopeptide repeat proteins", Nature Communications, 2016, vol. 7, Article No. 11285, pp. 1-8, cited in specification. (8 pages).

Miranda, R.G. et al., "RNA-binding specificity landscapes of designer pentatricopeptide repeat proteins elucidate principles of PPR-RNA interactions", Nucleic Acids Research, 2018, vol. 46, No. 5, pp. 2613-2623, cited in specification. (11 pages).

Yan, J. et al., "Delineation of pentatricopeptide repeat codes for target RNA prediction", Nucleic Acids Research, 2019, pp. 1-11, cited in specification. (11 pages).

Yagi, Yusuke, "The development of endogenous RNA imaging technique", Oct. 27, 2016, cited in IPRP dated Nov. 16, 2021. (5 pages).

Takaoka, Yuji, "Predicting aggregation propensity of proteins by DS Protein Aggregation (AggMap)", Molecular Science, 2012, vol. 6, NP0016, pp. 1-2, cited in IPRP dated Nov. 16, 2021. (2 pages).

Mosavi, Leila K. et al., "Structure-based substitutions for increased solubility of a designed protein", Protein Engineering, 2003, vol. 16, No. 10, pp. 739-745, cited in IPRP dated Nov. 16, 2021. (7 pages).

International Preliminary Report on Patentability (Form PCT/IB/373) issued in counterpart International application No. PCT/JP2020/021473 mailed Nov. 16, 2021 with Form PCT/ISA/237, with English translation. (9 pages).

Decision of Rejection dated Oct. 21, 2024, issued in counterpart KR Application No. 10-2021-7040376, with English translation. (14 pages).

Office Action dated Oct. 21, 2024, issued in counterpart AU Application No. 2020283367. (3 pages).

Office Action dated Nov. 22, 2023 issued in counterpart KR application No. 10-2021-7040376 with its English Translation. (22 pages).

Office Action dated Jan. 10, 2024 issued in counterpart SG application No. 11202113057X. (13 pages).

Office Action dated Jan. 19, 2024 issued in counterpart SG application No. 11202113057X. (13 pages).

Office Action dated Mar. 20, 2025, issued in counterpart BR application No. BR1120210239375, with English translation. (17 pages).

* cited by examiner

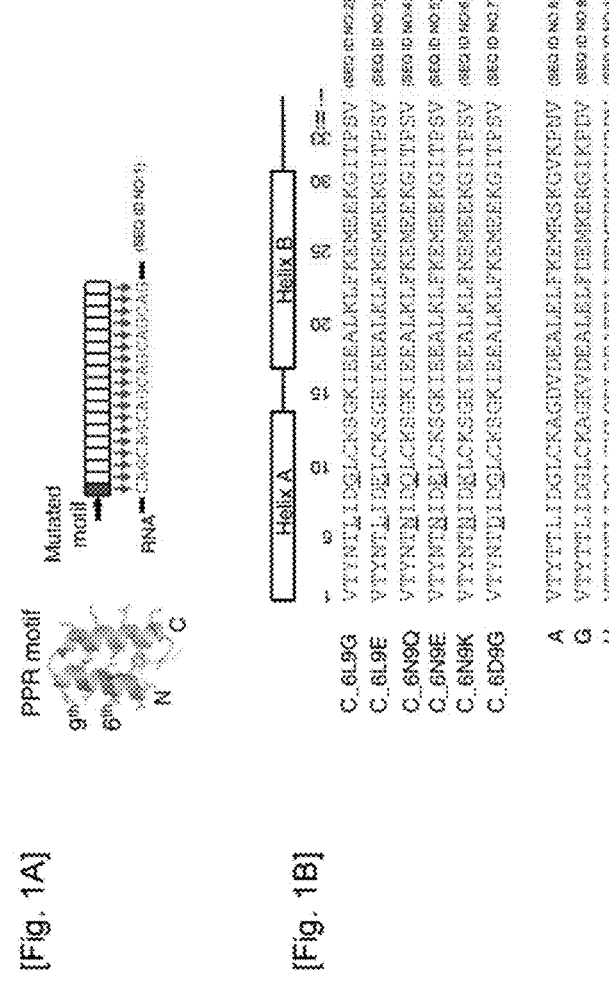
[Fig. 1A]
[Fig. 1B]

[Fig. 2]
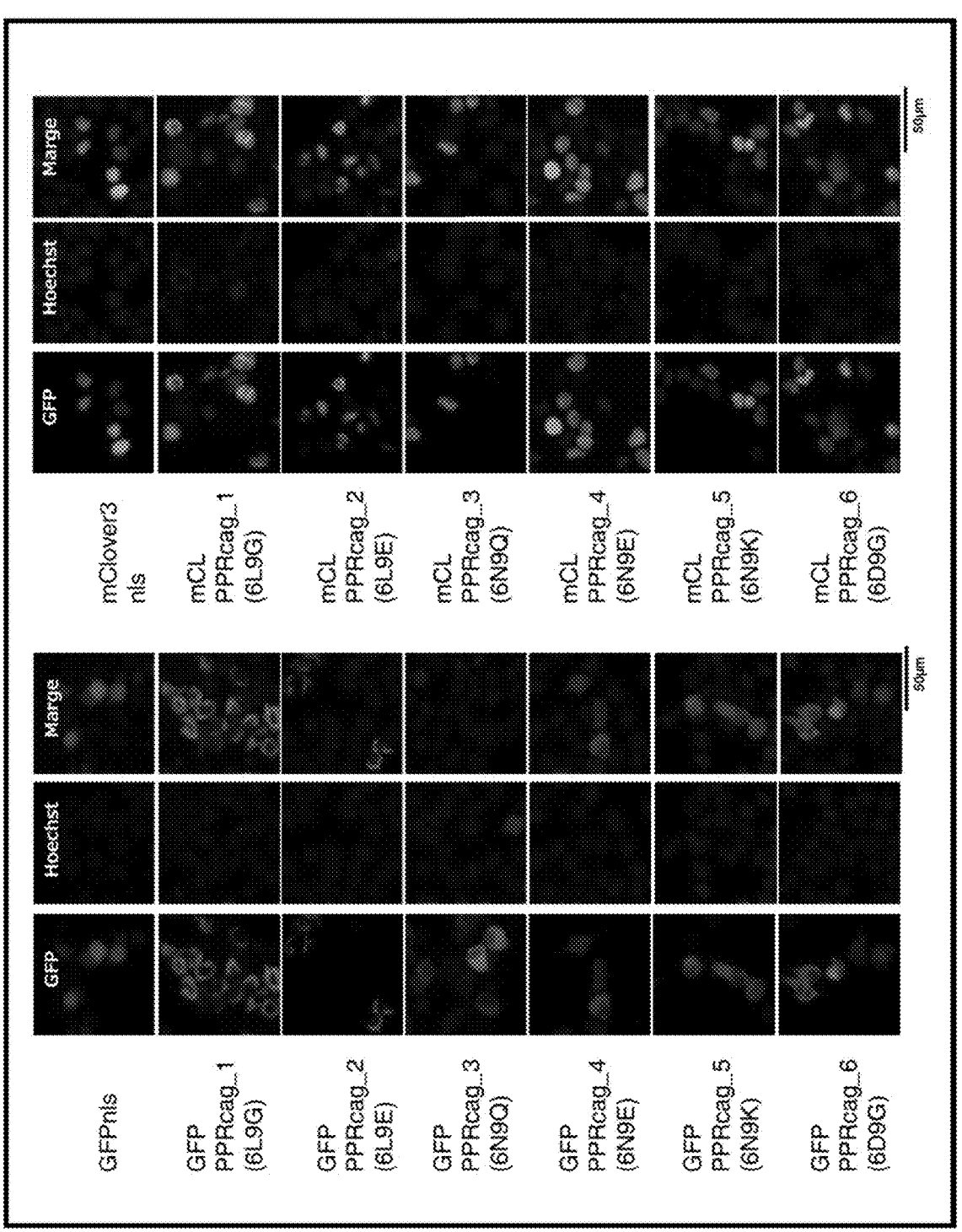

[Fig. 3]

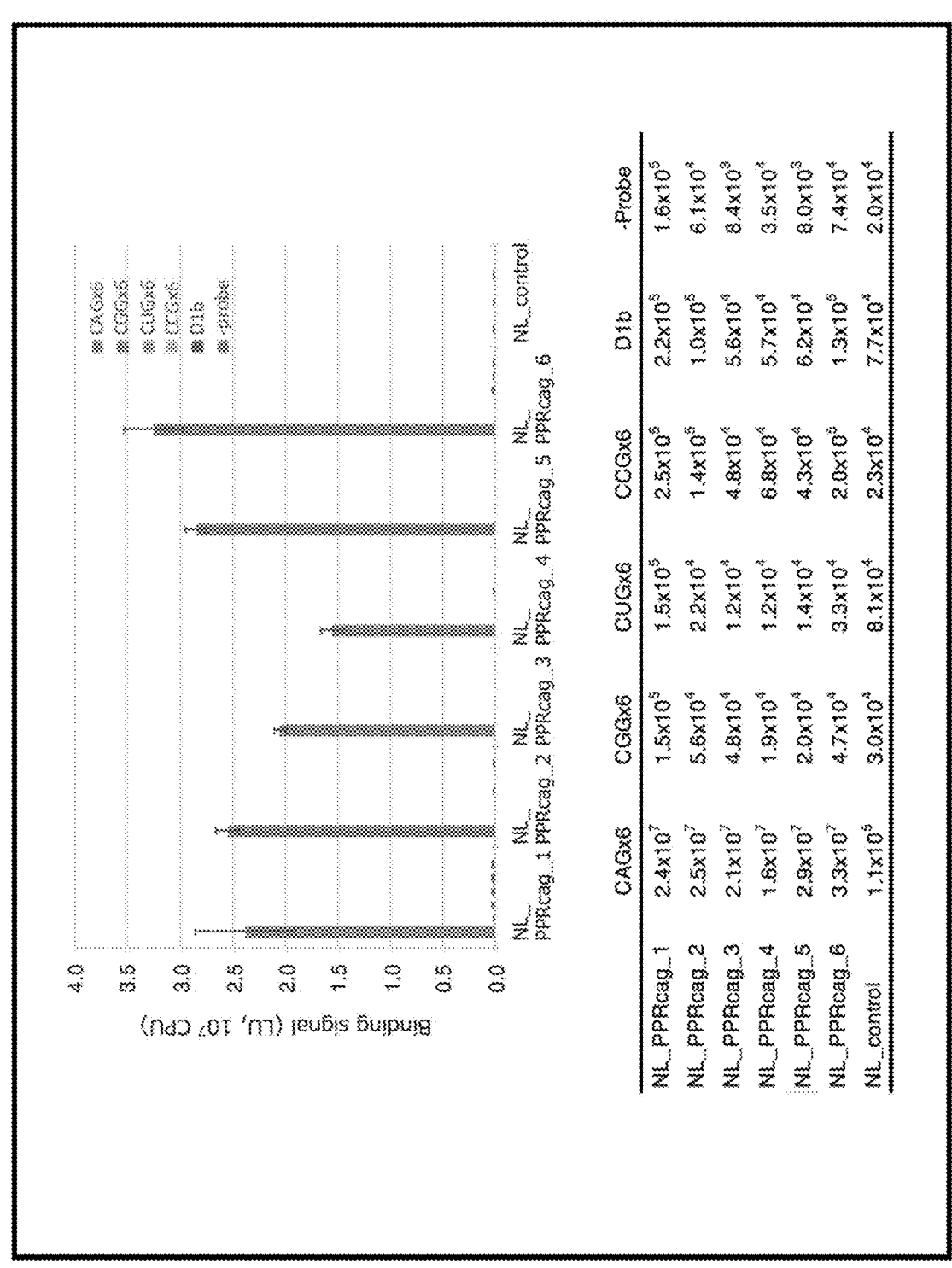

| | CAGx6 | CGGx6 | CUGx6 | CCGx6 | D1b | -Probe |
|---|---|---|---|---|---|---|
| NL_PPRcag_1 | $2.4 \times 10^7$ | $1.5 \times 10^5$ | $1.5 \times 10^5$ | $2.5 \times 10^5$ | $2.2 \times 10^5$ | $1.6 \times 10^5$ |
| NL_PPRcag_2 | $2.5 \times 10^7$ | $5.6 \times 10^4$ | $2.2 \times 10^4$ | $1.4 \times 10^5$ | $1.0 \times 10^5$ | $6.1 \times 10^4$ |
| NL_PPRcag_3 | $2.1 \times 10^7$ | $4.8 \times 10^4$ | $1.2 \times 10^4$ | $4.8 \times 10^4$ | $5.6 \times 10^4$ | $8.4 \times 10^3$ |
| NL_PPRcag_4 | $1.6 \times 10^7$ | $1.9 \times 10^4$ | $1.2 \times 10^4$ | $6.8 \times 10^4$ | $5.7 \times 10^4$ | $3.5 \times 10^4$ |
| NL_PPRcag_5 | $2.9 \times 10^7$ | $2.0 \times 10^4$ | $1.4 \times 10^4$ | $4.3 \times 10^4$ | $6.2 \times 10^4$ | $8.0 \times 10^3$ |
| NL_PPRcag_6 | $3.3 \times 10^7$ | $4.7 \times 10^4$ | $3.3 \times 10^4$ | $2.0 \times 10^5$ | $1.3 \times 10^5$ | $7.4 \times 10^4$ |
| NL_control | $1.1 \times 10^5$ | $3.0 \times 10^4$ | $8.1 \times 10^4$ | $2.3 \times 10^4$ | $7.7 \times 10^4$ | $2.0 \times 10^4$ |

[Fig. 4]
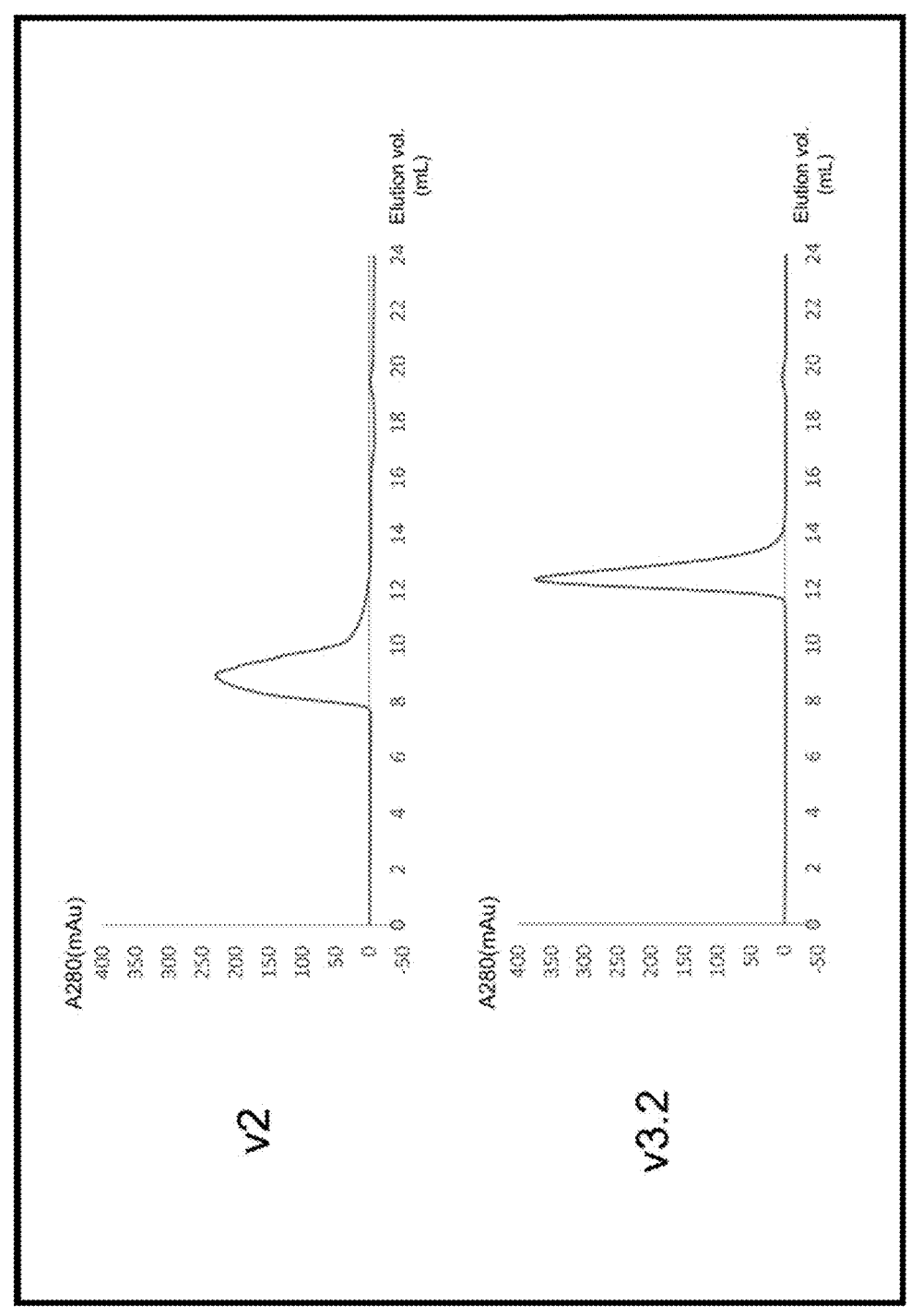

SEQUENCE LISTING

```
<160> NUMBER OF SEQ ID NOS: 64

<210> SEQ ID NO 1
<211> LENGTH: 18
<212> TYPE: DNA
<213> ORGANISM: Artificial sequence
<220> FEATURE:
<223> OTHER INFORMATION: target sequence

<400> SEQUENCE: 1
cagcagcagc agcagcag                                                    18

<210> SEQ ID NO 2
<211> LENGTH: 35
<212> TYPE: PRT
<213> ORGANISM: Artificial sequence
<220> FEATURE:
<223> OTHER INFORMATION: PPR motif

<400> SEQUENCE: 2

Val Thr Tyr Asn Thr Leu Ile Asp Gly Leu Cys Lys Ser Gly Lys Ile
1               5                   10                  15

Glu Glu Ala Leu Lys Leu Phe Lys Glu Met Glu Glu Lys Gly Ile Thr
            20                  25                  30

Pro Ser Val
        35

<210> SEQ ID NO 3
<211> LENGTH: 35
<212> TYPE: PRT
<213> ORGANISM: Artificial sequence
```

<220> FEATURE:
<223> OTHER INFORMATION: PPR motif

<400> SEQUENCE: 3

Val Thr Tyr Asn Thr Leu Ile Asp Glu Leu Cys Lys Ser Gly Lys Ile
1               5                   10                  15

Glu Glu Ala Leu Lys Leu Phe Lys Glu Met Glu Glu Lys Gly Ile Thr
            20                  25                  30

Pro Ser Val
        35

<210> SEQ ID NO 4
<211> LENGTH: 35
<212> TYPE: PRT
<213> ORGANISM: Artificial sequence
<220> FEATURE:
<223> OTHER INFORMATION: PPR motif, 1st_U (v3.2_U)

<400> SEQUENCE: 4

Val Thr Tyr Asn Thr Asn Ile Asp Gln Leu Cys Lys Ser Gly Lys Ile
1               5                   10                  15

Glu Glu Ala Leu Lys Leu Phe Lys Glu Met Glu Glu Lys Gly Ile Thr
            20                  25                  30

Pro Ser Val
        35

<210> SEQ ID NO 5
<211> LENGTH: 35
<212> TYPE: PRT
<213> ORGANISM: Artificial sequence
<220> FEATURE:
<223> OTHER INFORMATION: PPR motif

<400> SEQUENCE: 5

Val Thr Tyr Asn Thr Asn Ile Asp Glu Leu Cys Lys Ser Gly Lys Ile
1               5                   10                  15

Glu Glu Ala Leu Lys Leu Phe Lys Glu Met Glu Glu Lys Gly Ile Thr
            20                  25                  30

Pro Ser Val
        35

<210> SEQ ID NO 6
<211> LENGTH: 35
<212> TYPE: PRT
<213> ORGANISM: Artificial sequence
<220> FEATURE:
<223> OTHER INFORMATION: PPR motif

<400> SEQUENCE: 6

Val Thr Tyr Asn Thr Asn Ile Asp Lys Leu Cys Lys Ser Gly Lys Ile
1               5                   10                  15

Glu Glu Ala Leu Lys Leu Phe Lys Glu Met Glu Glu Lys Gly Ile Thr
            20                  25                  30

Pro Ser Val
        35

<210> SEQ ID NO 7
<211> LENGTH: 35
<212> TYPE: PRT
<213> ORGANISM: Artificial sequence
<220> FEATURE:
<223> OTHER INFORMATION: PPR motif -continued

```
<400> SEQUENCE: 7

Val Thr Tyr Asn Thr Asp Ile Asp Gly Leu Cys Lys Ser Gly Lys Ile
1               5                   10                  15

Glu Glu Ala Leu Lys Leu Phe Lys Glu Met Glu Glu Lys Gly Ile Thr
            20                  25                  30

Pro Ser Val
        35

<210> SEQ ID NO 8
<211> LENGTH: 35
<212> TYPE: PRT
<213> ORGANISM: Artificial sequence
<220> FEATURE:
<223> OTHER INFORMATION: PPR motif

<400> SEQUENCE: 8

Val Thr Tyr Thr Thr Leu Ile Asp Gly Leu Cys Lys Ala Gly Asp Val
1               5                   10                  15

Asp Glu Ala Leu Glu Leu Phe Lys Glu Met Arg Ser Lys Gly Val Lys
            20                  25                  30

Pro Asn Val
        35

<210> SEQ ID NO 9
<211> LENGTH: 35
<212> TYPE: PRT
<213> ORGANISM: Artificial sequence
<220> FEATURE:
<223> OTHER INFORMATION: PPR motif

<400> SEQUENCE: 9

Val Thr Tyr Thr Thr Leu Ile Asp Gly Leu Cys Lys Ala Gly Lys Val
1               5                   10                  15

Asp Glu Ala Leu Glu Leu Phe Asp Glu Met Lys Glu Arg Gly Ile Lys
            20                  25                  30

Pro Asp Val
        35

<210> SEQ ID NO 10
<211> LENGTH: 35
<212> TYPE: PRT
<213> ORGANISM: Artificial sequence
<220> FEATURE:
<223> OTHER INFORMATION: PPR motif

<400> SEQUENCE: 10

Val Thr Tyr Asn Thr Leu Ile Asp Gly Leu Cys Lys Ala Gly Arg Leu
1               5                   10                  15

Asp Glu Ala Glu Glu Leu Leu Glu Glu Met Glu Glu Lys Gly Ile Lys
            20                  25                  30

Pro Asp Val
        35

<210> SEQ ID NO 11
<211> LENGTH: 2303
<212> TYPE: DNA
<213> ORGANISM: Artificial sequence
<220> FEATURE:
<223> OTHER INFORMATION: PPR gene
<220> FEATURE:
<221> NAME/KEY: misc_feature
<222> LOCATION: (1894)..(1894)
<223> OTHER INFORMATION: n is a, c, g, t or u
```

-continued

```
<220> FEATURE:
<221> NAME/KEY: misc_feature
<222> LOCATION: (1935)..(1935)
<223> OTHER INFORMATION: n is a, c, g, t or u
<220> FEATURE:
<221> NAME/KEY: misc_feature
<222> LOCATION: (1963)..(1963)
<223> OTHER INFORMATION: n is a, c, g, t or u
<220> FEATURE:
<221> NAME/KEY: misc_feature
<222> LOCATION: (2004)..(2004)
<223> OTHER INFORMATION: n is a, c, g, t or u
<220> FEATURE:
<221> NAME/KEY: misc_feature
<222> LOCATION: (2032)..(2032)
<223> OTHER INFORMATION: n is a, c, g, t or u
<220> FEATURE:
<221> NAME/KEY: misc_feature
<222> LOCATION: (2073)..(2073)
<223> OTHER INFORMATION: n is a, c, g, t or u
<220> FEATURE:
<221> NAME/KEY: misc_feature
<222> LOCATION: (2101)..(2101)
<223> OTHER INFORMATION: n is a, c, g, t or u
<220> FEATURE:
<221> NAME/KEY: misc_feature
<222> LOCATION: (2142)..(2142)
<223> OTHER INFORMATION: n is a, c, g, t or u
<220> FEATURE:
<221> NAME/KEY: misc_feature
<222> LOCATION: (2170)..(2170)
<223> OTHER INFORMATION: n is a, c, g, t or u
<220> FEATURE:
<221> NAME/KEY: misc_feature
<222> LOCATION: (2211)..(2211)
<223> OTHER INFORMATION: n is a, c, g, t or u
<220> FEATURE:
<221> NAME/KEY: misc_feature
<222> LOCATION: (2239)..(2239)
<223> OTHER INFORMATION: n is a, c, g, t or u
<220> FEATURE:
<221> NAME/KEY: misc_feature
<222> LOCATION: (2280)..(2280)
<223> OTHER INFORMATION: n is a, c, g, t or u

<400> SEQUENCE: 11
gtcacataca acaccctgat cgacggcctg tgcaagagcg gcaagatcga ggaggccctg      60
aagctgttca aggagatgga ggagaagggc atcaccccca gcgtggtcac atacaccaca     120
ctgatcgacg gactgtgtaa agccggcgac gtggacgaag ccctcgagct gttcaaagag     180
atgcggagca agggcgtgaa gcccaacgtg gtgcatataca ccaccctgat cgacggcctg     240
tgcaaggccg gcaaagtgga cgaggccctg gagctgttcg acgagatgaa ggagaggggc     300
atcaagcccg acgtggtcac atacaacacc ctgatcgacg gcctgtgcaa gagcggcaag     360
atcgaggagg ccctgaagct gttcaaggag atggaggaga agggcatcac ccccagcgtg     420
gttacataca ccacactgat cgacggactg tgtaaagccg gcgacgtgga cgaagccctc     480
gagctgttca aagagatgcg gagcaagggc gtgaagccca acgtggtcac atacaccacc     540
ctgatcgacg gcctgtgcaa ggccggcaag gtggatgagg ccctggagct gttcgacgag     600
atgaaggaga ggggcatcaa gcccgacgtg gttacataca acaccctgat cgacggcctg     660
tgcaagagcg gcaagatcga ggaggccctg aagctgttca aggagatgga ggagaagggc     720
atcaccccca gcgtggtcac atacaccaca ctgatcgacg gactgtgtaa agccggcgac     780
gtggacgaag ccctcgagct gttcaaagag atgcggagca agggcgtgaa gcccaacgtg     840
gtgacataca ccaccctgat cgacggcctg tgcaaggccg gcaaagtgga cgaggccctg     900
gagctgttcg acgagatgaa ggagaggggc atcaagcccg acgtggtcac atacaacacc     960
```

-continued

```
ctgatcgacg gcctgtgcaa gagcggcaag atcgaggagg ccctgaagct gttcaaggag        1020
atggaggaga agggcatcac ccccagcgtg gttacataca ccacactgat cgacggactg        1080
tgtaaagccg gcgacgtgga cgaagccctc gagctgttca aagagatgcg gagcaagggc        1140
gtgaagccca acgtggtcac atacaccacc ctgatcgacg gcctgtgcaa ggccggcaag        1200
gtggatgagg ccctggagct gttcgacgag atgaaggaga ggggcatcaa gcccgacgtg        1260
gtcacataca acaccctgat cgacggcctg tgcaagagcg gcaagatcga ggaggccctg        1320
aagctgttca aggagatgga ggagaagggc atcaccccca gcgtggtcac atacaccaca        1380
ctgatcgacg gactgtgtaa agccggcgac gtggacgaag ccctcgagct gttcaaagag        1440
atgcggagca agggcgtgaa gcccaacgtg gttacataca ccaccctgat cgacggcctg        1500
tgcaaggccg gcaaagtgga cgaggccctg gagctgttcg acgagatgaa ggagaggggc        1560
atcaagcccg acgtggtcac atacaacacc ctgatcgacg gcctgtgcaa gagcggcaag        1620
atcgaggagg ccctgaagct gttcaaggag atggaggaga agggcatcac ccccagcgtg        1680
gtgacataca ccacactgat cgacggactg tgtaaagccg gcgacgtgga cgaagccctc        1740
gagctgttca aagagatgcg gagcaagggc gtgaagccca acgtggtcac atacaccacc        1800
ctgatcgacg gcctgtgcaa ggccggcaag gtggatgagg ccctggagct gttcgacgag        1860
atgaaggaga ggggcatcaa gcccgacgag vtyntdgcks gkakkmkgts vvtyttdgck        1920
agdvdakmrs kgvknvvtyt tdgckagkvd admkrgkdvv tyntdgcksg kakkmkgtsv        1980
vtyttdgcka gdvdakmrsk gvknvvtytt dgckagkvda dmkrgkdvvt yntdgcksgk        2040
akkmkgtsvv tyttdgckag dvdakmrskg vknvvtyttd gckagkvdad mkrgkdvvty        2100
ntdgcksgka kkmkgtsvvt yttdgckagd vdakmrskgv knvvtyttdg ckagkvdadm        2160
krgkdvvtyn tdgcksgkak kmkgtsvvty ttdgckagdv dakmrskgvk nvvtyttdgc        2220
kagkvdadmk rgkdvvtynt dgcksgkakk mkgtsvvtyt tdgckagdvd akmrskgvkn        2280
vvtyttdgck agkvdadmkr gkd                                                 2303
```

```
<210> SEQ ID NO 12
<211> LENGTH: 2302
<212> TYPE: DNA
<213> ORGANISM: Artificial sequence
<220> FEATURE:
<223> OTHER INFORMATION: PPR gene
<220> FEATURE:
<221> NAME/KEY: misc_feature
<222> LOCATION: (1894)..(1894)
<223> OTHER INFORMATION: n is a, c, g, t or u
<220> FEATURE:
<221> NAME/KEY: misc_feature
<222> LOCATION: (1934)..(1934)
<223> OTHER INFORMATION: n is a, c, g, t or u
<220> FEATURE:
<221> NAME/KEY: misc_feature
<222> LOCATION: (1962)..(1962)
<223> OTHER INFORMATION: n is a, c, g, t or u
<220> FEATURE:
<221> NAME/KEY: misc_feature
<222> LOCATION: (2003)..(2003)
<223> OTHER INFORMATION: n is a, c, g, t or u
<220> FEATURE:
<221> NAME/KEY: misc_feature
<222> LOCATION: (2031)..(2031)
<223> OTHER INFORMATION: n is a, c, g, t or u
<220> FEATURE:
<221> NAME/KEY: misc_feature
<222> LOCATION: (2072)..(2072)
<223> OTHER INFORMATION: n is a, c, g, t or u
<220> FEATURE:
<221> NAME/KEY: misc_feature
```

```
<222> LOCATION: (2100)..(2100)
<223> OTHER INFORMATION: n is a, c, g, t or u
<220> FEATURE:
<221> NAME/KEY: misc_feature
<222> LOCATION: (2141)..(2141)
<223> OTHER INFORMATION: n is a, c, g, t or u
<220> FEATURE:
<221> NAME/KEY: misc_feature
<222> LOCATION: (2169)..(2169)
<223> OTHER INFORMATION: n is a, c, g, t or u
<220> FEATURE:
<221> NAME/KEY: misc_feature
<222> LOCATION: (2210)..(2210)
<223> OTHER INFORMATION: n is a, c, g, t or u
<220> FEATURE:
<221> NAME/KEY: misc_feature
<222> LOCATION: (2238)..(2238)
<223> OTHER INFORMATION: n is a, c, g, t or u
<220> FEATURE:
<221> NAME/KEY: misc_feature
<222> LOCATION: (2279)..(2279)
<223> OTHER INFORMATION: n is a, c, g, t or u

<400> SEQUENCE: 12
gtcacataca acaccctgat cgacgaactg tgcaagagcg gcaagatcga ggaggccctg      60
aagctgttca aggagatgga ggagaagggc atcacccccca gcgtggtcac atacaccaca     120
ctgatcgacg gactgtgtaa agccggcgac gtggacgaag ccctcgagct gttcaaagag     180
atgcggagca agggcgtgaa gcccaacgtg gtgacataca ccaccctgat cgacggcctg     240
tgcaaggccg gcaaagtgga cgaggccctg gagctgttcg acgagatgaa ggagaggggc     300
atcaagcccg acgtggtcac atacaacacc ctgatcgacg gcctgtgcaa gagcggcaag     360
atcgaggagg ccctgaagct gttcaaggag atggaggaga agggcatcac ccccagcgtg     420
gttacataca ccacactgat cgacggactg tgtaaagccg gcgacgtgga cgaagccctc     480
gagctgttca aagagatgcg gagcaagggc gtgaagccca acgtggtcac atacaccacc     540
ctgatcgacg gcctgtgcaa ggccggcaag gtggatgagg ccctggagct gttcgacgag     600
atgaaggaga ggggcatcaa gcccgacgtg gttacataca acaccctgat cgacggcctg     660
tgcaagagcg gcaagatcga ggaggccctg aagctgttca aggagatgga ggagaagggc     720 atcacccccca gcgtggtcac atacaccaca ctgatcgacg gactgtgtaa agccggcgac     780
gtggacgaag ccctcgagct gttcaaagag atgcggagca agggcgtgaa gcccaacgtg     840
gtgacataca ccaccctgat cgacggcctg tgcaaggccg gcaaagtgga cgaggccctg     900
gagctgttcg acgagatgaa ggagaggggc atcaagcccg acgtggtcac atacaacacc     960
ctgatcgacg gcctgtgcaa gagcggcaag atcgaggagg ccctgaagct gttcaaggag    1020
atggaggaga agggcatcac ccccagcgtg gttacataca ccacactgat cgacggactg    1080
tgtaaagccg gcgacgtgga cgaagccctc gagctgttca aagagatgcg gagcaagggc    1140
gtgaagccca acgtggtcac atacaccacc ctgatcgacg gcctgtgcaa ggccggcaag    1200
gtggatgagg ccctggagct gttcgacgag atgaaggaga ggggcatcaa gcccgacgtg    1260
gtcacataca acaccctgat cgacggcctg tgcaagagcg gcaagatcga ggaggccctg    1320
aagctgttca aggagatgga ggagaagggc atcacccccca gcgtggtcac atacaccaca    1380
ctgatcgacg gactgtgtaa agccggcgac gtggacgaag ccctcgagct gttcaaagag    1440
atgcggagca agggcgtgaa gcccaacgtg gttacataca ccaccctgat cgacggcctg    1500
tgcaaggccg gcaaagtgga cgaggccctg gagctgttcg acgagatgaa ggagaggggc    1560
atcaagcccg acgtggtcac atacaacacc ctgatcgacg gcctgtgcaa gagcggcaag    1620
```

```
atcgaggagg ccctgaagct gttcaaggag atggaggaga agggcatcac ccccagcgtg      1680
gtgacataca ccacactgat cgacggactg tgtaaagccg gcgacgtgga cgaagccctc      1740
gagctgttca aagagatgcg gagcaagggc gtgaagccca acgtggtcac atacaccacc      1800
ctgatcgacg gcctgtgcaa ggccggcaag gtggatgagg ccctggagct gttcgacgag      1860
atgaaggaga ggggcatcaa gcccgacgag vtyntdcksg kakkmkgtsv vtyttdgcka      1920
gdvdakmrsk gvknvvtytt dgckagkvda dmkrgkdvvt yntdgcksgk akkmkgtsvv      1980
tyttdgckag dvdakmrskg vknvvtyttd gckagkvdad mkrgkdvvty ntdgcksgka      2040
kkmkgtsvvt yttdgckagd vdakmrskgv knvvtyttdg ckagkvdadm krgkdvvtyn      2100
tdgcksgkak kmkgtsvvty ttdgckagdv dakmrskgvk nvvtyttdgc kagkvdadmk      2160
rgkdvvtynt dgcksgkakk mkgtsvvtyt tdgckagdvd akmrskgvkn vvtyttdgck      2220
agkvdadmkr gkdvvtyntd gcksgkakkm kgtsvvtytt dgckagdvda kmrskgvknv      2280
vtyttdgcka gkvdadmkrg kd                                              2302
```

```
<210> SEQ ID NO 13
<211> LENGTH: 2303
<212> TYPE: DNA
<213> ORGANISM: Artificial sequence
<220> FEATURE:
<223> OTHER INFORMATION: PPR gene
<220> FEATURE:
<221> NAME/KEY: misc_feature
<222> LOCATION: (1894)..(1894)
<223> OTHER INFORMATION: n is a, c, g, t or u
<220> FEATURE:
<221> NAME/KEY: misc_feature
<222> LOCATION: (1896)..(1896)
<223> OTHER INFORMATION: n is a, c, g, t or u
<220> FEATURE:
<221> NAME/KEY: misc_feature
<222> LOCATION: (1935)..(1935)
<223> OTHER INFORMATION: n is a, c, g, t or u
<220> FEATURE:
<221> NAME/KEY: misc_feature
<222> LOCATION: (1963)..(1963)
<223> OTHER INFORMATION: n is a, c, g, t or u
<220> FEATURE:
<221> NAME/KEY: misc_feature
<222> LOCATION: (2004)..(2004)
<223> OTHER INFORMATION: n is a, c, g, t or u
<220> FEATURE:
<221> NAME/KEY: misc_feature
<222> LOCATION: (2032)..(2032)
<223> OTHER INFORMATION: n is a, c, g, t or u
<220> FEATURE:
<221> NAME/KEY: misc_feature
<222> LOCATION: (2073)..(2073)
<223> OTHER INFORMATION: n is a, c, g, t or u
<220> FEATURE:
<221> NAME/KEY: misc_feature
<222> LOCATION: (2101)..(2101)
<223> OTHER INFORMATION: n is a, c, g, t or u
<220> FEATURE:
<221> NAME/KEY: misc_feature
<222> LOCATION: (2142)..(2142)
<223> OTHER INFORMATION: n is a, c, g, t or u
<220> FEATURE:
<221> NAME/KEY: misc_feature
<222> LOCATION: (2170)..(2170)
<223> OTHER INFORMATION: n is a, c, g, t or u
<220> FEATURE:
<221> NAME/KEY: misc_feature
<222> LOCATION: (2211)..(2211)
<223> OTHER INFORMATION: n is a, c, g, t or u
<220> FEATURE:
<221> NAME/KEY: misc_feature
<222> LOCATION: (2239)..(2239)
<223> OTHER INFORMATION: n is a, c, g, t or u
```

-continued

```
<220> FEATURE:
<221> NAME/KEY: misc_feature
<222> LOCATION: (2280)..(2280)
<223> OTHER INFORMATION: n is a, c, g, t or u

<400> SEQUENCE: 13
gtcacataca acaccaacat cgaccagctg tgcaagagcg gcaagatcga ggaggccctg      60
aagctgttca aggagatgga ggagaagggc atcaccccca gcgtggtcac atacaccaca     120
ctgatcgacg gactgtgtaa agccggcgac gtggacgaag ccctcgagct gttcaaagag     180
atgcggagca agggcgtgaa gcccaacgtg gtgacataca ccaccctgat cgacggcctg     240
tgcaaggccg gcaaagtgga cgaggccctg gagctgttcg acgagatgaa ggagaggggc     300
atcaagcccg acgtggtcac atacaacacc ctgatcgacg gcctgtgcaa gagcggcaag     360
atcgaggagg ccctgaagct gttcaaggag atggaggaga agggcatcac ccccagcgtg     420
gttacataca ccacactgat cgacggactg tgtaaagccg gcgacgtgga cgaagccctc     480
gagctgttca aagagatgcg gagcaagggc gtgaagccca cgtggtcac atacaccacc     540 ctgatcgacg gcctgtgcaa ggccggcaag gtggatgagg ccctggagct gttcgacgag     600
atgaaggaga ggggcatcaa gcccgacgtg gttacataca acaccctgat cgacggcctg     660
tgcaagagcg gcaagatcga ggaggccctg aagctgttca aggagatgga ggagaagggc     720
atcaccccca gcgtggtcac atacaccaca ctgatcgacg gactgtgtaa agccggcgac     780
gtggacgaag ccctcgagct gttcaaagag atgcggagca agggcgtgaa gcccaacgtg     840
gtgacataca ccaccctgat cgacggcctg tgcaaggccg gcaaagtgga cgaggccctg     900
gagctgttcg acgagatgaa ggagaggggc atcaagcccg acgtggtcac atacaacacc     960
ctgatcgacg gcctgtgcaa gagcggcaag atcgaggagg ccctgaagct gttcaaggag    1020
atggaggaga agggcatcac ccccagcgtg gttacataca ccacactgat cgacggactg    1080
tgtaaagccg gcgacgtgga cgaagccctc gagctgttca aagagatgcg gagcaagggc    1140
gtgaagccca cgtggtcac atacaccacc ctgatcgacg gcctgtgcaa ggccggcaag    1200
gtggatgagg ccctggagct gttcgacgag atgaaggaga ggggcatcaa gcccgacgtg    1260
gtcacataca cacccctgat cgacggcctg tgcaagagcg gcaagatcga ggaggccctg    1320
aagctgttca aggagatgga ggagaagggc atcaccccca gcgtggtcac atacaccaca    1380
ctgatcgacg gactgtgtaa agccggcgac gtggacgaag ccctcgagct gttcaaagag    1440
atgcggagca agggcgtgaa gcccaacgtg gttacataca ccaccctgat cgacggcctg    1500
tgcaaggccg gcaaagtgga cgaggccctg gagctgttcg acgagatgaa ggagaggggc    1560
atcaagcccg acgtggtcac atacaacacc ctgatcgacg gcctgtgcaa gagcggcaag    1620
atcgaggagg ccctgaagct gttcaaggag atggaggaga agggcatcac ccccagcgtg    1680
gtgacataca ccacactgat cgacggactg tgtaaagccg gcgacgtgga cgaagccctc    1740
gagctgttca aagagatgcg gagcaagggc gtgaagccca cgtggtcac atacaccacc    1800 ctgatcgacg gcctgtgcaa ggccggcaag gtggatgagg ccctggagct gttcgacgag    1860
atgaaggaga ggggcatcaa gcccgacgag vtyntndcks gkakkmkgts vvtyttdgck    1920
agdvdakmrs kgvknvvtyt tdgckagkvd admkrgkdvv tyntdgcksg kakkmkgtsv    1980
vtyttdgcka gdvdakmrsk gvknvvtytt dgckagkvda dmkrgkdvvt yntdgcksgk    2040
akkmkgtsvv tyttdgckag dvdakmrskg vknvvtyttd gckagkvdad mkrgkdvvty    2100
ntdgcksgka kkmkgtsvvt yttdgckagd vdakmrskgv knvvtyttdg ckagkvdadm    2160
```

```
krgkdvvtyn tdgcksgkak kmkgtsvvty ttdgckagdv dakmrskgvk nvvtyttdgc     2220
kagkvdadmk rgkdvvtynt dgcksgkakk mkgtsvvtyt tdgckagdvd akmrskgvkn     2280
vvtyttdgck agkvdadmkr gkd                                            2303

<210> SEQ ID NO 14
<211> LENGTH: 2303
<212> TYPE: DNA
<213> ORGANISM: Artificial sequence
<220> FEATURE:
<223> OTHER INFORMATION: PPR gene
<220> FEATURE:
<221> NAME/KEY: misc_feature
<222> LOCATION: (1894)..(1894)
<223> OTHER INFORMATION: n is a, c, g, t or u
<220> FEATURE:
<221> NAME/KEY: misc_feature
<222> LOCATION: (1896)..(1896)
<223> OTHER INFORMATION: n is a, c, g, t or u
<220> FEATURE:
<221> NAME/KEY: misc_feature
<222> LOCATION: (1935)..(1935)
<223> OTHER INFORMATION: n is a, c, g, t or u
<220> FEATURE:
<221> NAME/KEY: misc_feature
<222> LOCATION: (1963)..(1963)
<223> OTHER INFORMATION: n is a, c, g, t or u
<220> FEATURE:
<221> NAME/KEY: misc_feature
<222> LOCATION: (2004)..(2004)
<223> OTHER INFORMATION: n is a, c, g, t or u
<220> FEATURE:
<221> NAME/KEY: misc_feature
<222> LOCATION: (2032)..(2032)
<223> OTHER INFORMATION: n is a, c, g, t or u
<220> FEATURE:
<221> NAME/KEY: misc_feature
<222> LOCATION: (2073)..(2073)
<223> OTHER INFORMATION: n is a, c, g, t or u
<220> FEATURE:
<221> NAME/KEY: misc_feature
<222> LOCATION: (2101)..(2101)
<223> OTHER INFORMATION: n is a, c, g, t or u
<220> FEATURE:
<221> NAME/KEY: misc_feature
<222> LOCATION: (2142)..(2142)
<223> OTHER INFORMATION: n is a, c, g, t or u
<220> FEATURE:
<221> NAME/KEY: misc_feature
<222> LOCATION: (2170)..(2170)
<223> OTHER INFORMATION: n is a, c, g, t or u
<220> FEATURE:
<221> NAME/KEY: misc_feature
<222> LOCATION: (2211)..(2211)
<223> OTHER INFORMATION: n is a, c, g, t or u
<220> FEATURE:
<221> NAME/KEY: misc_feature
<222> LOCATION: (2239)..(2239)
<223> OTHER INFORMATION: n is a, c, g, t or u
<220> FEATURE:
<221> NAME/KEY: misc_feature
<222> LOCATION: (2280)..(2280)
<223> OTHER INFORMATION: n is a, c, g, t or u

<400> SEQUENCE: 14
gtcacataca acaccaacat cgacgaactg tgcaagagcg gcaagatcga ggaggccctg      60
aagctgttca aggagatgga ggagaagggc atcaccccca gcgtggtcac atacaccaca     120
ctgatcgacg gactgtgtaa agccggcgac gtggacgaag ccctcgagct gttcaaagag     180
atgcggagca agggcgtgaa gcccaacgtg gtgacataca ccaccctgat cgacggcctg     240
tgcaaggccg gcaaagtgga cgaggccctg gagctgttcg acgagatgaa ggagaggggc     300
atcaagcccg acgtggtcac atacaacacc ctgatcgacg gcctgtgcaa gagcggcaag     360
```

```
atcgaggagg ccctgaagct gttcaaggag atggaggaga agggcatcac ccccagcgtg    420
gttacataca ccacactgat cgacggactg tgtaaagccg gcgacgtgga cgaagccctc    480
gagctgttca aagagatgcg gagcaagggc gtgaagccca cgtggtcac atacaccacc     540 ctgatcgacg gcctgtgcaa ggccggcaag gtggatgagg ccctggagct gttcgacgag    600
atgaaggaga ggggcatcaa gcccgacgtg gttacataca acaccctgat cgacggcctg    660
tgcaagagcg gcaagatcga ggaggccctg aagctgttca aggagatgga ggagaagggc    720
atcaccccca gcgtggtcac atacaccaca ctgatcgacg gactgtgtaa agccggcgac    780
gtggacgaag ccctcgagct gttcaaagag atgcggagca agggcgtgaa gcccaacgtg    840
gtgacataca ccaccctgat cgacggcctg tgcaaggccg gcaaagtgga cgaggccctg    900
gagctgttcg acgagatgaa ggagaggggc atcaagcccg acgtggtcac atacaacacc    960
ctgatcgacg gcctgtgcaa gagcggcaag atcgaggagg ccctgaagct gttcaaggag    1020
atggaggaga agggcatcac ccccagcgtg gttacataca ccacactgat cgacggactg    1080
tgtaaagccg gcgacgtgga cgaagccctc gagctgttca aagagatgcg gagcaagggc    1140
gtgaagccca cgtggtcac atacaccacc ctgatcgacg gcctgtgcaa ggccggcaag     1200
gtggatgagg ccctggagct gttcgacgag atgaaggaga ggggcatcaa gcccgacgtg    1260
gtcacataca acaccctgat cgacggcctg tgcaagagcg gcaagatcga ggaggccctg    1320
aagctgttca aggagatgga ggagaagggc atcacccccca gcgtggtcac atacaccaca   1380
ctgatcgacg gactgtgtaa agccggcgac gtggacgaag ccctcgagct gttcaaagag    1440
atgcggagca agggcgtgaa gcccaacgtg gttacataca ccaccctgat cgacggcctg    1500
tgcaaggccg gcaaagtgga cgaggccctg gagctgttcg acgagatgaa ggagaggggc    1560
atcaagcccg acgtggtcac atacaacacc ctgatcgacg gcctgtgcaa gagcggcaag    1620
atcgaggagg ccctgaagct gttcaaggag atggaggaga agggcatcac ccccagcgtg    1680
gtgacataca ccacactgat cgacggactg tgtaaagccg gcgacgtgga cgaagccctc    1740
gagctgttca aagagatgcg gagcaagggc gtgaagccca cgtggtcac atacaccacc     1800 ctgatcgacg gcctgtgcaa ggccggcaag gtggatgagg ccctggagct gttcgacgag    1860
atgaaggaga ggggcatcaa gcccgacgag vtyntndcks gkakkmkgts vvtyttdgck    1920
agdvdakmrs kgvknvvtyt tdgckagkvd admkrgkdvv tyntdgcksg kakkmkgtsv    1980
vtyttdgcka gdvdakmrsk gvknvvtytt dgckagkvda dmkrgkdvvt yntdgcksgk    2040
akkmkgtsvv tyttdgckag dvdakmrskg vknvvtyttd gckagkvdad mkrgkdvvty    2100
ntdgcksgka kkmkgtsvvt yttdgckagd vdakmrskgv knvvtyttdg ckagkvdadm    2160
krgkdvvtyn tdgcksgkak kmkgtsvvty ttdgckagdv dakmrskgvk nvvtyttdgc    2220
kagkvdadmk rgkdvvtynt dgcksgkakk mkgtsvvtyt tdgckagdvd akmrskgvkn    2280
vvtyttdgck agkvdadmkr gkd                                            2303
```

```
<210> SEQ ID NO 15
<211> LENGTH: 2304
<212> TYPE: DNA
<213> ORGANISM: Artificial sequence
<220> FEATURE:
<223> OTHER INFORMATION: PPR gene
<220> FEATURE:
<221> NAME/KEY: misc_feature
<222> LOCATION: (1894)..(1894)
<223> OTHER INFORMATION: n is a, c, g, t or u
<220> FEATURE:
```

```
<221> NAME/KEY: misc_feature
<222> LOCATION: (1896)..(1896)
<223> OTHER INFORMATION: n is a, c, g, t or u
<220> FEATURE:
<221> NAME/KEY: misc_feature
<222> LOCATION: (1936)..(1936)
<223> OTHER INFORMATION: n is a, c, g, t or u
<220> FEATURE:
<221> NAME/KEY: misc_feature
<222> LOCATION: (1964)..(1964)
<223> OTHER INFORMATION: n is a, c, g, t or u
<220> FEATURE:
<221> NAME/KEY: misc_feature
<222> LOCATION: (2005)..(2005)
<223> OTHER INFORMATION: n is a, c, g, t or u
<220> FEATURE:
<221> NAME/KEY: misc_feature
<222> LOCATION: (2033)..(2033)
<223> OTHER INFORMATION: n is a, c, g, t or u
<220> FEATURE:
<221> NAME/KEY: misc_feature
<222> LOCATION: (2074)..(2074)
<223> OTHER INFORMATION: n is a, c, g, t or u
<220> FEATURE:
<221> NAME/KEY: misc_feature
<222> LOCATION: (2102)..(2102)
<223> OTHER INFORMATION: n is a, c, g, t or u
<220> FEATURE:
<221> NAME/KEY: misc_feature
<222> LOCATION: (2143)..(2143)
<223> OTHER INFORMATION: n is a, c, g, t or u
<220> FEATURE:
<221> NAME/KEY: misc_feature
<222> LOCATION: (2171)..(2171)
<223> OTHER INFORMATION: n is a, c, g, t or u
<220> FEATURE:
<221> NAME/KEY: misc_feature
<222> LOCATION: (2212)..(2212)
<223> OTHER INFORMATION: n is a, c, g, t or u
<220> FEATURE:
<221> NAME/KEY: misc_feature
<222> LOCATION: (2240)..(2240)
<223> OTHER INFORMATION: n is a, c, g, t or u
<220> FEATURE:
<221> NAME/KEY: misc_feature
<222> LOCATION: (2281)..(2281)
<223> OTHER INFORMATION: n is a, c, g, t or u

<400> SEQUENCE: 15
gtcacataca acaccaacat cgacaaactg tgcaagagcg gcaagatcga ggaggccctg      60
aagctgttca aggagatgga ggagaagggc atcaccccca gcgtggtcac atacaccaca     120
ctgatcgacg gactgtgtaa agccggcgac gtggacgaag ccctcgagct gttcaaagag     180
atgcggagca agggcgtgaa gcccaacgtg gtgacataca ccaccctgat cgacggcctg     240
tgcaaggccg gcaaagtgga cgaggccctg agctgttcg acgagatgaa ggagaggggc     300
atcaagcccg acgtggtcac atacaacacc ctgatcgacg gcctgtgcaa gagcggcaag     360
atcgaggagg ccctgaagct gttcaaggag atggaggaga agggcatcac ccccagcgtg     420
gttacataca ccacactgat cgacggactg tgtaaagccg gcgacgtgga cgaagccctc     480
gagctgttca aagagatgcg gagcaagggc gtgaagccca cgtggtcac atacaccacc     540 ctgatcgacg gcctgtgcaa ggccggcaag gtggatgagg ccctggagct gttcgacgag     600
atgaaggaga gggcatcaa gcccgacgtg gttacataca acaccctgat cgacggcctg     660
tgcaagagcg gcaagatcga ggaggccctg aagctgttca aggagatgga ggagaagggc     720
atcaccccca gcgtggtcac atacaccaca ctgatcgacg gactgtgtaa agccggcgac     780
gtggacgaag ccctcgagct gttcaaagag atgcggagca agggcgtgaa gcccaacgtg     840
gtgacataca ccaccctgat cgacggcctg tgcaaggccg gcaaagtgga cgaggccctg     900
```

```
gagctgttcg acgagatgaa ggagaggggc atcaagcccg acgtggtcac atacaacacc      960
ctgatcgacg gcctgtgcaa gagcggcaag atcgaggagg ccctgaagct gttcaaggag     1020
atggaggaga agggcatcac ccccagcgtg gttacataca ccacactgat cgacggactg     1080
tgtaaagccg gcgacgtgga cgaagccctc gagctgttca aagagatgcg gagcaagggc     1140
gtgaagccca acgtggtcac atacaccacc ctgatcgacg gcctgtgcaa ggccggcaag     1200
gtggatgagg ccctggagct gttcgacgag atgaaggaga gggcatcaa gcccgacgtg      1260 gtcacataca acaccctgat cgacggcctg tgcaagagcg gcaagatcga ggaggccctg     1320
aagctgttca aggagatgga ggagaagggc atcaccccca gcgtggtcac atacaccaca     1380
ctgatcgacg gactgtgtaa agccggcgac gtggacgaag ccctcgagct gttcaaagag     1440
atgcggagca agggcgtgaa gcccaacgtg gttacataca ccaccctgat cgacggcctg     1500
tgcaaggccg gcaaagtgga cgaggccctg gagctgttcg acgagatgaa ggagaggggc     1560
atcaagcccg acgtggtcac atacaacacc ctgatcgacg gcctgtgcaa gagcggcaag     1620
atcgaggagg ccctgaagct gttcaaggag atggaggaga agggcatcac ccccagcgtg     1680
gtgacataca ccacactgat cgacggactg tgtaaagccg gcgacgtgga cgaagccctc     1740
gagctgttca aagagatgcg gagcaagggc gtgaagccca acgtggtcac atacaccacc     1800
ctgatcgacg gcctgtgcaa ggccggcaag gtggatgagg ccctggagct gttcgacgag     1860
atgaaggaga ggggcatcaa gcccgacgag vtyntndkck sgkakkmkgt svvtyttdgc     1920
kagdvdakmr skgvknvvty ttdgckagkv dadmkrgkdv vtyntdgcks gkakkmkgts     1980
vvtyttdgck agdvdakmrs kgvknvvtyt tdgckagkvd admkrgkdvv tyntdgcksg     2040
kakkmkgtsv vtyttdgcka gdvdakmrsk gvknvvtytt dgckagkvda dmkrgkdvvt     2100
yntdgcksgk akkmkgtsvv tyttdgckag dvdakmrskg vknvvtyttd gckagkvdad     2160
mkrgkdvvty ntdgcksgka kkmkgtsvvt yttdgckagd vdakmrskgv knvvtyttdg     2220
ckagkvdadm krgkdvvtyn tdgcksgkak kmkgtsvvty ttdgckagdv dakmrskgvk     2280
nvvtyttdgc kagkvdadmk rgkd                                             2304
```

```
<210> SEQ ID NO 16
<211> LENGTH: 2304
<212> TYPE: DNA
<213> ORGANISM: Artificial sequence
<220> FEATURE:
<223> OTHER INFORMATION: PPR gene
<220> FEATURE:
<221> NAME/KEY: misc_feature
<222> LOCATION: (1894)..(1894)
<223> OTHER INFORMATION: n is a, c, g, t or u
<220> FEATURE:
<221> NAME/KEY: misc_feature
<222> LOCATION: (1936)..(1936)
<223> OTHER INFORMATION: n is a, c, g, t or u
<220> FEATURE:
<221> NAME/KEY: misc_feature
<222> LOCATION: (1964)..(1964)
<223> OTHER INFORMATION: n is a, c, g, t or u
<220> FEATURE:
<221> NAME/KEY: misc_feature
<222> LOCATION: (2005)..(2005)
<223> OTHER INFORMATION: n is a, c, g, t or u
<220> FEATURE:
<221> NAME/KEY: misc_feature
<222> LOCATION: (2033)..(2033)
<223> OTHER INFORMATION: n is a, c, g, t or u
<220> FEATURE:
<221> NAME/KEY: misc_feature
<222> LOCATION: (2074)..(2074)
```

-continued

```
<223> OTHER INFORMATION: n is a, c, g, t or u
<220> FEATURE:
<221> NAME/KEY: misc_feature
<222> LOCATION: (2102)..(2102)
<223> OTHER INFORMATION: n is a, c, g, t or u
<220> FEATURE:
<221> NAME/KEY: misc_feature
<222> LOCATION: (2143)..(2143)
<223> OTHER INFORMATION: n is a, c, g, t or u
<220> FEATURE:
<221> NAME/KEY: misc_feature
<222> LOCATION: (2171)..(2171)
<223> OTHER INFORMATION: n is a, c, g, t or u
<220> FEATURE:
<221> NAME/KEY: misc_feature
<222> LOCATION: (2212)..(2212)
<223> OTHER INFORMATION: n is a, c, g, t or u
<220> FEATURE:
<221> NAME/KEY: misc_feature
<222> LOCATION: (2240)..(2240)
<223> OTHER INFORMATION: n is a, c, g, t or u
<220> FEATURE:
<221> NAME/KEY: misc_feature
<222> LOCATION: (2281)..(2281)
<223> OTHER INFORMATION: n is a, c, g, t or u

<400> SEQUENCE: 16
gtcacataca acaccgatat cgacggcctg tgcaagagcg gcaagatcga ggaggccctg      60
aagctgttca aggagatgga ggagaagggc atcaccccca gcgtggtcac atacaccaca     120
ctgatcgacg gactgtgtaa agccggcgac gtggacgaag ccctcgagct gttcaaagag     180
atgcggagca agggcgtgaa gcccaacgtg gtgacataca ccaccctgat cgacggcctg     240
tgcaaggccg gcaaagtgga cgaggccctg gagctgttcg acgagatgaa ggagaggggc     300
atcaagcccg acgtggtcac atacaacacc ctgatcgacg gcctgtgcaa gagcggcaag     360
atcgaggagg ccctgaagct gttcaaggag atggaggaga agggcatcac ccccagcgtg     420
gttacataca ccacactgat cgacggactg tgtaaagccg gcgacgtgga cgaagccctc     480
gagctgttca aagagatgcg gagcaagggc gtgaagccca acgtggtcac atacaccacc     540
ctgatcgacg gcctgtgcaa ggccggcaag gtggatgagg ccctggagct gttcgacgag     600
atgaaggaga gggcatcaa gcccgacgtg gttacataca acaccctgat cgacggcctg     660
tgcaagagcg gcaagatcga ggaggccctg aagctgttca aggagatgga ggagaagggc     720 atcacccccca gcgtggtcac atacaccaca ctgatcgacg gactgtgtaa agccggcgac     780
gtggacgaag ccctcgagct gttcaaagag atgcggagca agggcgtgaa gcccaacgtg     840
gtgacataca ccaccctgat cgacggcctg tgcaaggccg gcaaagtgga cgaggccctg     900
gagctgttcg acgagatgaa ggagaggggc atcaagcccg acgtggtcac atacaacacc     960
ctgatcgacg gcctgtgcaa gagcggcaag atcgaggagg ccctgaagct gttcaaggag    1020
atggaggaga agggcatcac ccccagcgtg gttacataca ccacactgat cgacggactg    1080
tgtaaagccg gcgacgtgga cgaagccctc gagctgttca aagagatgcg gagcaagggc    1140
gtgaagccca acgtggtcac atacaccacc ctgatcgacg gcctgtgcaa ggccggcaag    1200
gtggatgagg ccctggagct gttcgacgag atgaaggaga ggggcatcaa gcccgacgtg    1260
gtcacataca acaccctgat cgacggcctg tgcaagagcg gcaagatcga ggaggccctg    1320
aagctgttca aggagatgga ggagaagggc atcacccccca gcgtggtcac atacaccaca    1380
ctgatcgacg gactgtgtaa agccggcgac gtggacgaag ccctcgagct gttcaaagag    1440
atgcggagca agggcgtgaa gcccaacgtg gttacataca ccaccctgat cgacggcctg    1500
tgcaaggccg gcaaagtgga cgaggccctg gagctgttcg acgagatgaa ggagaggggc    1560
```

```
atcaagcccg acgtggtcac atacaacacc ctgatcgacg gcctgtgcaa gagcggcaag      1620
atcgaggagg ccctgaagct gttcaaggag atggaggaga agggcatcac ccccagcgtg      1680
gtgacataca ccacactgat cgacggactg tgtaaagccg gcgacgtgga cgaagccctc      1740
gagctgttca aagagatgcg gagcaagggc gtgaagccca acgtggtcac atacaccacc      1800
ctgatcgacg gcctgtgcaa ggccggcaag gtggatgagg ccctggagct gttcgacgag      1860
atgaaggaga ggggcatcaa gcccgacgag vtyntddgck sgkakkmkgt svvtyttdgc      1920
kagdvdakmr skgvknvvty ttdgckagkv dadmkrgkdv vtyntdgcks gkakkmkgts      1980
vvtyttdgck agdvdakmrs kgvknvvtyt tdgckagkvd admkrgkdvv tyntdgcksg      2040
kakkmkgtsv vtyttdgcka gdvdakmrsk gvknvvtytt dgckagkvda dmkrgkdvvt      2100
yntdgcksgk akkmkgtsvv tyttdgckag dvdakmrskg vknvvtyttd gckagkvdad      2160
mkrgkdvvty ntdgcksgka kkmkgtsvvt yttdgckagd vdakmrskgv knvvtyttdg      2220
ckagkvdadm krgkdvvtyn tdgcksgkak kmkgtsvvty ttdgckagdv dakmrskgvk      2280
nvvtyttdgc kagkvdadmk rgkd                                            2304
```

```
<210> SEQ ID NO 17
<211> LENGTH: 3481
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2858)..(2858)
<223> OTHER INFORMATION: n is a, c, g, t or u
<220> FEATURE:
<221> NAME/KEY: misc_feature
<222> LOCATION: (2914)..(2914)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2934)..(2934)
<223> OTHER INFORMATION: n is a, c, g, t or u
<220> FEATURE:
<221> NAME/KEY: misc_feature
<222> LOCATION: (2939)..(2939)
<223> OTHER INFORMATION: n is a, c, g, t or u
<220> FEATURE:
<221> NAME/KEY: misc_feature
<222> LOCATION: (2941)..(2941)
<223> OTHER INFORMATION: n is a, c, g, t or u
<220> FEATURE:
<221> NAME/KEY: misc_feature
<222> LOCATION: (2944)..(2944)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2956)..(2956)
<223> OTHER INFORMATION: n is a, c, g, t or u
<220> FEATURE:
<221> NAME/KEY: misc_feature
<222> LOCATION: (2960)..(2960)
<223> OTHER INFORMATION: n is a, c, g, t or u
<220> FEATURE:
<221> NAME/KEY: misc_feature
<222> LOCATION: (2969)..(2969)
<223> OTHER INFORMATION: n is a, c, g, t or u
<220> FEATURE:
```

-continued

```
<221> NAME/KEY: misc_feature
<222> LOCATION: (2976)..(2976)
<223> OTHER INFORMATION: n is a, c, g, t or u
<220> FEATURE:
<221> NAME/KEY: misc_feature
<222> LOCATION: (2986)..(2986)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3029)..(3029)
<223> OTHER INFORMATION: n is a, c, g, t or u
<220> FEATURE:
<221> NAME/KEY: misc_feature
<222> LOCATION: (3070)..(3070)
<223> OTHER INFORMATION: n is a, c, g, t or u
<220> FEATURE:
<221> NAME/KEY: misc_feature
<222> LOCATION: (3098)..(3098)
<223> OTHER INFORMATION: n is a, c, g, t or u
<220> FEATURE:
<221> NAME/KEY: misc_feature
<222> LOCATION: (3139)..(3139)
<223> OTHER INFORMATION: n is a, c, g, t or u
<220> FEATURE:
<221> NAME/KEY: misc_feature
<222> LOCATION: (3167)..(3167)
<223> OTHER INFORMATION: n is a, c, g, t or u
<220> FEATURE:
<221> NAME/KEY: misc_feature
<222> LOCATION: (3208)..(3208)
<223> OTHER INFORMATION: n is a, c, g, t or u
<220> FEATURE:
<221> NAME/KEY: misc_feature
<222> LOCATION: (3236)..(3236)
<223> OTHER INFORMATION: n is a, c, g, t or u
<220> FEATURE:
<221> NAME/KEY: misc_feature
<222> LOCATION: (3277)..(3277)
<223> OTHER INFORMATION: n is a, c, g, t or u
<220> FEATURE:
<221> NAME/KEY: misc_feature
<222> LOCATION: (3305)..(3305)
<223> OTHER INFORMATION: n is a, c, g, t or u
<220> FEATURE:
<221> NAME/KEY: misc_feature
<222> LOCATION: (3346)..(3346)
<223> OTHER INFORMATION: n is a, c, g, t or u
<220> FEATURE:
<221> NAME/KEY: misc_feature
<222> LOCATION: (3374)..(3374)
<223> OTHER INFORMATION: n is a, c, g, t or u
<220> FEATURE:
<221> NAME/KEY: misc_feature
<222> LOCATION: (3415)..(3415)
<223> OTHER INFORMATION: n is a, c, g, t or u
<220> FEATURE:
<221> NAME/KEY: misc_feature
<222> LOCATION: (3441)..(3441)
<223> OTHER INFORMATION: n is a, c, g, t or u

<400> SEQUENCE: 17
atggccggag tgagcaaggg cgaggagctg ttcaccgggg tggtgcccat cctggtcgag      60
ctggacggcg acgtaaacgg ccacaagttc agcgtgtccg gcgagggcga gggcgatgcc     120
acctacggca agctgaccct gaagttcatc tgcaccaccg gcaagctgcc cgtgccctgg     180
cccaccctcg tgaccaccct gacctacggc gtgcagtgct tcagccgcta ccccgaccac     240
atgaagcagc acgacttctt caagtccgcc atgcccgaag ctacgtcca ggagcgcacc      300 atcttcttca aggacgacgg caactacaag acccgcgccg aggtgaagtt cgagggcgac     360
accctggtga accgcatcga gctgaagggc atcgacttca aggaggacgg caacatcctg     420
```

```
gggcacaagc tggagtacaa ctacaacagc cacaacgtct atatcatggc cgacaagcag      480
aagaacggca tcaaggtgaa cttcaagatc cgccacaaca tcgaggacgg cagcgtgcag      540
ctcgccgacc actaccagca gaacaccccc atcggcgacg gccccgtgct gctgcccgac      600
aaccactacc tgagcaccca gtccgccctg agcaaagacc ccaacgagaa gcgcgatcac      660
atggtcctgc tggagttcgt gaccgccgcc gggatcactc tcggcatgga cgagctgtac      720
aagccaaaga aaaagagaaa ggttagccat ggctccggcg gcagcggggg agggctccat      780
atgggaaact ccgtggtcac atacaacacc ctgatcgacg gcctgtgcaa gagcggcaag      840
atcgaggagg ccctgaagct gttcaaggag atggaggaga agggcatcac ccccagcgtg      900
gtcacataca ccacactgat cgacggactg tgtaaagccg gcgacgtgga cgaagccctc      960
gagctgttca aagagatgcg gagcaagggc gtgaagccca cgtggtgac atacaccacc      1020 ctgatcgacg gcctgtgcaa ggccggcaaa gtggacgagg ccctggagct gttcgacgag      1080
atgaaggaga ggggcatcaa gcccgacgtg gtcacataca acaccctgat cgacggcctg      1140
tgcaagagcg gcaagatcga ggaggccctg aagctgttca aggagatgga ggagaagggc      1200
atcaccccca gcgtggttac atacaccaca ctgatcgacg gactgtgtaa agccggcgac      1260
gtggacgaag ccctcgagct gttcaaagag atgcggagca agggcgtgaa gcccaacgtg      1320
gtcacataca ccaccctgat cgacggcctg tgcaaggccg gcaaggtgga tgaggccctg      1380
gagctgttcg acgagatgaa ggagaggggc atcaagcccg acgtggttac atacaacacc      1440
ctgatcgacg gcctgtgcaa gagcggcaag atcgaggagg ccctgaagct gttcaaggag      1500
atggaggaga agggcatcac ccccagcgtg gtcacataca ccacactgat cgacggactg      1560
tgtaaagccg gcgacgtgga cgaagccctc gagctgttca aagagatgcg gagcaagggc      1620
gtgaagccca cgtggtgac atacaccacc ctgatcgacg gcctgtgcaa ggccggcaaa      1680
gtggacgagg ccctggagct gttcgacgag atgaaggaga ggggcatcaa gcccgacgtg      1740
gtcacataca acaccctgat cgacggcctg tgcaagagcg gcaagatcga ggaggccctg      1800
aagctgttca aggagatgga ggagaagggc atcaccccca gcgtggttac atacaccaca      1860
ctgatcgacg gactgtgtaa agccggcgac gtggacgaag ccctcgagct gttcaaagag      1920
atgcggagca agggcgtgaa gcccaacgtg gtcacataca ccaccctgat cgacggcctg      1980
tgcaaggccg gcaaggtgga tgaggccctg gagctgttcg acgagatgaa ggagaggggc      2040
atcaagcccg acgtggtcac atacaacacc ctgatcgacg gcctgtgcaa gagcggcaag      2100
atcgaggagg ccctgaagct gttcaaggag atggaggaga agggcatcac ccccagcgtg      2160
gtcacataca ccacactgat cgacggactg tgtaaagccg gcgacgtgga cgaagccctc      2220
gagctgttca aagagatgcg gagcaagggc gtgaagccca cgtggttac atacaccacc      2280 ctgatcgacg gcctgtgcaa ggccggcaaa gtggacgagg ccctggagct gttcgacgag      2340
atgaaggaga ggggcatcaa gcccgacgtg gtcacataca acaccctgat cgacggcctg      2400
tgcaagagcg gcaagatcga ggaggccctg aagctgttca aggagatgga ggagaagggc      2460
atcaccccca gcgtggtgac atacaccaca ctgatcgacg gactgtgtaa agccggcgac      2520
gtggacgaag ccctcgagct gttcaaagag atgcggagca agggcgtgaa gcccaacgtg      2580
gtcacataca ccaccctgat cgacggcctg tgcaaggccg gcaaggtgga tgaggccctg      2640
gagctgttcg acgagatgaa ggagaggggc atcaagcccg acgagctgac ctacaacacc      2700
ctgatcagcg gcctgggcaa ggccggcaga gccagagacc ccccgtgct cagtagcggg      2760
```

```
gactataagg accacgacgg agactacaag gatcatgata ttgattacaa agacgatgac    2820
gataagatgg ccggacgcta gmagvskgtg vvvdgdvngh ksvsgggdat ygktkcttgk    2880
vwtvtttygv csrydhmkhd ksamgyvrtk ddgnyktrav kgdtvnrkgd kdgnghkyny    2940
nshnvymadk kngkvnkrhn dgsvadhynt gdgvdnhyst saskdnkrdh mvvtaagtgm    3000
dykkkkrkvs hgsggsgggh mgnsvvtynt dgcksgkakk mkgtsvvtyt tdgckagdvd    3060
akmrskgvkn vvtyttdgck agkvdadmkr gkdvvtyntd gcksgkakkm kgtsvvtytt    3120
dgckagdvda kmrskgvknv vtyttdgcka gkvdadmkrg kdvvtyntdg cksgkakkmk    3180
gtsvvtyttd gckagdvdak mrskgvknvv tyttdgckag kvdadmkrgk dvvtyntdgc    3240
ksgkakkmkg tsvvtyttdg ckagdvdakm rskgvknvvt yttdgckagk vdadmkrgkd    3300
vvtyntdgck sgkakkmkgt svvtyttdgc kagdvdakmr skgvknvvty ttdgckagkv    3360
dadmkrgkdv vtyntdgcks gkakkmkgts vvtyttdgck agdvdakmrs kgvknvvtyt    3420
tdgckagkvd admkrgkdty ntsggkagra rdvssgdykd hdgdykdhdd ykddddkmag    3480 r                                                                    3481
```

```
<210> SEQ ID NO 18
<211> LENGTH: 3480
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2858)..(2858)
<223> OTHER INFORMATION: n is a, c, g, t or u
<220> FEATURE:
<221> NAME/KEY: misc_feature
<222> LOCATION: (2914)..(2914)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2934)..(2934)
<223> OTHER INFORMATION: n is a, c, g, t or u
<220> FEATURE:
<221> NAME/KEY: misc_feature
<222> LOCATION: (2939)..(2939)
<223> OTHER INFORMATION: n is a, c, g, t or u
<220> FEATURE:
<221> NAME/KEY: misc_feature
<222> LOCATION: (2941)..(2941)
<223> OTHER INFORMATION: n is a, c, g, t or u
<220> FEATURE:
<221> NAME/KEY: misc_feature
<222> LOCATION: (2944)..(2944)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2956)..(2956)
<223> OTHER INFORMATION: n is a, c, g, t or u
<220> FEATURE:
<221> NAME/KEY: misc_feature
<222> LOCATION: (2960)..(2960)
<223> OTHER INFORMATION: n is a, c, g, t or u
<220> FEATURE:
<221> NAME/KEY: misc_feature
<222> LOCATION: (2969)..(2969)
<223> OTHER INFORMATION: n is a, c, g, t or u
<220> FEATURE:
<221> NAME/KEY: misc_feature
```

<222> LOCATION: (2976)..(2976)
<223> OTHER INFORMATION: n is a, c, g, t or u
<220> FEATURE:
<221> NAME/KEY: misc_feature
<222> LOCATION: (2986)..(2986)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3029)..(3029)
<223> OTHER INFORMATION: n is a, c, g, t or u
<220> FEATURE:
<221> NAME/KEY: misc_feature
<222> LOCATION: (3069)..(3069)
<223> OTHER INFORMATION: n is a, c, g, t or u
<220> FEATURE:
<221> NAME/KEY: misc_feature
<222> LOCATION: (3097)..(3097)
<223> OTHER INFORMATION: n is a, c, g, t or u
<220> FEATURE:
<221> NAME/KEY: misc_feature
<222> LOCATION: (3138)..(3138)
<223> OTHER INFORMATION: n is a, c, g, t or u
<220> FEATURE:
<221> NAME/KEY: misc_feature
<222> LOCATION: (3166)..(3166)
<223> OTHER INFORMATION: n is a, c, g, t or u
<220> FEATURE:
<221> NAME/KEY: misc_feature
<222> LOCATION: (3207)..(3207)
<223> OTHER INFORMATION: n is a, c, g, t or u
<220> FEATURE:
<221> NAME/KEY: misc_feature
<222> LOCATION: (3235)..(3235)
<223> OTHER INFORMATION: n is a, c, g, t or u
<220> FEATURE:
<221> NAME/KEY: misc_feature
<222> LOCATION: (3276)..(3276)
<223> OTHER INFORMATION: n is a, c, g, t or u
<220> FEATURE:
<221> NAME/KEY: misc_feature
<222> LOCATION: (3304)..(3304)
<223> OTHER INFORMATION: n is a, c, g, t or u
<220> FEATURE:
<221> NAME/KEY: misc_feature
<222> LOCATION: (3345)..(3345)
<223> OTHER INFORMATION: n is a, c, g, t or u
<220> FEATURE:
<221> NAME/KEY: misc_feature
<222> LOCATION: (3373)..(3373)
<223> OTHER INFORMATION: n is a, c, g, t or u
<220> FEATURE:
<221> NAME/KEY: misc_feature
<222> LOCATION: (3414)..(3414)
<223> OTHER INFORMATION: n is a, c, g, t or u
<220> FEATURE:
<221> NAME/KEY: misc_feature
<222> LOCATION: (3440)..(3440)
<223> OTHER INFORMATION: n is a, c, g, t or u

<400> SEQUENCE: 18
atggccggag tgagcaaggg cgaggagctg ttcaccgggg tggtgcccat cctggtcgag        60
ctggacggcg acgtaaacgg ccacaagttc agcgtgtccg gcgagggcga gggcgatgcc       120
acctacggca agctgaccct gaagttcatc tgcaccaccg gcaagctgcc cgtgccctgg       180
cccaccctcg tgaccaccct gacctacggc gtgcagtgct tcagccgcta ccccgaccac       240
atgaagcagc acgacttctt caagtccgcc atgcccgaag gctacgtcca ggagcgcacc       300
atcttcttca aggacgacgg caactacaag acccgcgccg aggtgaagtt cgagggcgac       360
accctggtga accgcatcga gctgaagggc atcgacttca aggaggacgg caacatcctg       420

-continued

```
gggcacaagc tggagtacaa ctacaacagc cacaacgtct atatcatggc cgacaagcag      480
aagaacggca tcaaggtgaa cttcaagatc cgccacaaca tcgaggacgg cagcgtgcag      540
ctcgccgacc actaccagca gaacacccce atcggcgacg ccccgtgct gctgcccgac       600 aaccactacc tgagcaccca gtccgccctg agcaaagacc ccaacgagaa gcgcgatcac      660
atggtcctgc tggagttcgt gaccgccgcc gggatcactc tcggcatgga cgagctgtac      720
aagccaaaga aaaagagaaa ggttagccat ggctccggcg gcagcggggg agggctccat      780
atgggaaact ccgtggtcac atacaacacc ctgatcgacg aactgtgcaa gagcggcaag      840
atcgaggagg ccctgaagct gttcaaggag atggaggaga agggcatcac ccccagcgtg      900
gtcacataca ccacactgat cgacggactg tgtaaagccg gcgacgtgga cgaagccctc      960
gagctgttca aagagatgcg gagcaagggc gtgaagccca cgtggtgac atacaccacc      1020 ctgatcgacg gcctgtgcaa ggccggcaaa gtggacgagg ccctggagct gttcgacgag      1080
atgaaggaga ggggcatcaa gcccgacgtg gtcacataca acaccctgat cgacggcctg      1140
tgcaagagcg gcaagatcga ggaggccctg aagctgttca aggagatgga ggagaagggc      1200
atcaccccca gcgtggttac atacaccaca ctgatcgacg gactgtgtaa agccggcgac      1260
gtggacgaag ccctcgagct gttcaaagag atgcgggagca agggcgtgaa gcccaacgtg      1320
gtcacataca ccaccctgat cgacggcctg tgcaaggccg gcaaggtgga tgaggccctg      1380
gagctgttcg acgagatgaa ggagaggggc atcaagcccg acgtggttac atacaacacc      1440
ctgatcgacg gcctgtgcaa gagcggcaag atcgaggagg ccctgaagct gttcaaggag      1500
atggaggaga agggcatcac ccccagcgtg gtcacataca ccacactgat cgacggactg      1560
tgtaaagccg gcgacgtgga cgaagccctc gagctgttca aagagatgcg gagcaagggc      1620
gtgaagccca cgtggtgac atacaccacc ctgatcgacg gcctgtgcaa ggccggcaaa      1680
gtggacgagg ccctggagct gttcgacgag atgaaggaga ggggcatcaa gcccgacgtg      1740
gtcacataca acaccctgat cgacggcctg tgcaagagcg gcaagatcga ggaggccctg      1800
aagctgttca aggagatgga ggagaagggc atcaccccca gcgtggttac atacaccaca      1860
ctgatcgacg gactgtgtaa agccggcgac gtggacgaag ccctcgagct gttcaaagag      1920
atgcggagca agggcgtgaa gcccaacgtg gtcacataca ccaccctgat cgacggcctg      1980
tgcaaggccg gcaaggtgga tgaggccctg gagctgttcg acgagatgaa ggagaggggc      2040
atcaagcccg acgtggtcac atacaacacc ctgatcgacg gcctgtgcaa gagcggcaag      2100
atcgaggagg ccctgaagct gttcaaggag atggaggaga agggcatcac ccccagcgtg      2160
gtcacataca ccacactgat cgacggactg tgtaaagccg gcgacgtgga cgaagccctc      2220
gagctgttca aagagatgcg gagcaagggc gtgaagccca cgtggttac atacaccacc      2280 ctgatcgacg gcctgtgcaa ggccggcaaa gtggacgagg ccctggagct gttcgacgag      2340
atgaaggaga ggggcatcaa gcccgacgtg gtcacataca acaccctgat cgacggcctg      2400
tgcaagagcg gcaagatcga ggaggccctg aagctgttca aggagatgga ggagaagggc      2460
atcaccccca gcgtggtgac atacaccaca ctgatcgacg gactgtgtaa agccggcgac      2520
gtggacgaag ccctcgagct gttcaaagag atgcggagca agggcgtgaa gcccaacgtg      2580
gtcacataca ccaccctgat cgacggcctg tgcaaggccg gcaaggtgga tgaggccctg      2640
gagctgttcg acgagatgaa ggagaggggc atcaagcccg acgagctgac ctacaacacc      2700
ctgatcagcg gcctgggcaa ggccggcaga gccagagacc cccccgtgct cagtagcggg      2760
gactataagg accacgacgg agactacaag gatcatgata ttgattacaa agacgatgac      2820
```

```
gataagatgg ccggacgcta gmagvskgtg vvvdgdvngh ksvsgggdat ygktkcttgk        2880
vwtvtttygv csrydhmkhd ksamgyvrtk ddgnyktrav kgdtvnrkgd kdgnghkyny        2940
nshnvymadk kngkvnkrhn dgsvadhynt gdgvdnhyst saskdnkrdh mvvtaagtgm        3000
dykkkkrkvs hgsggsgggh mgnsvvtynt dcksgkakkm kgtsvvtytt dgckagdvda        3060
kmrskgvknv vtyttdgcka gkvdadmkrg kdvvtyntdg cksgkakkmk gtsvvtyttd        3120
gckagdvdak mrskgvknvv tyttdgckag kvdadmkrgk dvvtyntdgc ksgkakkmkg        3180
tsvvtyttdg ckagdvdakm rskgvknvvt yttdgckagk vdadmkrgkd vvtyntdgck        3240
sgkakkmkgt svvtyttdgc kagdvdakmr skgvknvvty ttdgckagkv dadmkrgkdv        3300
vtyntdgcks gkakkmkgts vvtyttdgck agdvdakmrs kgvknvvtyt tdgckagkvd        3360
admkrgkdvv tyntdgcksg kakkmkgtsv vtyttdgcka gdvdakmrsk gvknvvtytt        3420
dgckagkvda dmkrgkdtyn tsggkagrar dvssgdykdh dgdykdhddy kdddkmagr         3480
```

```
<210> SEQ ID NO 19
<211> LENGTH: 3481
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2858)..(2858)
<223> OTHER INFORMATION: n is a, c, g, t or u
<220> FEATURE:
<221> NAME/KEY: misc_feature
<222> LOCATION: (2914)..(2914)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2934)..(2934)
<223> OTHER INFORMATION: n is a, c, g, t or u
<220> FEATURE:
<221> NAME/KEY: misc_feature
<222> LOCATION: (2939)..(2939)
<223> OTHER INFORMATION: n is a, c, g, t or u
<220> FEATURE:
<221> NAME/KEY: misc_feature
<222> LOCATION: (2941)..(2941)
<223> OTHER INFORMATION: n is a, c, g, t or u
<220> FEATURE:
<221> NAME/KEY: misc_feature
<222> LOCATION: (2944)..(2944)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2956)..(2956)
<223> OTHER INFORMATION: n is a, c, g, t or u
<220> FEATURE:
<221> NAME/KEY: misc_feature
<222> LOCATION: (2960)..(2960)
<223> OTHER INFORMATION: n is a, c, g, t or u
<220> FEATURE:
<221> NAME/KEY: misc_feature
<222> LOCATION: (2969)..(2969)
<223> OTHER INFORMATION: n is a, c, g, t or u
<220> FEATURE:
<221> NAME/KEY: misc_feature
<222> LOCATION: (2976)..(2976)
<223> OTHER INFORMATION: n is a, c, g, t or u
<220> FEATURE:
```

-continued

```
<221> NAME/KEY: misc_feature
<222> LOCATION: (2986)..(2986)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3029)..(3029)
<223> OTHER INFORMATION: n is a, c, g, t or u
<220> FEATURE:
<221> NAME/KEY: misc_feature
<222> LOCATION: (3031)..(3031)
<223> OTHER INFORMATION: n is a, c, g, t or u
<220> FEATURE:
<221> NAME/KEY: misc_feature
<222> LOCATION: (3070)..(3070)
<223> OTHER INFORMATION: n is a, c, g, t or u
<220> FEATURE:
<221> NAME/KEY: misc_feature
<222> LOCATION: (3098)..(3098)
<223> OTHER INFORMATION: n is a, c, g, t or u
<220> FEATURE:
<221> NAME/KEY: misc_feature
<222> LOCATION: (3139)..(3139)
<223> OTHER INFORMATION: n is a, c, g, t or u
<220> FEATURE:
<221> NAME/KEY: misc_feature
<222> LOCATION: (3167)..(3167)
<223> OTHER INFORMATION: n is a, c, g, t or u
<220> FEATURE:
<221> NAME/KEY: misc_feature
<222> LOCATION: (3208)..(3208)
<223> OTHER INFORMATION: n is a, c, g, t or u
<220> FEATURE:
<221> NAME/KEY: misc_feature
<222> LOCATION: (3236)..(3236)
<223> OTHER INFORMATION: n is a, c, g, t or u
<220> FEATURE:
<221> NAME/KEY: misc_feature
<222> LOCATION: (3277)..(3277)
<223> OTHER INFORMATION: n is a, c, g, t or u
<220> FEATURE:
<221> NAME/KEY: misc_feature
<222> LOCATION: (3305)..(3305)
<223> OTHER INFORMATION: n is a, c, g, t or u
<220> FEATURE:
<221> NAME/KEY: misc_feature
<222> LOCATION: (3346)..(3346)
<223> OTHER INFORMATION: n is a, c, g, t or u
<220> FEATURE:
<221> NAME/KEY: misc_feature
<222> LOCATION: (3374)..(3374)
<223> OTHER INFORMATION: n is a, c, g, t or u
<220> FEATURE:
<221> NAME/KEY: misc_feature
<222> LOCATION: (3415)..(3415)
<223> OTHER INFORMATION: n is a, c, g, t or u
<220> FEATURE:
<221> NAME/KEY: misc_feature
<222> LOCATION: (3441)..(3441)
<223> OTHER INFORMATION: n is a, c, g, t or u

<400> SEQUENCE: 19
atggccggag tgagcaaggg cgaggagctg ttcaccgggg tggtgcccat cctggtcgag      60
ctggacggcg acgtaaacgg ccacaagttc agcgtgtccg gcgagggcga gggcgatgcc     120
acctacggca agctgaccct gaagttcatc tgcaccaccg gcaagctgcc cgtgccctgg     180
cccaccctcg tgaccaccct gacctacggc gtgcagtgct tcagccgcta ccccgaccac     240
atgaagcagc acgacttctt caagtccgcc atgcccgaag ctacgtcca ggagcgcacc      300 atcttcttca aggacgacgg caactacaag acccgcgccg aggtgaagtt cgagggcgac     360
accctggtga accgcatcga gctgaagggc atcgacttca aggaggacgg caacatcctg     420
```

-continued

```
gggcacaagc tggagtacaa ctacaacagc cacaacgtct atatcatggc cgacaagcag    480
aagaacggca tcaaggtgaa cttcaagatc cgccacaaca tcgaggacgg cagcgtgcag    540
ctcgccgacc actaccagca gaacacccc atcggcgacg gccccgtgct gctgcccgac     600
aaccactacc tgagcaccca gtccgccctg agcaaagacc ccaacgagaa gcgcgatcac    660
atggtcctgc tggagttcgt gaccgccgcc gggatcactc tcggcatgga cgagctgtac    720
aagccaaaga aaaagagaaa ggttagccat ggctccggcg gcagcggggg agggctccat    780
atgggaaact ccgtggtcac atacaacacc aacatcgacc agctgtgcaa gagcggcaag    840
atcgaggagg ccctgaagct gttcaaggag atggaggaga agggcatcac ccccagcgtg    900
gtcacataca ccacactgat cgacggactg tgtaaagccg gcgacgtgga cgaagccctc    960
gagctgttca aagagatgcg gagcaagggc gtgaagccca cgtggtgac atacaccacc     1020 ctgatcgacg gcctgtgcaa ggccggcaaa gtggacgagg ccctggagct gttcgacgag    1080
atgaaggaga ggggcatcaa gcccgacgtg gtcacataca acaccctgat cgacggcctg    1140
tgcaagagcg gcaagatcga ggaggccctg aagctgttca aggagatgga ggagaagggc    1200
atcaccccca gcgtggttac atacaccaca ctgatcgacg gactgtgtaa agccggcgac    1260
gtggacgaag ccctcgagct gttcaaagag atgcggagca agggcgtgaa gcccaacgtg    1320
gtcacataca ccaccctgat cgacggcctg tgcaaggccg gcaaggtgga tgaggccctg    1380
gagctgttcg acgagatgaa ggagaggggc atcaagcccg acgtggttac atacaacacc    1440
ctgatcgacg gcctgtgcaa gagcggcaag atcgaggagg ccctgaagct gttcaaggag    1500
atggaggaga agggcatcac ccccagcgtg gtcacataca ccacactgat cgacggactg    1560
tgtaaagccg gcgacgtgga cgaagccctc gagctgttca aagagatgcg gagcaagggc    1620
gtgaagccca cgtggtgac atacaccacc ctgatcgacg gcctgtgcaa ggccggcaaa    1680
gtggacgagg ccctggagct gttcgacgag atgaaggaga ggggcatcaa gcccgacgtg    1740
gtcacataca acaccctgat cgacggcctg tgcaagagcg gcaagatcga ggaggccctg    1800
aagctgttca aggagatgga ggagaagggc atcaccccca gcgtggttac atacaccaca    1860
ctgatcgacg gactgtgtaa agccggcgac gtggacgaag ccctcgagct gttcaaagag    1920
atgcggagca agggcgtgaa gcccaacgtg gtcacataca ccaccctgat cgacggcctg    1980
tgcaaggccg gcaaggtgga tgaggccctg gagctgttcg acgagatgaa ggagaggggc    2040
atcaagcccg acgtggtcac atacaacacc ctgatcgacg gcctgtgcaa gagcggcaag    2100
atcgaggagg ccctgaagct gttcaaggag atggaggaga agggcatcac ccccagcgtg    2160
gtcacataca ccacactgat cgacggactg tgtaaagccg gcgacgtgga cgaagccctc    2220
gagctgttca aagagatgcg gagcaagggc gtgaagccca cgtggttac atacaccacc     2280 ctgatcgacg gcctgtgcaa ggccggcaaa gtggacgagg ccctggagct gttcgacgag    2340
atgaaggaga ggggcatcaa gcccgacgtg gtcacataca acaccctgat cgacggcctg    2400
tgcaagagcg gcaagatcga ggaggccctg aagctgttca aggagatgga ggagaagggc    2460
atcaccccca gcgtggtgac atacaccaca ctgatcgacg gactgtgtaa agccggcgac    2520
gtggacgaag ccctcgagct gttcaaagag atgcggagca agggcgtgaa gcccaacgtg    2580
gtcacataca ccaccctgat cgacggcctg tgcaaggccg gcaaggtgga tgaggccctg    2640
gagctgttcg acgagatgaa ggagaggggc atcaagcccg acgagctgac ctacaacacc    2700
ctgatcagcg gcctgggcaa ggccggcaga gccagagacc ccccgtgct cagtagcggg     2760
```

-continued

```
gactataagg accacgacgg agactacaag gatcatgata ttgattacaa agacgatgac    2820
gataagatgg ccggacgcta gmagvskgtg vvvdgdvngh ksvsgggdat ygktkcttgk    2880
vwtvtttygv csrydhmkhd ksamgyvrtk ddgnyktrav kgdtvnrkgd kdgnghkyny    2940
nshnvymadk kngkvnkrhn dgsvadhynt gdgvdnhyst saskdnkrdh mvvtaagtgm    3000
dykkkkrkvs hgsggsgggh mgnsvvtynt ndcksgkakk mkgtsvvtyt tdgckagdvd    3060
akmrskgvkn vvtyttdgck agkvdadmkr gkdvvtyntd gcksgkakkm kgtsvvtytt    3120
dgckagdvda kmrskgvknv vtyttdgcka gkvdadmkrg kdvvtyntdg cksgkakkmk    3180
gtsvvtyttd gckagdvdak mrskgvknvv tyttdgckag kvdadmkrgk dvvtyntdgc    3240
ksgkakkmkg tsvvtyttdg ckagdvdakm rskgvknvvt yttdgckagk vdadmkrgkd    3300
vvtyntdgck sgkakkmkgt svvtyttdgc kagdvdakmr skgvknvvty ttdgckagkv    3360
dadmkrgkdv vtyntdgcks gkakkmkgts vvtyttdgck agdvdakmrs kgvknvvtyt    3420
tdgckagkvd admkrgkdty ntsggkagra rdvssgdykd hdgdykdhdd ykddddkmag    3480 r                                                                    3481
```

```
<210> SEQ ID NO 20
<211> LENGTH: 3481
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2858)..(2858)
<223> OTHER INFORMATION: n is a, c, g, t or u
<220> FEATURE:
<221> NAME/KEY: misc_feature
<222> LOCATION: (2914)..(2914)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2934)..(2934)
<223> OTHER INFORMATION: n is a, c, g, t or u
<220> FEATURE:
<221> NAME/KEY: misc_feature
<222> LOCATION: (2939)..(2939)
<223> OTHER INFORMATION: n is a, c, g, t or u
<220> FEATURE:
<221> NAME/KEY: misc_feature
<222> LOCATION: (2941)..(2941)
<223> OTHER INFORMATION: n is a, c, g, t or u
<220> FEATURE:
<221> NAME/KEY: misc_feature
<222> LOCATION: (2944)..(2944)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2956)..(2956)
<223> OTHER INFORMATION: n is a, c, g, t or u
<220> FEATURE:
<221> NAME/KEY: misc_feature
<222> LOCATION: (2960)..(2960)
<223> OTHER INFORMATION: n is a, c, g, t or u
<220> FEATURE:
<221> NAME/KEY: misc_feature
<222> LOCATION: (2969)..(2969)
<223> OTHER INFORMATION: n is a, c, g, t or u
<220> FEATURE:
<221> NAME/KEY: misc_feature
```

-continued

```
<222> LOCATION: (2976)..(2976)
<223> OTHER INFORMATION: n is a, c, g, t or u
<220> FEATURE:
<221> NAME/KEY: misc_feature
<222> LOCATION: (2986)..(2986)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3029)..(3029)
<223> OTHER INFORMATION: n is a, c, g, t or u
<220> FEATURE:
<221> NAME/KEY: misc_feature
<222> LOCATION: (3031)..(3031)
<223> OTHER INFORMATION: n is a, c, g, t or u
<220> FEATURE:
<221> NAME/KEY: misc_feature
<222> LOCATION: (3070)..(3070)
<223> OTHER INFORMATION: n is a, c, g, t or u
<220> FEATURE:
<221> NAME/KEY: misc_feature
<222> LOCATION: (3098)..(3098)
<223> OTHER INFORMATION: n is a, c, g, t or u
<220> FEATURE:
<221> NAME/KEY: misc_feature
<222> LOCATION: (3139)..(3139)
<223> OTHER INFORMATION: n is a, c, g, t or u
<220> FEATURE:
<221> NAME/KEY: misc_feature
<222> LOCATION: (3167)..(3167)
<223> OTHER INFORMATION: n is a, c, g, t or u
<220> FEATURE:
<221> NAME/KEY: misc_feature
<222> LOCATION: (3208)..(3208)
<223> OTHER INFORMATION: n is a, c, g, t or u
<220> FEATURE:
<221> NAME/KEY: misc_feature
<222> LOCATION: (3236)..(3236)
<223> OTHER INFORMATION: n is a, c, g, t or u
<220> FEATURE:
<221> NAME/KEY: misc_feature
<222> LOCATION: (3277)..(3277)
<223> OTHER INFORMATION: n is a, c, g, t or u
<220> FEATURE:
<221> NAME/KEY: misc_feature
<222> LOCATION: (3305)..(3305)
<223> OTHER INFORMATION: n is a, c, g, t or u
<220> FEATURE:
<221> NAME/KEY: misc_feature
<222> LOCATION: (3346)..(3346)
<223> OTHER INFORMATION: n is a, c, g, t or u
<220> FEATURE:
<221> NAME/KEY: misc_feature
<222> LOCATION: (3374)..(3374)
<223> OTHER INFORMATION: n is a, c, g, t or u
<220> FEATURE:
<221> NAME/KEY: misc_feature
<222> LOCATION: (3415)..(3415)
<223> OTHER INFORMATION: n is a, c, g, t or u
<220> FEATURE:
<221> NAME/KEY: misc_feature
<222> LOCATION: (3441)..(3441)
<223> OTHER INFORMATION: n is a, c, g, t or u

<400> SEQUENCE: 20
atggccggag tgagcaaggg cgaggagctg ttcaccgggg tggtgcccat cctggtcgag        60
ctggacggcg acgtaaacgg ccacaagttc agcgtgtccg gcgagggcga gggcgatgcc       120
acctacggca agctgaccct gaagttcatc tgcaccaccg gcaagctgcc cgtgccctgg       180
cccaccctcg tgaccaccct gacctacggc gtgcagtgct tcagccgcta ccccgaccac       240
atgaagcagc acgacttctt caagtccgcc atgcccgaag gctacgtcca ggagcgcacc       300
```

```
atcttcttca aggacgacgg caactacaag acccgcgccg aggtgaagtt cgagggcgac      360
accctggtga accgcatcga gctgaagggc atcgacttca aggaggacgg caacatcctg      420
gggcacaagc tggagtacaa ctacaacagc cacaacgtct atatcatggc cgacaagcag      480
aagaacggca tcaaggtgaa cttcaagatc cgccacaaca tcgaggacgg cagcgtgcag      540
ctcgccgacc actaccagca gaacacccc atcggcgacg gccccgtgct gctgcccgac      600
aaccactacc tgagcaccca gtccgccctg agcaaagacc ccaacgagaa gcgcgatcac      660
atggtcctgc tggagttcgt gaccgccgcc gggatcactc tcggcatgga cgagctgtac      720
aagccaaaga aaaagagaaa ggttagccat ggctccggcg gcagcggggg agggctccat      780
atgggaaact ccgtggtcac atacaacacc aacatcgacg aactgtgcaa gagcggcaag      840
atcgaggagg ccctgaagct gttcaaggag atggaggaga agggcatcac ccccagcgtg      900
gtcacataca ccacactgat cgacggactg tgtaaagccg gcgacgtgga cgaagccctc      960
gagctgttca aagagatgcg gagcaagggc gtgaagccca cgtggtgac atacaccacc     1020 ctgatcgacg gcctgtgcaa ggccggcaaa gtggacgagg ccctggagct gttcgacgag     1080
atgaaggaga ggggcatcaa gcccgacgtg gtcacataca acaccctgat cgacggcctg     1140
tgcaagagcg gcaagatcga ggaggccctg aagctgttca aggagatgga ggagaagggc     1200 atcacccca gcgtggttac atacaccaca ctgatcgacg gactgtgtaa agccggcgac     1260
gtggacgaag ccctcgagct gttcaaagag atgcggagca agggcgtgaa gcccaacgtg     1320
gtcacataca ccaccctgat cgacggcctg tgcaaggccg gcaaggtgga tgaggccctg     1380
gagctgttcg acgagatgaa ggagaggggc atcaagcccg acgtggttac atacaacacc     1440
ctgatcgacg gcctgtgcaa gagcggcaag atcgaggagg ccctgaagct gttcaaggag     1500
atggaggaga aagggcatcac ccccagcgtg gtcacataca ccacactgat cgacggactg    1560
tgtaaagccg gcgacgtgga cgaagccctc gagctgttca aagagatgcg gagcaagggc     1620
gtgaagccca cgtggtgac atacaccacc ctgatcgacg gcctgtgcaa ggccggcaaa     1680
gtggacgagg ccctggagct gttcgacgag atgaaggaga ggggcatcaa gcccgacgtg     1740
gtcacataca acaccctgat cgacggcctg tgcaagagcg gcaagatcga ggaggccctg     1800
aagctgttca aggagatgga ggagaagggc atcacccca gcgtggttac atacaccaca     1860
ctgatcgacg gactgtgtaa agccggcgac gtggacgaag ccctcgagct gttcaaagag     1920
atgcggagca agggcgtgaa gcccaacgtg gtcacataca ccaccctgat cgacggcctg     1980
tgcaaggccg gcaaggtgga tgaggccctg gagctgttcg acgagatgaa ggagaggggc     2040
atcaagcccg acgtggtcac atacaacacc ctgatcgacg gcctgtgcaa gagcggcaag     2100
atcgaggagg ccctgaagct gttcaaggag atggaggaga aagggcatcac ccccagcgtg    2160 gtcacataca ccacactgat cgacggactg tgtaaagccg gcgacgtgga cgaagccctc     2220
gagctgttca aagagatgcg gagcaagggc gtgaagccca cgtggttac atacaccacc     2280 ctgatcgacg gcctgtgcaa ggccggcaaa gtggacgagg ccctggagct gttcgacgag     2340
atgaaggaga ggggcatcaa gcccgacgtg gtcacataca acaccctgat cgacggcctg     2400
tgcaagagcg gcaagatcga ggaggccctg aagctgttca aggagatgga ggagaagggc     2460 atcacccca gcgtggtgac atacaccaca ctgatcgacg gactgtgtaa agccggcgac     2520
gtggacgaag ccctcgagct gttcaaagag atgcggagca agggcgtgaa gcccaacgtg     2580
gtcacataca ccaccctgat cgacggcctg tgcaaggccg gcaaggtgga tgaggccctg     2640
gagctgttcg acgagatgaa ggagaggggc atcaagcccg acgagctgac ctacaacacc     2700
```

```
ctgatcagcg gcctgggcaa ggccggcaga gccagagacc cccccgtgct cagtagcggg     2760
gactataagg accacgacgg agactacaag gatcatgata ttgattacaa agacgatgac     2820
gataagatgg ccggacgcta gmagvskgtg vvvdgdvngh ksvsgggdat ygktkcttgk     2880
vwtvtttygv csrydhmkhd ksamgyvrtk ddgnyktrav kgdtvnrkgd kdgnghkyny     2940
nshnvymadk kngkvnkrhn dgsvadhynt gdgvdnhyst saskdnkrdh mvvtaagtgm     3000
dykkkkrkvs hgsggsgggh mgnsvvtynt ndcksgkakk mkgtsvvtyt tdgckagdvd     3060
akmrskgvkn vvtyttdgck agkvdadmkr gkdvvtyntd gcksgkakkm kgtsvvtytt     3120
dgckagdvda kmrskgvknv vtyttdgcka gkvdadmkrg kdvvtyntdg cksgkakkmk     3180
gtsvvtyttd gckagdvdak mrskgvknvv tyttdgckag kvdadmkrgk dvvtyntdgc     3240
ksgkakkmkg tsvvtyttdg ckagdvdakm rskgvknvvt yttdgckagk vdadmkrgkd     3300
vvtyntdgck sgkakkmkgt svvtyttdgc kagdvdakmr skgvknvvty ttdgckagkv     3360
dadmkrgkdv vtyntdgcks gkakkmkgts vvtyttdgck agdvdakmrs kgvknvvtyt     3420
tdgckagkvd admkrgkdty ntsggkagra rdvssgdykd hdgdykdhdd ykddddkmag     3480 r                                                                    3481
```

<210> SEQ ID NO 21
<211> LENGTH: 3482
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2858)..(2858)
<223> OTHER INFORMATION: n is a, c, g, t or u
<220> FEATURE:
<221> NAME/KEY: misc_feature
<222> LOCATION: (2914)..(2914)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2934)..(2934)
<223> OTHER INFORMATION: n is a, c, g, t or u
<220> FEATURE:
<221> NAME/KEY: misc_feature
<222> LOCATION: (2939)..(2939)
<223> OTHER INFORMATION: n is a, c, g, t or u
<220> FEATURE:
<221> NAME/KEY: misc_feature
<222> LOCATION: (2941)..(2941)
<223> OTHER INFORMATION: n is a, c, g, t or u
<220> FEATURE:
<221> NAME/KEY: misc_feature
<222> LOCATION: (2944)..(2944)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2956)..(2956)
<223> OTHER INFORMATION: n is a, c, g, t or u
<220> FEATURE:
<221> NAME/KEY: misc_feature
<222> LOCATION: (2960)..(2960)
<223> OTHER INFORMATION: n is a, c, g, t or u
<220> FEATURE:
<221> NAME/KEY: misc_feature
<222> LOCATION: (2969)..(2969)

```
<223> OTHER INFORMATION: n is a, c, g, t or u
<220> FEATURE:
<221> NAME/KEY: misc_feature
<222> LOCATION: (2976)..(2976)
<223> OTHER INFORMATION: n is a, c, g, t or u
<220> FEATURE:
<221> NAME/KEY: misc_feature
<222> LOCATION: (2986)..(2986)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3029)..(3029)
<223> OTHER INFORMATION: n is a, c, g, t or u
<220> FEATURE:
<221> NAME/KEY: misc_feature
<222> LOCATION: (3031)..(3031)
<223> OTHER INFORMATION: n is a, c, g, t or u
<220> FEATURE:
<221> NAME/KEY: misc_feature
<222> LOCATION: (3071)..(3071)
<223> OTHER INFORMATION: n is a, c, g, t or u
<220> FEATURE:
<221> NAME/KEY: misc_feature
<222> LOCATION: (3099)..(3099)
<223> OTHER INFORMATION: n is a, c, g, t or u
<220> FEATURE:
<221> NAME/KEY: misc_feature
<222> LOCATION: (3140)..(3140)
<223> OTHER INFORMATION: n is a, c, g, t or u
<220> FEATURE:
<221> NAME/KEY: misc_feature
<222> LOCATION: (3168)..(3168)
<223> OTHER INFORMATION: n is a, c, g, t or u
<220> FEATURE:
<221> NAME/KEY: misc_feature
<222> LOCATION: (3209)..(3209)
<223> OTHER INFORMATION: n is a, c, g, t or u
<220> FEATURE:
<221> NAME/KEY: misc_feature
<222> LOCATION: (3237)..(3237)
<223> OTHER INFORMATION: n is a, c, g, t or u
<220> FEATURE:
<221> NAME/KEY: misc_feature
<222> LOCATION: (3278)..(3278)
<223> OTHER INFORMATION: n is a, c, g, t or u
<220> FEATURE:
<221> NAME/KEY: misc_feature
<222> LOCATION: (3306)..(3306)
<223> OTHER INFORMATION: n is a, c, g, t or u
<220> FEATURE:
<221> NAME/KEY: misc_feature
<222> LOCATION: (3347)..(3347)
<223> OTHER INFORMATION: n is a, c, g, t or u
<220> FEATURE:
<221> NAME/KEY: misc_feature
<222> LOCATION: (3375)..(3375)
<223> OTHER INFORMATION: n is a, c, g, t or u
<220> FEATURE:
<221> NAME/KEY: misc_feature
<222> LOCATION: (3416)..(3416)
<223> OTHER INFORMATION: n is a, c, g, t or u
<220> FEATURE:
<221> NAME/KEY: misc_feature
<222> LOCATION: (3442)..(3442)
<223> OTHER INFORMATION: n is a, c, g, t or u

<400> SEQUENCE: 21
atggccggag tgagcaaggg cgaggagctg ttcaccgggg tggtgcccat cctggtcgag        60
ctggacggcg acgtaaacgg ccacaagttc agcgtgtccg gcgagggcga gggcgatgcc       120
acctacggca agctgaccct gaagttcatc tgcaccaccg gcaagctgcc cgtgccctgg       180
cccaccctcg tgaccaccct gacctacggc gtgcagtgct tcagccgcta ccccgaccac       240
```

-continued

```
atgaagcagc acgacttctt caagtccgcc atgcccgaag gctacgtcca ggagcgcacc     300
atcttcttca aggacgacgg caactacaag acccgcgccg aggtgaagtt cgagggcgac     360
accctggtga accgcatcga gctgaagggc atcgacttca aggaggacgg caacatcctg     420
gggcacaagc tggagtacaa ctacaacagc cacaacgtct atatcatggc cgacaagcag     480
aagaacggca tcaaggtgaa cttcaagatc cgccacaaca tcgaggacgg cagcgtgcag     540
ctcgccgacc actaccagca gaacacccc atcggcgacg gccccgtgct gctgcccgac      600
aaccactacc tgagcaccca gtccgccctg agcaaagacc ccaacgagaa gcgcgatcac     660
atggtcctgc tggagttcgt gaccgccgcc gggatcactc tcggcatgga cgagctgtac     720
aagccaaaga aaaagagaaa ggttagccat ggctccggcg gcagcggggg agggctccat     780
atgggaaact ccgtggtcac atacaacacc aacatcgaca aactgtgcaa gagcggcaag     840
atcgaggagg ccctgaagct gttcaaggag atggaggaga agggcatcac ccccagcgtg     900
gtcacataca ccacactgat cgacggactg tgtaaagccg gcgacgtgga cgaagccctc     960
gagctgttca aagagatgcg gagcaagggc gtgaagccca cgtggtgac atacaccacc     1020 ctgatcgacg gcctgtgcaa ggccggcaaa gtggacgagg ccctggagct gttcgacgag    1080
atgaaggaga ggggcatcaa gcccgacgtg gtcacataca acaccctgat cgacggcctg    1140
tgcaagagcg gcaagatcga ggaggccctg aagctgttca aggagatgga ggagaagggc    1200 atcacccca gcgtggttac atacaccaca ctgatcgacg gactgtgtaa agccggcgac     1260
gtggacgaag ccctcgagct gttcaaagag atgcggagca aggcgtgaa gcccaacgtg    1320 gtcacataca ccaccctgat cgacggcctg tgcaaggccg gcaaggtgga tgaggccctg    1380
gagctgttcg acgagatgaa ggagaggggc atcaagcccg acgtggttac atacaacacc    1440
ctgatcgacg gcctgtgcaa gagcggcaag atcgaggagg ccctgaagct gttcaaggag    1500
atggaggaga aggcatcac ccccagcgtg gtcacataca ccacactgat cgacggactg     1560
tgtaaagccg gcgacgtgga cgaagccctc gagctgttca aagagatgcg gagcaagggc    1620
gtgaagccca cgtggtgac atacaccacc ctgatcgacg gcctgtgcaa ggccggcaaa     1680
gtggacgagg ccctggagct gttcgacgag atgaaggaga ggggcatcaa gcccgacgtg    1740
gtcacataca acaccctgat cgacggcctg tgcaagagcg gcaagatcga ggaggccctg    1800
aagctgttca aggagatgga ggagaagggc atcacccca gcgtggttac atacaccaca     1860
ctgatcgacg gactgtgtaa agccggcgac gtggacgaag ccctcgagct gttcaaagag    1920
atgcggagca aggcgtgaa gcccaacgtg gtcacataca ccaccctgat cgacggcctg     1980
tgcaaggccg gcaaggtgga tgaggccctg gagctgttcg acgagatgaa ggagaggggc    2040
atcaagcccg acgtggtcac atacaacacc ctgatcgacg gcctgtgcaa gagcggcaag    2100
atcgaggagg ccctgaagct gttcaaggag atggaggaga agggcatcac ccccagcgtg    2160
gtcacataca ccacactgat cgacggactg tgtaaagccg gcgacgtgga cgaagccctc    2220
gagctgttca aagagatgcg gagcaagggc gtgaagccca cgtggttac atacaccacc     2280 ctgatcgacg gcctgtgcaa ggccggcaaa gtggacgagg ccctggagct gttcgacgag    2340
atgaaggaga ggggcatcaa gcccgacgtg gtcacataca acaccctgat cgacggcctg    2400
tgcaagagcg gcaagatcga ggaggccctg aagctgttca aggagatgga ggagaagggc    2460 atcacccca gcgtggtgac atacaccaca ctgatcgacg gactgtgtaa agccggcgac     2520
gtggacgaag ccctcgagct gttcaaagag atgcggagca agggcgtgaa gcccaacgtg    2580
```

```
gtcacataca ccaccctgat cgacggcctg tgcaaggccg gcaaggtgga tgaggccctg      2640
gagctgttcg acgagatgaa ggagaggggc atcaagcccg acgagctgac ctacaacacc      2700
ctgatcagcg gcctgggcaa ggccggcaga gccagagacc cccccgtgct cagtagcggg      2760
gactataagg accacgacgg agactacaag gatcatgata ttgattacaa agacgatgac      2820
gataagatgg ccggacgcta gmagvskgtg vvvdgdvngh ksvsgggdat ygktkcttgk      2880
vwtvtttygv csrydhmkhd ksamgyvrtk ddgnyktrav kgdtvnrkgd kdgnghkyny      2940
nshnvymadk kngkvnkrhn dgsvadhynt gdgvdnhyst saskdnkrdh mvvtaagtgm      3000
dykkkkrkvs hgsggsgggh mgnsvvtynt ndkcksgkak kmkgtsvvty ttdgckagdv      3060
dakmrskgvk nvvtyttdgc kagkvdadmk rgkdvvtynt dgcksgkakk mkgtsvvtyt      3120
tdgckagdvd akmrskgvkn vvtyttdgck agkvdadmkr gkdvvtyntd gcksgkakkm      3180
kgtsvvtytt dgckagdvda kmrskgvknv vtyttdgcka gkvdadmkrg kdvvtyntdg      3240
cksgkakkmk gtsvvtyttd gckagdvdak mrskgvknvv tyttdgckag kvdadmkrgk      3300
dvvtyntdgc ksgkakkmkg tsvvtyttdg ckagdvdakm rskgvknvvt yttdgckagk      3360
vdadmkrgkd vvtyntdgck sgkakkmkgt svvtyttdgc kagdvdakmr skgvknvvty      3420
ttdgckagkv dadmkrgkdt yntsggkagr ardvssgdyk dhdgdykdhd dykddddkma      3480 gr                                                                       3482
```

```
<210> SEQ ID NO 22
<211> LENGTH: 3482
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2858)..(2858)
<223> OTHER INFORMATION: n is a, c, g, t or u
<220> FEATURE:
<221> NAME/KEY: misc_feature
<222> LOCATION: (2914)..(2914)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2934)..(2934)
<223> OTHER INFORMATION: n is a, c, g, t or u
<220> FEATURE:
<221> NAME/KEY: misc_feature
<222> LOCATION: (2939)..(2939)
<223> OTHER INFORMATION: n is a, c, g, t or u
<220> FEATURE:
<221> NAME/KEY: misc_feature
<222> LOCATION: (2941)..(2941)
<223> OTHER INFORMATION: n is a, c, g, t or u
<220> FEATURE:
<221> NAME/KEY: misc_feature
<222> LOCATION: (2944)..(2944)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2956)..(2956)
<223> OTHER INFORMATION: n is a, c, g, t or u
<220> FEATURE:
<221> NAME/KEY: misc_feature
<222> LOCATION: (2960)..(2960)
<223> OTHER INFORMATION: n is a, c, g, t or u
```

```
<220> FEATURE:
<221> NAME/KEY: misc_feature
<222> LOCATION: (2969)..(2969)
<223> OTHER INFORMATION: n is a, c, g, t or u
<220> FEATURE:
<221> NAME/KEY: misc_feature
<222> LOCATION: (2976)..(2976)
<223> OTHER INFORMATION: n is a, c, g, t or u
<220> FEATURE:
<221> NAME/KEY: misc_feature
<222> LOCATION: (2986)..(2986)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3029)..(3029)
<223> OTHER INFORMATION: n is a, c, g, t or u
<220> FEATURE:
<221> NAME/KEY: misc_feature
<222> LOCATION: (3071)..(3071)
<223> OTHER INFORMATION: n is a, c, g, t or u
<220> FEATURE:
<221> NAME/KEY: misc_feature
<222> LOCATION: (3099)..(3099)
<223> OTHER INFORMATION: n is a, c, g, t or u
<220> FEATURE:
<221> NAME/KEY: misc_feature
<222> LOCATION: (3140)..(3140)
<223> OTHER INFORMATION: n is a, c, g, t or u
<220> FEATURE:
<221> NAME/KEY: misc_feature
<222> LOCATION: (3168)..(3168)
<223> OTHER INFORMATION: n is a, c, g, t or u
<220> FEATURE:
<221> NAME/KEY: misc_feature
<222> LOCATION: (3209)..(3209)
<223> OTHER INFORMATION: n is a, c, g, t or u
<220> FEATURE:
<221> NAME/KEY: misc_feature
<222> LOCATION: (3237)..(3237)
<223> OTHER INFORMATION: n is a, c, g, t or u
<220> FEATURE:
<221> NAME/KEY: misc_feature
<222> LOCATION: (3278)..(3278)
<223> OTHER INFORMATION: n is a, c, g, t or u
<220> FEATURE:
<221> NAME/KEY: misc_feature
<222> LOCATION: (3306)..(3306)
<223> OTHER INFORMATION: n is a, c, g, t or u
<220> FEATURE:
<221> NAME/KEY: misc_feature
<222> LOCATION: (3347)..(3347)
<223> OTHER INFORMATION: n is a, c, g, t or u
<220> FEATURE:
<221> NAME/KEY: misc_feature
<222> LOCATION: (3375)..(3375)
<223> OTHER INFORMATION: n is a, c, g, t or u
<220> FEATURE:
<221> NAME/KEY: misc_feature
<222> LOCATION: (3416)..(3416)
<223> OTHER INFORMATION: n is a, c, g, t or u
<220> FEATURE:
<221> NAME/KEY: misc_feature
<222> LOCATION: (3442)..(3442)
<223> OTHER INFORMATION: n is a, c, g, t or u

<400> SEQUENCE: 22
atggccggag tgagcaaggg cgaggagctg ttcaccgggg tggtgcccat cctggtcgag        60
ctggacggcg acgtaaacgg ccacaagttc agcgtgtccg gcgagggcga gggcgatgcc       120
acctacggca agctgaccct gaagttcatc tgcaccaccg gcaagctgcc cgtgccctgg       180
cccaccctcg tgaccaccct gacctacggc gtgcagtgct tcagccgcta ccccgaccac       240
```

-continued

```
atgaagcagc acgacttctt caagtccgcc atgcccgaag gctacgtcca ggagcgcacc      300
atcttcttca aggacgacgg caactacaag acccgcgccg aggtgaagtt cgagggcgac      360
accctggtga accgcatcga gctgaagggc atcgacttca aggaggacgg caacatcctg      420
gggcacaagc tggagtacaa ctacaacagc cacaacgtct atatcatggc cgacaagcag      480
aagaacggca tcaaggtgaa cttcaagatc cgccacaaca tcgaggacgg cagcgtgcag      540
ctcgccgacc actaccagca gaacaccccc atcggcgacg gccccgtgct gctgcccgac      600
aaccactacc tgagcaccca gtccgccctg agcaaagacc ccaacgagaa gcgcgatcac      660
atggtcctgc tggagttcgt gaccgccgcc gggatcactc tcggcatgga cgagctgtac      720
aagccaaaga aaaagagaaa ggttagccat ggctccggcg gcagcggggg agggctccat      780
atgggaaact ccgtggtcac atacaacacc gatatcgacg gcctgtgcaa gagcggcaag      840
atcgaggagg ccctgaagct gttcaaggag atggaggaga agggcatcac ccccagcgtg      900
gtcacataca ccacactgat cgacggactg tgtaaagccg gcgacgtgga cgaagccctc      960
gagctgttca aagagatgcg gagcaagggc gtgaagccca cgtggtgac atacaccacc     1020 ctgatcgacg gcctgtgcaa ggccggcaaa gtggacgagg ccctggagct gttcgacgag     1080
atgaaggaga ggggcatcaa gcccgacgtg gtcacataca acaccctgat cgacggcctg     1140
tgcaagagcg gcaagatcga ggaggccctg aagctgttca aggagatgga ggagaagggc     1200 atcacccccca gcgtggttac atacaccaca ctgatcgacg gactgtgtaa agccggcgac     1260
gtggacgaag ccctcgagct gttcaaagag atgcggagca agggcgtgaa gcccaacgtg     1320
gtcacataca ccaccctgat cgacggcctg tgcaaggccg gcaaggtgga tgaggccctg     1380
gagctgttcg acgagatgaa ggagaggggc atcaagcccg acgtggttac atacaacacc     1440
ctgatcgacg gcctgtgcaa gagcggcaag atcgaggagg ccctgaagct gttcaaggag     1500
atggaggaga agggcatcac ccccagcgtg gtcacataca ccacactgat cgacggactg     1560
tgtaaagccg gcgacgtgga cgaagccctc gagctgttca aagagatgcg gagcaagggc     1620
gtgaagccca cgtggtgac atacaccacc ctgatcgacg gcctgtgcaa ggccggcaaa     1680
gtggacgagg ccctggagct gttcgacgag atgaaggaga ggggcatcaa gcccgacgtg     1740
gtcacataca acaccctgat cgacggcctg tgcaagagcg gcaagatcga ggaggccctg     1800
aagctgttca aggagatgga ggagaagggc atcacccccca gcgtggttac atacaccaca     1860
ctgatcgacg gactgtgtaa agccggcgac gtggacgaag ccctcgagct gttcaaagag     1920
atgcggagca agggcgtgaa gcccaacgtg gtcacataca ccaccctgat cgacggcctg     1980
tgcaaggccg gcaaggtgga tgaggccctg gagctgttcg acgagatgaa ggagaggggc     2040
atcaagcccg acgtggtcac atacaacacc ctgatcgacg gcctgtgcaa gagcggcaag     2100
atcgaggagg ccctgaagct gttcaaggag atggaggaga agggcatcac ccccagcgtg     2160
gtcacataca ccacactgat cgacggactg tgtaaagccg gcgacgtgga cgaagccctc     2220
gagctgttca aagagatgcg gagcaagggc gtgaagccca cgtggttac atacaccacc     2280 ctgatcgacg gcctgtgcaa ggccggcaaa gtggacgagg ccctggagct gttcgacgag     2340
atgaaggaga ggggcatcaa gcccgacgtg gtcacataca acaccctgat cgacggcctg     2400
tgcaagagcg gcaagatcga ggaggccctg aagctgttca aggagatgga ggagaagggc     2460 atcacccccca gcgtggtgac atacaccaca ctgatcgacg gactgtgtaa agccggcgac     2520
gtggacgaag ccctcgagct gttcaaagag atgcggagca agggcgtgaa gcccaacgtg     2580
gtcacataca ccaccctgat cgacggcctg tgcaaggccg gcaaggtgga tgaggccctg     2640
```

-continued

```
gagctgttcg acgagatgaa ggagaggggc atcaagcccg acgagctgac ctacaacacc      2700
ctgatcagcg gcctgggcaa ggccggcaga gccagagacc cccccgtgct cagtagcggg      2760
gactataagg accacgacgg agactacaag gatcatgata ttgattacaa agacgatgac      2820
gataagatgg ccggacgcta gmagvskgtg vvvdgdvngh ksvsgggdat ygktkcttgk      2880
vwtvtttygv csrydhmkhd ksamgyvrtk ddgnyktrav kgdtvnrkgd kdgnghkyny      2940
nshnvymadk kngkvnkrhn dgsvadhynt gdgvdnhyst saskdnkrdh mvvtaagtgm      3000
dykkkkrkvs hgsggsgggh mgnsvvtynt ddgcksgkak kmkgtsvvty ttdgckagdv      3060
dakmrskgvk nvvtyttdgc kagkvdadmk rgkdvvtynt dgcksgkakk mkgtsvvtyt      3120
tdgckagdvd akmrskgvkn vvtyttdgck agkvdadmkr gkdvvtyntd gcksgkakkm      3180
kgtsvvtytt dgckagdvda kmrskgvknv vtyttdgcka gkvdadmkrg kdvvtyntdg      3240
cksgkakkmk gtsvvtyttd gckagdvdak mrskgvknvv tyttdgckag kvdadmkrgk      3300
dvvtyntdgc ksgkakkmkg tsvvtyttdg ckagdvdakm rskgvknvvt yttdgckagk      3360
vdadmkrgkd vvtyntdgck sgkakkmkgt svvtyttdgc kagdvdakmr skgvknvvty      3420
ttdgckagkv dadmkrgkdt yntsggkagr ardvssgdyk dhdgdykdhd dykddddkma      3480 gr                                                                    3482
```

```
<210> SEQ ID NO 23
<211> LENGTH: 3551
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2912)..(2912)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2982)..(2982)
<223> OTHER INFORMATION: n is a, c, g, t or u
<220> FEATURE:
<221> NAME/KEY: misc_feature
<222> LOCATION: (2990)..(2990)
<223> OTHER INFORMATION: n is a, c, g, t or u
<220> FEATURE:
<221> NAME/KEY: misc_feature
<222> LOCATION: (2995)..(2996)
<223> OTHER INFORMATION: n is a, c, g, t or u
<220> FEATURE:
<221> NAME/KEY: misc_feature
<222> LOCATION: (3007)..(3007)
<223> OTHER INFORMATION: n is a, c, g, t or u
<220> FEATURE:
<221> NAME/KEY: misc_feature
<222> LOCATION: (3011)..(3011)
<223> OTHER INFORMATION: n is a, c, g, t or u
<220> FEATURE:
<221> NAME/KEY: misc_feature
<222> LOCATION: (3015)..(3015)
<223> OTHER INFORMATION: n is a, c, g, t or u
<220> FEATURE:
<221> NAME/KEY: misc_feature
<222> LOCATION: (3025)..(3025)
<223> OTHER INFORMATION: n is a, c, g, t or u
<220> FEATURE:
<221> NAME/KEY: misc_feature
<222> LOCATION: (3032)..(3032)
<223> OTHER INFORMATION: n is a, c, g, t or u
<220> FEATURE:
```

-continued

```
<221> NAME/KEY: misc_feature
<222> LOCATION: (3042)..(3042)
<223> OTHER INFORMATION: n is a, c, g, t or u
<220> FEATURE:
<221> NAME/KEY: misc_feature
<222> LOCATION: (3066)..(3066)
<223> OTHER INFORMATION: n is a, c, g, t or u
<220> FEATURE:
<221> NAME/KEY: misc_feature
<222> LOCATION: (3072)..(3072)
<223> OTHER INFORMATION: n is a, c, g, t or u
<220> FEATURE:
<221> NAME/KEY: misc_feature
<222> LOCATION: (3113)..(3113)
<223> OTHER INFORMATION: n is a, c, g, t or u
<220> FEATURE:
<221> NAME/KEY: misc_feature
<222> LOCATION: (3141)..(3141)
<223> OTHER INFORMATION: n is a, c, g, t or u
<220> FEATURE:
<221> NAME/KEY: misc_feature
<222> LOCATION: (3182)..(3182)
<223> OTHER INFORMATION: n is a, c, g, t or u
<220> FEATURE:
<221> NAME/KEY: misc_feature
<222> LOCATION: (3210)..(3210)
<223> OTHER INFORMATION: n is a, c, g, t or u
<220> FEATURE:
<221> NAME/KEY: misc_feature
<222> LOCATION: (3251)..(3251)
<223> OTHER INFORMATION: n is a, c, g, t or u
<220> FEATURE:
<221> NAME/KEY: misc_feature
<222> LOCATION: (3279)..(3279)
<223> OTHER INFORMATION: n is a, c, g, t or u
<220> FEATURE:
<221> NAME/KEY: misc_feature
<222> LOCATION: (3320)..(3320)
<223> OTHER INFORMATION: n is a, c, g, t or u
<220> FEATURE:
<221> NAME/KEY: misc_feature
<222> LOCATION: (3348)..(3348)
<223> OTHER INFORMATION: n is a, c, g, t or u
<220> FEATURE:
<221> NAME/KEY: misc_feature
<222> LOCATION: (3389)..(3389)
<223> OTHER INFORMATION: n is a, c, g, t or u
<220> FEATURE:
<221> NAME/KEY: misc_feature
<222> LOCATION: (3417)..(3417)
<223> OTHER INFORMATION: n is a, c, g, t or u
<220> FEATURE:
<221> NAME/KEY: misc_feature
<222> LOCATION: (3458)..(3458)
<223> OTHER INFORMATION: n is a, c, g, t or u
<220> FEATURE:
<221> NAME/KEY: misc_feature
<222> LOCATION: (3484)..(3484)
<223> OTHER INFORMATION: n is a, c, g, t or u

<400> SEQUENCE: 23
atggccggag tgtccaaagg cgaggagctg tttaccggcg tcgtgcctat tctggtggag        60
ctggacggcg acgtgaacgg ccacaagttc tccgtgaggg gcgagggcga aggcgatgcc       120
acaaacggca agctgaccct caagttcatc tgcaccactg gtaaactgcc cgttccttgg       180
cccacactgg tgaccacctt cggctacggc gtggcttgtt tctctcgtta ccccgaccat       240
atgaagcagc acgacttctt caagtccgcc atgcccgagg gatacgtgca agaaaggacc       300
atctccttca aggacgatgg cacctacaag accagagccg aggtgaagtt cgagggcgac       360
acactggtga atcgtatcga actgaagggc atcgacttca agaggacggg caacattctg       420
ggccacaagc tggagtacaa cttcaacagc cactacgtgt acatcaccgc cgataagcag       480
aagaactgca tcaaggccaa cttcaagatt cgtcacaacg tggaggatgg ctccgtgcag       540
```

-continued

```
ctggccgatc actaccagca gaacacaccc atcggcgatg gacccgtttt actgcccgac      600
aaccactatt taagccacca gagcaagctg tccaaggacc ccaacgagaa gcgtgatcat      660
atggtgctgc tcgagtttgt gaccgccgcc ggcatcaccc atggaatgga cgagctgtac      720
aagagccggc tccatatggg aaactccgtg gtcacataca acaccctgat cgacggcctg      780
tgcaagagcg gcaagatcga ggaggccctg aagctgttca aggagatgga ggagaagggc      840
atcaccccca gcgtggtcac atacaccaca ctgatcgacg gactgtgtaa agccggcgac      900
gtggacgaag ccctcgagct gttcaaagag atgcggagca agggcgtgaa gcccaacgtg      960
gtgacataca ccaccctgat cgacggcctg tgcaaggccg gcaaagtgga cgaggccctg     1020
gagctgttcg acgagatgaa ggagaggggc atcaagcccg acgtggtcac atacaacacc     1080
ctgatcgacg gcctgtgcaa gagcggcaag atcgaggagg ccctgaagct gttcaaggag     1140
atggaggaga agggcatcac ccccagcgtg gttacataca ccacactgat cgacggactg     1200
tgtaaagccg gcgacgtgga cgaagccctc gagctgttca agagatgcg gagcaagggc      1260 gtgaagccca acgtggtcac atacaccacc ctgatcgacg gcctgtgcaa ggccggcaag     1320
gtggatgagg ccctggagct gttcgacgag atgaaggaga ggggcatcaa gcccgacgtg     1380
gttacataca acaccctgat cgacggcctg tgcaagagcg gcaagatcga ggaggccctg     1440
aagctgttca aggagatgga ggagaagggc atcaccccca gcgtggtcac atacaccaca     1500
ctgatcgacg gactgtgtaa agccggcgac gtggacgaag ccctcgagct gttcaaagag     1560
atgcggagca agggcgtgaa gcccaacgtg gtgacataca ccaccctgat cgacggcctg     1620
tgcaaggccg gcaaagtgga cgaggccctg gagctgttcg acgagatgaa ggagaggggc     1680
atcaagcccg acgtggtcac atacaacacc ctgatcgacg gcctgtgcaa gagcggcaag     1740
atcgaggagg ccctgaagct gttcaaggag atggaggaga agggcatcac ccccagcgtg     1800
gttacataca ccacactgat cgacggactg tgtaaagccg gcgacgtgga cgaagccctc     1860
gagctgttca aagagatgcg gagcaagggc gtgaagccca acgtggtcac atacaccacc     1920
ctgatcgacg gcctgtgcaa ggccggcaag gtggatgagg ccctggagct gttcgacgag     1980
atgaaggaga ggggcatcaa gcccgacgtg gtcacataca acaccctgat cgacggcctg     2040
tgcaagagcg gcaagatcga ggaggccctg aagctgttca aggagatgga ggagaagggc     2100
atcaccccca gcgtggtcac atacaccaca ctgatcgacg gactgtgtaa agccggcgac     2160
gtggacgaag ccctcgagct gttcaaagag atgcggagca agggcgtgaa gcccaacgtg     2220
gttacataca ccaccctgat cgacggcctg tgcaaggccg gcaaagtgga cgaggccctg     2280
gagctgttcg acgagatgaa ggagaggggc atcaagcccg acgtggtcac atacaacacc     2340
ctgatcgacg gcctgtgcaa gagcggcaag atcgaggagg ccctgaagct gttcaaggag     2400
atggaggaga agggcatcac ccccagcgtg gtgacataca ccacactgat cgacggactg     2460
tgtaaagccg gcgacgtgga cgaagccctc gagctgttca aagagatgcg gagcaagggc     2520
gtgaagccca acgtggtcac atacaccacc ctgatcgacg gcctgtgcaa ggccggcaag     2580
gtggatgagg ccctggagct gttcgacgag atgaaggaga ggggcatcaa gcccgacgag     2640
ctgacctaca cacccctgat cagcggcctg ggcaaggccg gcagagccag agaccccccc     2700
gtgctcagta gccccaagaa gaaacgcaaa gtcgaggatc caaagaagaa aaggaaggtt     2760
gaagacccca agaaaaagag gaaggtgggt tccgactata aggaccacga cggagactac     2820
aaggatcatg atattgatta caaagacgat gacgataaga tggcccccaa agaagaagcgg     2880
```

```
aaggtcggac gctagmagvs kgtgvvvdgd vnghksvrgg gdatngktkc ttgkvwtvtt      2940
gygvacsryd hmkhdksamg yvrtskddgt yktravkgdt vnrkgdkdgn ghkynnshyv      3000
ytadkkncka nkrhnvdgsv adhyntgdgv dnhyshsksk dnkrdhmvvt aagthgmdyk      3060
srhmgnsvvt yntdgcksgk akkmkgtsvv tyttdgckag dvdakmrskg vknvvtyttd      3120
gckagkvdad mkrgkdvvty ntdgcksgka kkmkgtsvvt yttdgckagd vdakmrskgv      3180
knvvtyttdg ckagkvdadm krgkdvvtyn tdgcksgkak kmkgtsvvty ttdgckagdv      3240
dakmrskgvk nvvtyttdgc kagkvdadmk rgkdvvtynt dgcksgkakk mkgtsvvtyt      3300
tdgckagdvd akmrskgvkn vvtyttdgck agkvdadmkr gkdvvtyntd gcksgkakkm      3360
kgtsvvtytt dgckagdvda kmrskgvknv vtyttdgcka gkvdadmkrg kdvvtyntdg      3420
cksgkakkmk gtsvvtyttd gckagdvdak mrskgvknvv tyttdgckag kvdadmkrgk      3480
dtyntsggka grardvsskk krkvdkkkrk vdkkkrkvgs dykdhdgdyk dhddykdddd      3540
kmakkkrkvg r                                                          3551
```

```
<210> SEQ ID NO 24
<211> LENGTH: 3550
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2912)..(2912)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2982)..(2982)
<223> OTHER INFORMATION: n is a, c, g, t or u
<220> FEATURE:
<221> NAME/KEY: misc_feature
<222> LOCATION: (2990)..(2990)
<223> OTHER INFORMATION: n is a, c, g, t or u
<220> FEATURE:
<221> NAME/KEY: misc_feature
<222> LOCATION: (2995)..(2996)
<223> OTHER INFORMATION: n is a, c, g, t or u
<220> FEATURE:
<221> NAME/KEY: misc_feature
<222> LOCATION: (3007)..(3007)
<223> OTHER INFORMATION: n is a, c, g, t or u
<220> FEATURE:
<221> NAME/KEY: misc_feature
<222> LOCATION: (3011)..(3011)
<223> OTHER INFORMATION: n is a, c, g, t or u
<220> FEATURE:
<221> NAME/KEY: misc_feature
<222> LOCATION: (3015)..(3015)
<223> OTHER INFORMATION: n is a, c, g, t or u
<220> FEATURE:
<221> NAME/KEY: misc_feature
<222> LOCATION: (3025)..(3025)
<223> OTHER INFORMATION: n is a, c, g, t or u
<220> FEATURE:
<221> NAME/KEY: misc_feature
<222> LOCATION: (3032)..(3032)
<223> OTHER INFORMATION: n is a, c, g, t or u
<220> FEATURE:
<221> NAME/KEY: misc_feature
<222> LOCATION: (3042)..(3042)
<223> OTHER INFORMATION: n is a, c, g, t or u
<220> FEATURE:
<221> NAME/KEY: misc_feature
<222> LOCATION: (3066)..(3066)
<223> OTHER INFORMATION: n is a, c, g, t or u
```

```
<220> FEATURE:
<221> NAME/KEY: misc_feature
<222> LOCATION: (3072)..(3072)
<223> OTHER INFORMATION: n is a, c, g, t or u
<220> FEATURE:
<221> NAME/KEY: misc_feature
<222> LOCATION: (3112)..(3112)
<223> OTHER INFORMATION: n is a, c, g, t or u
<220> FEATURE:
<221> NAME/KEY: misc_feature
<222> LOCATION: (3140)..(3140)
<223> OTHER INFORMATION: n is a, c, g, t or u
<220> FEATURE:
<221> NAME/KEY: misc_feature
<222> LOCATION: (3181)..(3181)
<223> OTHER INFORMATION: n is a, c, g, t or u
<220> FEATURE:
<221> NAME/KEY: misc_feature
<222> LOCATION: (3209)..(3209)
<223> OTHER INFORMATION: n is a, c, g, t or u
<220> FEATURE:
<221> NAME/KEY: misc_feature
<222> LOCATION: (3250)..(3250)
<223> OTHER INFORMATION: n is a, c, g, t or u
<220> FEATURE:
<221> NAME/KEY: misc_feature
<222> LOCATION: (3278)..(3278)
<223> OTHER INFORMATION: n is a, c, g, t or u
<220> FEATURE:
<221> NAME/KEY: misc_feature
<222> LOCATION: (3319)..(3319)
<223> OTHER INFORMATION: n is a, c, g, t or u
<220> FEATURE:
<221> NAME/KEY: misc_feature
<222> LOCATION: (3347)..(3347)
<223> OTHER INFORMATION: n is a, c, g, t or u
<220> FEATURE:
<221> NAME/KEY: misc_feature
<222> LOCATION: (3388)..(3388)
<223> OTHER INFORMATION: n is a, c, g, t or u
<220> FEATURE:
<221> NAME/KEY: misc_feature
<222> LOCATION: (3416)..(3416)
<223> OTHER INFORMATION: n is a, c, g, t or u
<220> FEATURE:
<221> NAME/KEY: misc_feature
<222> LOCATION: (3457)..(3457)
<223> OTHER INFORMATION: n is a, c, g, t or u
<220> FEATURE:
<221> NAME/KEY: misc_feature
<222> LOCATION: (3483)..(3483)
<223> OTHER INFORMATION: n is a, c, g, t or u

<400> SEQUENCE: 24
atggccggag tgtccaaagg cgaggagctg tttaccggcg tcgtgcctat tctggtggag        60
ctggacggcg acgtgaacgg ccacaagttc tccgtgaggg gcgagggcga aggcgatgcc       120
acaaacggca agctgaccct caagttcatc tgcaccactg gtaaactgcc cgttccttgg       180
cccacactgg tgaccaccct cggctacggc gtggcttgtt tctctcgtta ccccgaccat       240
atgaagcagc acgacttctt caagtccgcc atgcccgagg gatacgtgca agaaaggacc       300
atctccttca aggacgatgg cacctacaag accagagccg aggtgaagtt cgagggcgac       360
acactggtga atcgtatcga actgaagggc atcgacttca agaggacgg caacattctg        420 ggccacaagc tggagtacaa cttcaacagc cactacgtgt acatcaccgc cgataagcag       480
aagaactgca tcaaggccaa cttcaagatt cgtcacaacg tggaggatgg ctccgtgcag       540
ctggccgatc actaccagca gaacacaccc atcggcgatg gacccgtttt actgcccgac       600
aaccactatt taagccacca gagcaagctg tccaaggacc ccaacgagaa gcgtgatcat       660
atggtgctgc tcgagtttgt gaccgccgcc ggcatcaccc atggaatgga cgagctgtac       720
```

-continued

```
aagagccggc tccatatggg aaactccgtg gtcacataca acaccctgat cgacgaactg      780
tgcaagagcg gcaagatcga ggaggccctg aagctgttca aggagatgga ggagaagggc      840
atcaccccca gcgtggtcac atacaccaca ctgatcgacg gactgtgtaa agccggcgac      900
gtggacgaag ccctcgagct gttcaaagag atgcggagca aggcgtgaa gcccaacgtg      960 gtgacataca ccaccctgat cgacggcctg tgcaaggccg gcaaagtgga cgaggccctg     1020
gagctgttcg acgagatgaa ggagaggggc atcaagcccg acgtggtcac atacaacacc     1080
ctgatcgacg gcctgtgcaa gagcggcaag atcgaggagg ccctgaagct gttcaaggag     1140
atggaggaga aggggcatcac ccccagcgtg gttacataca ccacactgat cgacggactg     1200
tgtaaagccg gcgacgtgga cgaagccctc gagctgttca aagagatgcg gagcaagggc     1260
gtgaagccca cgtggtcac atacaccacc ctgatcgacg gcctgtgcaa ggccggcaag     1320
gtggatgagg ccctggagct gttcgacgag atgaaggaga ggggcatcaa gcccgacgtg     1380
gttacataca acaccctgat cgacggcctg tgcaagagcg gcaagatcga ggaggccctg     1440
aagctgttca aggagatgga ggagaagggc atcaccccca gcgtggtcac atacaccaca     1500
ctgatcgacg gactgtgtaa agccggcgac gtggacgaag ccctcgagct gttcaaagag     1560
atgcggagca aggggcgtgaa gcccaacgtg gtgacataca ccaccctgat cgacggcctg     1620
tgcaaggccg gcaaagtgga cgaggccctg gagctgttcg acgagatgaa ggagaggggc     1680
atcaagcccg acgtggtcac atacaacacc ctgatcgacg gcctgtgcaa gagcggcaag     1740
atcgaggagg ccctgaagct gttcaaggag atggaggaga aggggcatcac ccccagcgtg     1800 gttacataca ccacactgat cgacggactg tgtaaagccg gcgacgtgga cgaagccctc     1860
gagctgttca aagagatgcg gagcaagggc gtgaagccca cgtggtcac atacaccacc     1920 ctgatcgacg gcctgtgcaa ggccggcaag gtggatgagg ccctggagct gttcgacgag     1980
atgaaggaga ggggcatcaa gcccgacgtg gtcacataca acaccctgat cgacggcctg     2040
tgcaagagcg gcaagatcga ggaggccctg aagctgttca aggagatgga ggagaagggc     2100
atcaccccca gcgtggtcac atacaccaca ctgatcgacg gactgtgtaa agccggcgac     2160
gtggacgaag ccctcgagct gttcaaagag atgcggagca aggcgtgaa gcccaacgtg     2220 gttacataca ccaccctgat cgacggcctg tgcaaggccg gcaaagtgga cgaggccctg     2280
gagctgttcg acgagatgaa ggagaggggc atcaagcccg acgtggtcac atacaacacc     2340
ctgatcgacg gcctgtgcaa gagcggcaag atcgaggagg ccctgaagct gttcaaggag     2400
atggaggaga aggggcatcac ccccagcgtg gtgacataca ccacactgat cgacggactg     2460
tgtaaagccg gcgacgtgga cgaagccctc gagctgttca aagagatgcg gagcaagggc     2520
gtgaagccca cgtggtcac atacaccacc ctgatcgacg gcctgtgcaa ggccggcaag     2580
gtggatgagg ccctggagct gttcgacgag atgaaggaga ggggcatcaa gcccgacgag     2640
ctgacctaca acaccctgat cagcggcctg ggcaaggccg gcagagccag agaccccccc     2700
gtgctcagta gccccaagaa gaaacgcaaa gtcgaggatc caaagaagaa aaggaaggtt     2760
gaagacccca agaaaaagag gaaggtgggt tccgactata aggaccacga cggagactac     2820
aaggatcatg atattgatta caaagacgat gacgataaga tggcccccaaa gaagaagcgg     2880 aaggtcggac gctagmagvs kgtgvvvdgd vnghksvrgg gdatngktkc ttgkvwtvtt     2940
gygvacsryd hmkhdksamg yvrtskddgt yktravkgdt vnrkgdkdgn ghkynnshyv     3000
ytadkkncka nkrhnvdgsv adhyntgdgv dnhyshsksk dnkrdhmvvt aagthgmdyk     3060
srhmgnsvvt yntdcksgka kkmkgtsvvt yttdgckagd vdakmrskgv knvvtyttdg     3120
```

```
ckagkvdadm krgkdvvtyn tdgcksgkak kmkgtsvvty ttdgckagdv dakmrskgvk        3180
nvvtyttdgc kagkvdadmk rgkdvvtynt dgcksgkakk mkgtsvvtyt tdgckagdvd        3240
akmrskgvkn vvtyttdgck agkvdadmkr gkdvvtyntd gcksgkakkm kgtsvvtytt        3300
dgckagdvda kmrskgvknv vtyttdgcka gkvdadmkrg kdvvtyntdg cksgkakkmk        3360
gtsvvtyttd gckagdvdak mrskgvknvv tyttdgckag kvdadmkrgk dvvtyntdgc        3420
ksgkakkmkg tsvvtyttdg ckagdvdakm rskgvknvvt yttdgckagk vdadmkrgkd        3480
tyntsggkag rardvsskkk rkvdkkkrkv dkkkrkvgsd ykdhdgdykd hddykdddk         3540 makkkrkvgr                                                              3550
```

```
<210> SEQ ID NO 25
<211> LENGTH: 3551
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2912)..(2912)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2982)..(2982)
<223> OTHER INFORMATION: n is a, c, g, t or u
<220> FEATURE:
<221> NAME/KEY: misc_feature
<222> LOCATION: (2990)..(2990)
<223> OTHER INFORMATION: n is a, c, g, t or u
<220> FEATURE:
<221> NAME/KEY: misc_feature
<222> LOCATION: (2995)..(2996)
<223> OTHER INFORMATION: n is a, c, g, t or u
<220> FEATURE:
<221> NAME/KEY: misc_feature
<222> LOCATION: (3007)..(3007)
<223> OTHER INFORMATION: n is a, c, g, t or u
<220> FEATURE:
<221> NAME/KEY: misc_feature
<222> LOCATION: (3011)..(3011)
<223> OTHER INFORMATION: n is a, c, g, t or u
<220> FEATURE:
<221> NAME/KEY: misc_feature
<222> LOCATION: (3015)..(3015)
<223> OTHER INFORMATION: n is a, c, g, t or u
<220> FEATURE:
<221> NAME/KEY: misc_feature
<222> LOCATION: (3025)..(3025)
<223> OTHER INFORMATION: n is a, c, g, t or u
<220> FEATURE:
<221> NAME/KEY: misc_feature
<222> LOCATION: (3032)..(3032)
<223> OTHER INFORMATION: n is a, c, g, t or u
<220> FEATURE:
<221> NAME/KEY: misc_feature
<222> LOCATION: (3042)..(3042)
<223> OTHER INFORMATION: n is a, c, g, t or u
<220> FEATURE:
<221> NAME/KEY: misc_feature
<222> LOCATION: (3066)..(3066)
<223> OTHER INFORMATION: n is a, c, g, t or u
<220> FEATURE:
<221> NAME/KEY: misc_feature
<222> LOCATION: (3072)..(3072)
<223> OTHER INFORMATION: n is a, c, g, t or u
<220> FEATURE:
<221> NAME/KEY: misc_feature
<222> LOCATION: (3074)..(3074)
```

<223> OTHER INFORMATION: n is a, c, g, t or u
<220> FEATURE:
<221> NAME/KEY: misc_feature
<222> LOCATION: (3113)..(3113)
<223> OTHER INFORMATION: n is a, c, g, t or u
<220> FEATURE:
<221> NAME/KEY: misc_feature
<222> LOCATION: (3141)..(3141)
<223> OTHER INFORMATION: n is a, c, g, t or u
<220> FEATURE:
<221> NAME/KEY: misc_feature
<222> LOCATION: (3182)..(3182)
<223> OTHER INFORMATION: n is a, c, g, t or u
<220> FEATURE:
<221> NAME/KEY: misc_feature
<222> LOCATION: (3210)..(3210)
<223> OTHER INFORMATION: n is a, c, g, t or u
<220> FEATURE:
<221> NAME/KEY: misc_feature
<222> LOCATION: (3251)..(3251)
<223> OTHER INFORMATION: n is a, c, g, t or u
<220> FEATURE:
<221> NAME/KEY: misc_feature
<222> LOCATION: (3279)..(3279)
<223> OTHER INFORMATION: n is a, c, g, t or u
<220> FEATURE:
<221> NAME/KEY: misc_feature
<222> LOCATION: (3320)..(3320)
<223> OTHER INFORMATION: n is a, c, g, t or u
<220> FEATURE:
<221> NAME/KEY: misc_feature
<222> LOCATION: (3348)..(3348)
<223> OTHER INFORMATION: n is a, c, g, t or u
<220> FEATURE:
<221> NAME/KEY: misc_feature
<222> LOCATION: (3389)..(3389)
<223> OTHER INFORMATION: n is a, c, g, t or u
<220> FEATURE:
<221> NAME/KEY: misc_feature
<222> LOCATION: (3417)..(3417)
<223> OTHER INFORMATION: n is a, c, g, t or u
<220> FEATURE:
<221> NAME/KEY: misc_feature
<222> LOCATION: (3458)..(3458)
<223> OTHER INFORMATION: n is a, c, g, t or u
<220> FEATURE:
<221> NAME/KEY: misc_feature
<222> LOCATION: (3484)..(3484)
<223> OTHER INFORMATION: n is a, c, g, t or u

<400> SEQUENCE: 25
atggccggag tgtccaaagg cgaggagctg tttaccggcg tcgtgcctat tctggtggag        60
ctggacggcg acgtgaacgg ccacaagttc tccgtgaggg gcgagggcga aggcgatgcc       120
acaaacggca agctgaccct caagttcatc tgcaccactg gtaaactgcc cgttccttgg       180
cccacactgg tgaccacctt cggctacggc gtggcttgtt tctctcgtta ccccgaccat       240
atgaagcagc acgacttctt caagtccgcc atgcccgagg atacgtgca agaaaggacc        300 atctccttca aggacgatgg cacctacaag accagagccg aggtgaagtt cgagggcgac       360
acactggtga atcgtatcga actgaagggc atcgacttca agaggacggg caacattctg       420
ggccacaagc tggagtacaa cttcaacagc cactacgtgt acatcaccgc cgataagcag       480
aagaactgca tcaaggccaa cttcaagatt cgtcacaacg tggaggatgg ctccgtgcag       540
ctggccgatc actaccagca gaacacaccc atcggcgatg acccgtttt actgcccgac        600 aaccactatt taagccacca gagcaagctg tccaaggacc ccaacgagaa gcgtgatcat       660
atggtgctgc tcgagtttgt gaccgccgcc ggcatcaccc atggaatgga cgagctgtac       720
aagagccggc tccatatggg aaactccgtg gtcacataca acaccaacat cgaccagctg       780
tgcaagagcg gcaagatcga ggaggccctg aagctgttca aggagatgga ggagaagggc       840

```
atcaccccca gcgtggtcac atacaccaca ctgatcgacg gactgtgtaa agccggcgac      900
gtggacgaag ccctcgagct gttcaaagag atgcggagca agggcgtgaa gcccaacgtg      960
gtgacataca ccaccctgat cgacggcctg tgcaaggccg gcaaagtgga cgaggccctg     1020
gagctgttcg acgagatgaa ggagaggggc atcaagcccg acgtggtcac atacaacacc     1080
ctgatcgacg gcctgtgcaa gagcggcaag atcgaggagg ccctgaagct gttcaaggag     1140
atggaggaga agggcatcac ccccagcgtg gttacataca ccacactgat cgacggactg     1200
tgtaaagccg gcgacgtgga cgaagccctc gagctgttca aagagatgcg gagcaagggc     1260
gtgaagccca acgtggtcac ataccacc ctgatcgacg gcctgtgcaa ggccggcaag     1320
gtggatgagg ccctggagct gttcgacgag atgaaggaga ggggcatcaa gcccgacgtg     1380
gttacataca acaccctgat cgacggcctg tgcaagagcg gcaagatcga ggaggccctg     1440
aagctgttca aggagatgga ggagaagggc atcaccccca gcgtggtcac atacaccaca     1500
ctgatcgacg gactgtgtaa agccggcgac gtggacgaag ccctcgagct gttcaaagag     1560
atgcggagca agggcgtgaa gcccaacgtg gtgacataca ccaccctgat cgacggcctg     1620
tgcaaggccg gcaaagtgga cgaggccctg gagctgttcg acgagatgaa ggagaggggc     1680
atcaagcccg acgtggtcac atacaacacc ctgatcgacg gcctgtgcaa gagcggcaag     1740
atcgaggagg ccctgaagct gttcaaggag atggaggaga agggcatcac ccccagcgtg     1800
gttacataca ccacactgat cgacggactg tgtaaagccg gcgacgtgga cgaagccctc     1860
gagctgttca aagagatgcg gagcaagggc gtgaagccca acgtggtcac ataccacc     1920 ctgatcgacg gcctgtgcaa ggccggcaag gtggatgagg ccctggagct gttcgacgag     1980
atgaaggaga ggggcatcaa gcccgacgtg gtcacataca acaccctgat cgacggcctg     2040
tgcaagagcg gcaagatcga ggaggccctg aagctgttca aggagatgga ggagaagggc     2100
atcaccccca gcgtggtcac atacaccaca ctgatcgacg gactgtgtaa agccggcgac     2160
gtggacgaag ccctcgagct gttcaaagag atgcggagca agggcgtgaa gcccaacgtg     2220
gttacataca ccaccctgat cgacggcctg tgcaaggccg gcaaagtgga cgaggccctg     2280
gagctgttcg acgagatgaa ggagaggggc atcaagcccg acgtggtcac atacaacacc     2340
ctgatcgacg gcctgtgcaa gagcggcaag atcgaggagg ccctgaagct gttcaaggag     2400
atggaggaga agggcatcac ccccagcgtg gtgacataca ccacactgat cgacggactg     2460
tgtaaagccg gcgacgtgga cgaagccctc gagctgttca aagagatgcg gagcaagggc     2520
gtgaagccca acgtggtcac ataccacc ctgatcgacg gcctgtgcaa ggccggcaag     2580
gtggatgagg ccctggagct gttcgacgag atgaaggaga ggggcatcaa gcccgacgag     2640
ctgacctaca cacccctgat cagcggcctg ggcaaggccg gcagagccag agacccccc     2700 gtgctcagta gccccaagaa gaaacgcaaa gtcgaggatc caaagaagaa aaggaaggtt     2760
gaagacccca agaaaaagag gaaggtgggt tccgactata aggaccacga cggagactac     2820
aaggatcatg atattgatta caaagacgat gacgataaga tggccccaaa gaagaagcgg     2880
aaggtcggac gctagcmagvs kgtgvvvdgd vnghksvrgg gdatngktkc ttgkvwtvtt     2940
gygvacsryd hmkhdksamg yvrtskddgt yktravkgdt vnrkgdkdgn ghkynnshyv     3000
ytadkkncka nkrhnvdgsv adhyntgdgv dnhyshsksk dnkrdhmvvt aagthgmdyk     3060
srhmgnsvvt yntndcksgk akkmkgtsvv tyttdgckag dvdakmrskg vknvvtyttd     3120
gckagkvdad mkrgkdvvty ntdgcksgka kkmkgtsvvt yttdgckagd vdakmrskgv     3180
```

-continued

```
knvvtyttdg ckagkvdadm krgkdvvtyn tdgcksgkak kmkgtsvvty ttdgckagdv    3240
dakmrskgvk nvvtyttdgc kagkvdadmk rgkdvvtynt dgcksgkakk mkgtsvvtyt    3300
tdgckagdvd akmrskgvkn vvtyttdgck agkvdadmkr gkdvvtyntd gcksgkakkm    3360
kgtsvvtytt dgckagdvda kmrskgvknv vtyttdgcka gkvdadmkrg kdvvtyntdg    3420
cksgkakkmk gtsvvtyttd gckagdvdak mrskgvknvv tyttdgckag kvdadmkrgk    3480
dtyntsggka grardvsskk krkvdkkkrk vdkkkrkvgs dykdhdgdyk dhddykdddd    3540
kmakkkrkvg r                                                        3551
```

```
<210> SEQ ID NO 26
<211> LENGTH: 3551
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2912)..(2912)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2982)..(2982)
<223> OTHER INFORMATION: n is a, c, g, t or u
<220> FEATURE:
<221> NAME/KEY: misc_feature
<222> LOCATION: (2990)..(2990)
<223> OTHER INFORMATION: n is a, c, g, t or u
<220> FEATURE:
<221> NAME/KEY: misc_feature
<222> LOCATION: (2995)..(2996)
<223> OTHER INFORMATION: n is a, c, g, t or u
<220> FEATURE:
<221> NAME/KEY: misc_feature
<222> LOCATION: (3007)..(3007)
<223> OTHER INFORMATION: n is a, c, g, t or u
<220> FEATURE:
<221> NAME/KEY: misc_feature
<222> LOCATION: (3011)..(3011)
<223> OTHER INFORMATION: n is a, c, g, t or u
<220> FEATURE:
<221> NAME/KEY: misc_feature
<222> LOCATION: (3015)..(3015)
<223> OTHER INFORMATION: n is a, c, g, t or u
<220> FEATURE:
<221> NAME/KEY: misc_feature
<222> LOCATION: (3025)..(3025)
<223> OTHER INFORMATION: n is a, c, g, t or u
<220> FEATURE:
<221> NAME/KEY: misc_feature
<222> LOCATION: (3032)..(3032)
<223> OTHER INFORMATION: n is a, c, g, t or u
<220> FEATURE:
<221> NAME/KEY: misc_feature
<222> LOCATION: (3042)..(3042)
<223> OTHER INFORMATION: n is a, c, g, t or u
<220> FEATURE:
<221> NAME/KEY: misc_feature
<222> LOCATION: (3066)..(3066)
<223> OTHER INFORMATION: n is a, c, g, t or u
<220> FEATURE:
<221> NAME/KEY: misc_feature
<222> LOCATION: (3072)..(3072)
<223> OTHER INFORMATION: n is a, c, g, t or u
<220> FEATURE:
<221> NAME/KEY: misc_feature
<222> LOCATION: (3074)..(3074)
<223> OTHER INFORMATION: n is a, c, g, t or u
<220> FEATURE:
<221> NAME/KEY: misc_feature
```

-continued

```
<222> LOCATION: (3113)..(3113)
<223> OTHER INFORMATION: n is a, c, g, t or u
<220> FEATURE:
<221> NAME/KEY: misc_feature
<222> LOCATION: (3141)..(3141)
<223> OTHER INFORMATION: n is a, c, g, t or u
<220> FEATURE:
<221> NAME/KEY: misc_feature
<222> LOCATION: (3182)..(3182)
<223> OTHER INFORMATION: n is a, c, g, t or u
<220> FEATURE:
<221> NAME/KEY: misc_feature
<222> LOCATION: (3210)..(3210)
<223> OTHER INFORMATION: n is a, c, g, t or u
<220> FEATURE:
<221> NAME/KEY: misc_feature
<222> LOCATION: (3251)..(3251)
<223> OTHER INFORMATION: n is a, c, g, t or u
<220> FEATURE:
<221> NAME/KEY: misc_feature
<222> LOCATION: (3279)..(3279)
<223> OTHER INFORMATION: n is a, c, g, t or u
<220> FEATURE:
<221> NAME/KEY: misc_feature
<222> LOCATION: (3320)..(3320)
<223> OTHER INFORMATION: n is a, c, g, t or u
<220> FEATURE:
<221> NAME/KEY: misc_feature
<222> LOCATION: (3348)..(3348)
<223> OTHER INFORMATION: n is a, c, g, t or u
<220> FEATURE:
<221> NAME/KEY: misc_feature
<222> LOCATION: (3389)..(3389)
<223> OTHER INFORMATION: n is a, c, g, t or u
<220> FEATURE:
<221> NAME/KEY: misc_feature
<222> LOCATION: (3417)..(3417)
<223> OTHER INFORMATION: n is a, c, g, t or u
<220> FEATURE:
<221> NAME/KEY: misc_feature
<222> LOCATION: (3458)..(3458)
<223> OTHER INFORMATION: n is a, c, g, t or u
<220> FEATURE:
<221> NAME/KEY: misc_feature
<222> LOCATION: (3484)..(3484)
<223> OTHER INFORMATION: n is a, c, g, t or u

<400> SEQUENCE: 26
atggccggag tgtccaaagg cgaggagctg tttaccggcg tcgtgcctat tctggtggag      60
ctggacggcg acgtgaacgg ccacaagttc tccgtgaggg gcgagggcga aggcgatgcc     120
acaaacggca agctgaccct caagttcatc tgcaccactg gtaaactgcc cgttccttgg     180
cccacactgg tgaccacctt cggctacggc gtggcttgtt tctctcgtta ccccgaccat     240
atgaagcagc acgacttctt caagtccgcc atgcccgagg gatacgtgca agaaaggacc     300
atctccttca aggacgatgg cacctacaag accagagccg aggtgaagtt cgagggcgac     360
acactggtga atcgtatcga actgaagggc atcgacttca agaggacggg caacattctg     420
ggccacaagc tggagtacaa cttcaacagc cactacgtgt acatcaccgc cgataagcag     480
aagaactgca tcaaggccaa cttcaagatt cgtcacaacg tggaggatgg ctccgtgcag     540
ctggccgatc actaccagca gaacacaccc atcggcgatg gacccgtttt actgcccgac     600
aaccactatt taagccacca gagcaagctg tccaaggacc ccaacgagaa gcgtgatcat     660
atggtgctgc tcgagtttgt gaccgccgcc ggcatcaccc atggaatgga cgagctgtac     720
aagagccggc tccatatggg aaactccgtg gtcacataca acaccaacat cgacgaactg     780
tgcaagagcg gcaagatcga ggaggccctg aagctgttca aggagatgga ggagaagggc     840
atcaccccca gcgtggtcac atacaccaca ctgatcgacg gactgtgtaa agccggcgac     900
```

```
gtggacgaag ccctcgagct gttcaaagag atgcggagca agggcgtgaa gcccaacgtg    960
gtgacataca ccaccctgat cgacggcctg tgcaaggccg gcaaagtgga cgaggccctg   1020
gagctgttcg acgagatgaa ggagaggggc atcaagcccg acgtggtcac atacaacacc   1080
ctgatcgacg gcctgtgcaa gagcggcaag atcgaggagg ccctgaagct gttcaaggag   1140
atggaggaga agggcatcac ccccagcgtg gttacataca ccacactgat cgacggactg   1200
tgtaaagccg gcgacgtgga cgaagccctc gagctgttca agagatgcg  gagcaagggc   1260 gtgaagccca cgtggtcac  atacaccacc ctgatcgacg gcctgtgcaa ggccggcaag   1320
gtggatgagg ccctggagct gttcgacgag atgaaggaga ggggcatcaa gcccgacgtg   1380
gttacataca acaccctgat cgacggcctg tgcaagagcg gcaagatcga ggaggccctg   1440
aagctgttca aggagatgga ggagaagggc atcaccccca gcgtggtcac atacaccaca   1500
ctgatcgacg gactgtgtaa agccggcgac gtggacgaag ccctcgagct gttcaaagag   1560
atgcggagca agggcgtgaa gcccaacgtg gtgacataca ccaccctgat cgacggcctg   1620
tgcaaggccg gcaaagtgga cgaggccctg gagctgttcg acgagatgaa ggagaggggc   1680
atcaagcccg acgtggtcac atacaacacc ctgatcgacg gcctgtgcaa gagcggcaag   1740
atcgaggagg ccctgaagct gttcaaggag atggaggaga agggcatcac ccccagcgtg   1800
gttacataca ccacactgat cgacggactg tgtaaagccg gcgacgtgga cgaagccctc   1860
gagctgttca agagatgcg  gagcaagggc gtgaagccca cgtggtcac  atacaccacc   1920 ctgatcgacg gcctgtgcaa ggccggcaag gtggatgagg ccctggagct gttcgacgag   1980
atgaaggaga ggggcatcaa gcccgacgtg gtcacataca acaccctgat cgacggcctg   2040
tgcaagagcg gcaagatcga ggaggccctg aagctgttca aggagatgga ggagaagggc   2100
atcaccccca gcgtggtcac atacaccaca ctgatcgacg gactgtgtaa agccggcgac   2160
gtggacgaag ccctcgagct gttcaaagag atgcggagca agggcgtgaa gcccaacgtg   2220
gttacataca ccaccctgat cgacggcctg tgcaaggccg gcaaagtgga cgaggccctg   2280
gagctgttcg acgagatgaa ggagaggggc atcaagcccg acgtggtcac atacaacacc   2340
ctgatcgacg gcctgtgcaa gagcggcaag atcgaggagg ccctgaagct gttcaaggag   2400
atggaggaga agggcatcac ccccagcgtg gtgacataca ccacactgat cgacggactg   2460
tgtaaagccg gcgacgtgga cgaagccctc gagctgttca agagatgcg  gagcaagggc   2520 gtgaagccca cgtggtcac  atacaccacc ctgatcgacg gcctgtgcaa ggccggcaag   2580
gtggatgagg ccctggagct gttcgacgag atgaaggaga ggggcatcaa gcccgacgag   2640
ctgacctaca cacccctgat cagcggcctg ggcaaggccg gcagagccag agaccccccc   2700
gtgctcagta gccccaagaa gaaacgcaaa gtcgaggatc aaagaagaa  aaggaaggtt   2760 gaagacccca agaaaaagag gaaggtgggt tccgactata aggaccacga cggagactac   2820
aaggatcatg atattgatta caaagacgat gacgataaga tggccccaaa gaagaagcgg   2880
aaggtcggac gctagmagvs kgtgvvvdgd vnghksvrgg gdatngktkc ttgkvwtvtt   2940
gygvacsryd hmkhdksamg yvrtskddgt yktravkgdt vnrkgdkdgn ghkynnshyv   3000
ytadkkncka nkrhnvdgsv adhyntgdgv dnhyshsksk dnkrdhmvvt aagthgmdyk   3060
srhmgnsvvt yntndcksgk akkmkgtsvv tyttdgckag dvdakmrskg vknvvtyttd   3120
gckagkvdad mkrgkdvvty ntdgcksgka kkmkgtsvvt yttdgckagd vdakmrskgv   3180
knvvtyttdg ckagkvdadm krgkdvvtyn tdgcksgkak kmkgtsvvty ttdgckagdv   3240
dakmrskgvk nvvtyttdgc kagkvdadmk rgkdvvtynt dgcksgkakk mkgtsvvtyt   3300
```

```
tdgckagdvd akmrskgvkn vvtyttdgck agkvdadmkr gkdvvtyntd gcksgkakkm     3360
kgtsvvtytt dgckagdvda kmrskgvknv vtyttdgcka gkvdadmkrg kdvvtyntdg     3420
cksgkakkmk gtsvvtyttd gckagdvdak mrskgvknvv tyttdgckag kvdadmkrgk     3480
dtyntsggka grardvsskk krkvdkkkrk vdkkkrkvgs dykdhdgdyk dhddykdddd     3540
kmakkkrkvg r                                                         3551
```

```
<210> SEQ ID NO 27
<211> LENGTH: 3552
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2912)..(2912)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2982)..(2982)
<223> OTHER INFORMATION: n is a, c, g, t or u
<220> FEATURE:
<221> NAME/KEY: misc_feature
<222> LOCATION: (2990)..(2990)
<223> OTHER INFORMATION: n is a, c, g, t or u
<220> FEATURE:
<221> NAME/KEY: misc_feature
<222> LOCATION: (2995)..(2996)
<223> OTHER INFORMATION: n is a, c, g, t or u
<220> FEATURE:
<221> NAME/KEY: misc_feature
<222> LOCATION: (3007)..(3007)
<223> OTHER INFORMATION: n is a, c, g, t or u
<220> FEATURE:
<221> NAME/KEY: misc_feature
<222> LOCATION: (3011)..(3011)
<223> OTHER INFORMATION: n is a, c, g, t or u
<220> FEATURE:
<221> NAME/KEY: misc_feature
<222> LOCATION: (3015)..(3015)
<223> OTHER INFORMATION: n is a, c, g, t or u
<220> FEATURE:
<221> NAME/KEY: misc_feature
<222> LOCATION: (3025)..(3025)
<223> OTHER INFORMATION: n is a, c, g, t or u
<220> FEATURE:
<221> NAME/KEY: misc_feature
<222> LOCATION: (3032)..(3032)
<223> OTHER INFORMATION: n is a, c, g, t or u
<220> FEATURE:
<221> NAME/KEY: misc_feature
<222> LOCATION: (3042)..(3042)
<223> OTHER INFORMATION: n is a, c, g, t or u
<220> FEATURE:
<221> NAME/KEY: misc_feature
<222> LOCATION: (3066)..(3066)
<223> OTHER INFORMATION: n is a, c, g, t or u
<220> FEATURE:
<221> NAME/KEY: misc_feature
<222> LOCATION: (3072)..(3072)
<223> OTHER INFORMATION: n is a, c, g, t or u
<220> FEATURE:
<221> NAME/KEY: misc_feature
<222> LOCATION: (3074)..(3074)
<223> OTHER INFORMATION: n is a, c, g, t or u
<220> FEATURE:
<221> NAME/KEY: misc_feature
<222> LOCATION: (3114)..(3114)
<223> OTHER INFORMATION: n is a, c, g, t or u
<220> FEATURE:
```

-continued

```
<221> NAME/KEY: misc_feature
<222> LOCATION: (3142)..(3142)
<223> OTHER INFORMATION: n is a, c, g, t or u
<220> FEATURE:
<221> NAME/KEY: misc_feature
<222> LOCATION: (3183)..(3183)
<223> OTHER INFORMATION: n is a, c, g, t or u
<220> FEATURE:
<221> NAME/KEY: misc_feature
<222> LOCATION: (3211)..(3211)
<223> OTHER INFORMATION: n is a, c, g, t or u
<220> FEATURE:
<221> NAME/KEY: misc_feature
<222> LOCATION: (3252)..(3252)
<223> OTHER INFORMATION: n is a, c, g, t or u
<220> FEATURE:
<221> NAME/KEY: misc_feature
<222> LOCATION: (3280)..(3280)
<223> OTHER INFORMATION: n is a, c, g, t or u
<220> FEATURE:
<221> NAME/KEY: misc_feature
<222> LOCATION: (3321)..(3321)
<223> OTHER INFORMATION: n is a, c, g, t or u
<220> FEATURE:
<221> NAME/KEY: misc_feature
<222> LOCATION: (3349)..(3349)
<223> OTHER INFORMATION: n is a, c, g, t or u
<220> FEATURE:
<221> NAME/KEY: misc_feature
<222> LOCATION: (3390)..(3390)
<223> OTHER INFORMATION: n is a, c, g, t or u
<220> FEATURE:
<221> NAME/KEY: misc_feature
<222> LOCATION: (3418)..(3418)
<223> OTHER INFORMATION: n is a, c, g, t or u
<220> FEATURE:
<221> NAME/KEY: misc_feature
<222> LOCATION: (3459)..(3459)
<223> OTHER INFORMATION: n is a, c, g, t or u
<220> FEATURE:
<221> NAME/KEY: misc_feature
<222> LOCATION: (3485)..(3485)
<223> OTHER INFORMATION: n is a, c, g, t or u

<400> SEQUENCE: 27
atggccggag tgtccaaagg cgaggagctg tttaccggcg tcgtgcctat tctggtggag      60
ctggacggcg acgtgaacgg ccacaagttc tccgtgaggg gcgagggcga aggcgatgcc     120
acaaacggca agctgaccct caagttcatc tgcaccactg gtaaactgcc cgttccttgg     180
cccacactgg tgaccacctt cggctacggc gtggcttgtt tctctcgtta ccccgaccat     240
atgaagcagc acgacttctt caagtccgcc atgcccgagg atacgtgca agaaaggacc      300 atctccttca aggacgatgg cacctacaag accagagccg aggtgaagtt cgagggcgac     360
acactggtga atcgtatcga actgaagggc atcgacttca agaggacggg caacattctg     420
ggccacaagc tggagtacaa cttcaacagc cactacgtgt acatcaccgc cgataagcag     480
aagaactgca tcaaggccaa cttcaagatt cgtcacaacg tggaggatgg ctccgtgcag     540
ctggccgatc actaccagca gaacacaccc atcggcgatg gacccgtttt actgcccgac     600
aaccactatt taagccacca gagcaagctg tccaaggacc ccaacgagaa gcgtgatcat     660
atggtgctgc tcgagtttgt gaccgccgcc ggcatcaccc atggaatgga cgagctgtac     720
aagagccggc tccatatggg aaactccgtg gtcacataca acaccaacat cgacaaactg     780
tgcaagagcg gcaagatcga ggaggccctg aagctgttca aggagatgga ggagaagggc     840 atcacccca gcgtggtcac atacaccaca ctgatcgacg gactgtgtaa agccggcgac     900
gtggacgaag ccctcgagct gttcaaagag atgcggagca agggcgtgaa gcccaacgtg     960
gtgacataca ccaccctgat cgacggcctg tgcaaggccg gcaaagtgga cgaggccctg    1020
```

-continued

```
gagctgttcg acgagatgaa ggagaggggc atcaagcccg acgtggtcac atacaacacc      1080
ctgatcgacg gcctgtgcaa gagcggcaag atcgaggagg ccctgaagct gttcaaggag      1140
atggaggaga aggcatcac ccccagcgtg gttacataca ccacactgat cgacggactg       1200
tgtaaagccg gcgacgtgga cgaagccctc gagctgttca aagagatgcg gagcaagggc      1260
gtgaagccca acgtggtcac ataccaccac ctgatcgacg gcctgtgcaa ggccggcaag      1320
gtggatgagg ccctggagct gttcgacgag atgaaggaga ggggcatcaa gcccgacgtg      1380
gttacataca acccctgat cgacggcctg tgcaagagcg gcaagatcga ggaggccctg       1440
aagctgttca aggagatgga ggagaagggc atcaccccca gcgtggtcac atacaccaca      1500
ctgatcgacg gactgtgtaa agccggcgac gtggacgaag ccctcgagct gttcaaagag      1560
atgcggagca aggcgtgaa gcccaacgtg gtgacataca ccaccctgat cgacggcctg       1620
tgcaaggccg gcaaagtgga cgaggccctg gagctgttcg acgagatgaa ggagagggc       1680 atcaagcccg acgtggtcac atacaacacc ctgatcgacg gcctgtgcaa gagcggcaag      1740
atcgaggagg ccctgaagct gttcaaggag atggaggaga aggcatcac ccccagcgtg       1800 gttacataca ccacactgat cgacggactg tgtaaagccg gcgacgtgga cgaagccctc      1860
gagctgttca aagagatgcg gagcaagggc gtgaagccca acgtggtcac ataccaccac      1920
ctgatcgacg gcctgtgcaa ggccggcaag gtggatgagg ccctggagct gttcgacgag      1980
atgaaggaga ggggcatcaa gcccgacgtg gtcacataca cacccctgat cgacggcctg      2040
tgcaagagcg gcaagatcga ggaggccctg aagctgttca aggagatgga ggagaagggc      2100
atcaccccca gcgtggtcac ataccaccac ctgatcgacg gactgtgtaa agccggcgac      2160
gtggacgaag ccctcgagct gttcaaagag atgcggagca aggcgtgaa gcccaacgtg       2220 gttacataca ccaccctgat cgacggcctg tgcaaggccg gcaaagtgga cgaggccctg      2280
gagctgttcg acgagatgaa ggagagggc atcaagcccg acgtggtcac atacaacacc       2340
ctgatcgacg gcctgtgcaa gagcggcaag atcgaggagg ccctgaagct gttcaaggag      2400
atggaggaga aggcatcac ccccagcgtg gtgacataca ccacactgat cgacggactg       2460
tgtaaagccg gcgacgtgga cgaagccctc gagctgttca aagagatgcg gagcaagggc      2520
gtgaagccca acgtggtcac ataccaccac ctgatcgacg gcctgtgcaa ggccggcaag      2580
gtggatgagg ccctggagct gttcgacgag atgaaggaga ggggcatcaa gcccgacgag      2640
ctgacctaca cacccctgat cagcggcctg ggcaaggccg gcagagccag agaccccccc      2700
gtgctcagta gcccccaagaa gaaacgcaaa gtcgaggatc caaagaagaa aaggaaggtt      2760
gaagacccca agaaaaagag gaaggtgggt tccgactata aggaccacga cggagactac      2820
aaggatcatg atattgatta caaagacgat gacgataaga tggcccccaaa gaagaagcgg      2880 aaggtcggac gctagmagvs kgtgvvvdgd vnghksvrgg gdatngktkc ttgkvwtvtt       2940
gygvacsryd hmkhdksamg yvrtskddgt yktravkgdt vnrkgdkdgn ghkynnshyv       3000
ytadkkncka nkrhnvdgsv adhyntgdgv dnhyshsksk dnkrdhmvvt aagthgmdyk       3060
srhmgnsvvt yntndkcksg kakkmkgtsv vtyttdgcka gdvdakmrsk gvknvvtytt       3120
dgckagkvda dmkrgkdvvt yntdgcksgk akkmkgtsvv tyttdgckag dvdakmrskg       3180
vknvvtyttd gckagkvdad mkrgkdvvty ntdgcksgka kkmkgtsvvt yttdgckagd       3240
vdakmrskgv knvvtyttdg ckagkvdadm krgkdvvtyn tdgcksgkak kmkgtsvvty       3300
ttdgckagdv dakmrskgvk nvvtyttdgc kagkvdadmk rgkdvvtynt dgcksgkakk       3360
```

-continued

```
mkgtsvvtyt tdgckagdvd akmrskgvkn vvtyttdgck agkvdadmkr gkdvvtyntd    3420
gcksgkakkm kgtsvvtytt dgckagdvda kmrskgvknv vtyttdgcka gkvdadmkrg    3480
kdtyntsggk agrardvssk kkrkvdkkkr kvdkkkrkvg sdykdhdgdy kdhddykddd    3540
dkmakkkrkv gr                                                        3552
```

```
<210> SEQ ID NO 28
<211> LENGTH: 3552
<212> TYPE: DNA
<213> ORGANISM: Artificial sequence
<220> FEATURE:
<223> OTHER INFORMATION: PPR vector
<220> FEATURE:
<221> NAME/KEY: misc_feature
<222> LOCATION: (2912)..(2912)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2982)..(2982)
<223> OTHER INFORMATION: n is a, c, g, t or u
<220> FEATURE:
<221> NAME/KEY: misc_feature
<222> LOCATION: (2990)..(2990)
<223> OTHER INFORMATION: n is a, c, g, t or u
<220> FEATURE:
<221> NAME/KEY: misc_feature
<222> LOCATION: (2995)..(2996)
<223> OTHER INFORMATION: n is a, c, g, t or u
<220> FEATURE:
<221> NAME/KEY: misc_feature
<222> LOCATION: (3007)..(3007)
<223> OTHER INFORMATION: n is a, c, g, t or u
<220> FEATURE:
<221> NAME/KEY: misc_feature
<222> LOCATION: (3011)..(3011)
<223> OTHER INFORMATION: n is a, c, g, t or u
<220> FEATURE:
<221> NAME/KEY: misc_feature
<222> LOCATION: (3015)..(3015)
<223> OTHER INFORMATION: n is a, c, g, t or u
<220> FEATURE:
<221> NAME/KEY: misc_feature
<222> LOCATION: (3025)..(3025)
<223> OTHER INFORMATION: n is a, c, g, t or u
<220> FEATURE:
<221> NAME/KEY: misc_feature
<222> LOCATION: (3032)..(3032)
<223> OTHER INFORMATION: n is a, c, g, t or u
<220> FEATURE:
<221> NAME/KEY: misc_feature
<222> LOCATION: (3042)..(3042)
<223> OTHER INFORMATION: n is a, c, g, t or u
<220> FEATURE:
<221> NAME/KEY: misc_feature
<222> LOCATION: (3066)..(3066)
<223> OTHER INFORMATION: n is a, c, g, t or u
<220> FEATURE:
<221> NAME/KEY: misc_feature
<222> LOCATION: (3072)..(3072)
<223> OTHER INFORMATION: n is a, c, g, t or u
<220> FEATURE:
<221> NAME/KEY: misc_feature
<222> LOCATION: (3114)..(3114)
<223> OTHER INFORMATION: n is a, c, g, t or u
<220> FEATURE:
<221> NAME/KEY: misc_feature
<222> LOCATION: (3142)..(3142)
<223> OTHER INFORMATION: n is a, c, g, t or u
<220> FEATURE:
<221> NAME/KEY: misc_feature
<222> LOCATION: (3183)..(3183)
<223> OTHER INFORMATION: n is a, c, g, t or u
```

<220> FEATURE:
<221> NAME/KEY: misc_feature
<222> LOCATION: (3211)..(3211)
<223> OTHER INFORMATION: n is a, c, g, t or u
<220> FEATURE:
<221> NAME/KEY: misc_feature
<222> LOCATION: (3252)..(3252)
<223> OTHER INFORMATION: n is a, c, g, t or u
<220> FEATURE:
<221> NAME/KEY: misc_feature
<222> LOCATION: (3280)..(3280)
<223> OTHER INFORMATION: n is a, c, g, t or u
<220> FEATURE:
<221> NAME/KEY: misc_feature
<222> LOCATION: (3321)..(3321)
<223> OTHER INFORMATION: n is a, c, g, t or u
<220> FEATURE:
<221> NAME/KEY: misc_feature
<222> LOCATION: (3349)..(3349)
<223> OTHER INFORMATION: n is a, c, g, t or u
<220> FEATURE:
<221> NAME/KEY: misc_feature
<222> LOCATION: (3390)..(3390)
<223> OTHER INFORMATION: n is a, c, g, t or u
<220> FEATURE:
<221> NAME/KEY: misc_feature
<222> LOCATION: (3418)..(3418)
<223> OTHER INFORMATION: n is a, c, g, t or u
<220> FEATURE:
<221> NAME/KEY: misc_feature
<222> LOCATION: (3459)..(3459)
<223> OTHER INFORMATION: n is a, c, g, t or u
<220> FEATURE:
<221> NAME/KEY: misc_feature
<222> LOCATION: (3485)..(3485)
<223> OTHER INFORMATION: n is a, c, g, t or u

<400> SEQUENCE: 28
atggccggag tgtccaaagg cgaggagctg tttaccggcg tcgtgcctat tctggtggag      60
ctggacggcg acgtgaacgg ccacaagttc tccgtgaggg gcgagggcga aggcgatgcc     120
acaaacggca agctgaccct caagttcatc tgcaccactg gtaaactgcc cgttccttgg     180
cccacactgg tgaccacctt cggctacggc gtggcttgtt tctctcgtta ccccgaccat     240
atgaagcagc acgacttctt caagtccgcc atgcccgagg gatacgtgca agaaaggacc     300
atctccttca aggacgatgg cacctacaag accagagccg aggtgaagtt cgagggcgac     360
acactggtga atcgtatcga actgaagggc atcgacttca agaggacggg caacattctg     420
ggccacaagc tggagtacaa cttcaacagc cactacgtgt acatcaccgc cgataagcag     480
aagaactgca tcaaggccaa cttcaagatt cgtcacaacg tggaggatgg ctccgtgcag     540
ctggccgatc actaccagca gaacacaccc atcggcgatg acccgtttt actgcccgac      600 aaccactatt taagccacca gagcaagctg tccaaggacc ccaacgagaa gcgtgatcat     660
atggtgctgc tcgagtttgt gaccgccgcc ggcatcaccc atggaatgga cgagctgtac     720
aagagccggc tccatatggg aaactccgtg gtcacataca acaccgatat cgacggcctg     780
tgcaagagcg gcaagatcga ggaggccctg aagctgttca aggagatgga ggagaagggc     840 atcacccca gcgtggtcac atacaccaca ctgatcgacg gactgtgtaa agccggcgac     900
gtggacgaag ccctcgagct gttcaaagag atgcggagca agggcgtgaa gcccaacgtg     960
gtgacataca ccaccctgat cgacggcctg tgcaaggccg gcaaagtgga cgaggccctg    1020
gagctgttcg acgagatgaa ggagaggggc atcaagcccg acgtggtcac atacaacacc    1080
ctgatcgacg gcctgtgcaa gagcggcaag atcgaggagg ccctgaagct gttcaaggag    1140
atggaggaga agggcatcac ccccagcgtg gttacataca ccacactgat cgacggactg    1200

```
tgtaaagccg gcgacgtgga cgaagccctc gagctgttca aagagatgcg gagcaagggc  1260
gtgaagccca acgtggtcac atacaccacc ctgatcgacg gcctgtgcaa ggccggcaag  1320
gtggatgagg ccctggagct gttcgacgag atgaaggaga ggggcatcaa gcccgacgtg  1380
gttacataca acaccctgat cgacggcctg tgcaagagcg gcaagatcga ggaggccctg  1440
aagctgttca aggagatgga ggagaagggc atcaccccca gcgtggtcac atacaccaca  1500
ctgatcgacg gactgtgtaa agccggcgac gtggacgaag ccctcgagct gttcaaagag  1560
atgcggagca agggcgtgaa gcccaacgtg gtgacataca ccaccctgat cgacggcctg  1620
tgcaaggccg gcaaagtgga cgaggccctg gagctgttcg acgagatgaa ggagaggggc  1680
atcaagcccg acgtggtcac atacaacacc ctgatcgacg gcctgtgcaa gagcggcaag  1740
atcgaggagg ccctgaagct gttcaaggag atggaggaga agggcatcac ccccagcgtg  1800
gttacataca ccacactgat cgacggactg tgtaaagccg gcgacgtgga cgaagccctc  1860
gagctgttca aagagatgcg gagcaagggc gtgaagccca acgtggtcac atacaccacc  1920
ctgatcgacg gcctgtgcaa ggccggcaag gtggatgagg ccctggagct gttcgacgag  1980
atgaaggaga ggggcatcaa gcccgacgtg gtcacataca acaccctgat cgacggcctg  2040
tgcaagagcg gcaagatcga ggaggccctg aagctgttca aggagatgga ggagaagggc  2100
atcaccccca gcgtggtcac atacaccaca ctgatcgacg gactgtgtaa agccggcgac  2160
gtggacgaag ccctcgagct gttcaaagag atgcggagca agggcgtgaa gcccaacgtg  2220
gttacataca ccaccctgat cgacggcctg tgcaaggccg gcaaagtgga cgaggccctg  2280
gagctgttcg acgagatgaa ggagaggggc atcaagcccg acgtggtcac atacaacacc  2340
ctgatcgacg gcctgtgcaa gagcggcaag atcgaggagg ccctgaagct gttcaaggag  2400
atggaggaga agggcatcac ccccagcgtg gtgacataca ccacactgat cgacggactg  2460
tgtaaagccg gcgacgtgga cgaagccctc gagctgttca aagagatgcg gagcaagggc  2520
gtgaagccca acgtggtcac atacaccacc ctgatcgacg gcctgtgcaa ggccggcaag  2580
gtggatgagg ccctggagct gttcgacgag atgaaggaga ggggcatcaa gcccgacgag  2640
ctgacctaca cacccctgat cagcggcctg ggcaaggccg gcagagccag agacccccc  2700 gtgctcagta gccccaagaa gaaacgcaaa gtcgaggatc aaagaagaa aaggaaggtt  2760 gaagacccca agaaaaagag gaaggtgggt tccgactata aggaccacga cggagactac  2820
aaggatcatg atattgatta caaagacgat gacgataaga tggcccccaa gaagaagcgg  2880
aaggtcggac gctagmagvs kgtgvvvdgd vnghksvrgg gdatngktkc ttgkvwtvtt  2940
gygvacsryd hmkhdksamg yvrtskddgt yktravkgdt vnrkgdkdgn ghkynnshyv  3000
ytadkkncka nkrhnvdgsv adhyntgdgv dnhyshsksk dnkrdhmvvt aagthgmdyk  3060
srhmgnsvvt yntddgcksg kakkmkgtsv vtyttdgcka gdvdakmrsk gvknvvtytt  3120
dgckagkvda dmkrgkdvvt yntdgcksgk akkmkgtsvv tyttdgckag dvdakmrskg  3180
vknvvtyttd gckagkvdad mkrgkdvvty ntdgcksgka kkmkgtsvvt yttdgckagd  3240
vdakmrskgv knvvtyttdg ckagkvdadm krgkdvvtyn tdgcksgkak kmkgtsvvty  3300
ttdgckagdv dakmrskgvk nvvtyttdgc kagkvdadmk rgkdvvtynt dgcksgkakk  3360
mkgtsvvtyt tdgckagdvd akmrskgvkn vvtyttdgck agkvdadmkr gkdvvtyntd  3420
gcksgkakkm kgtsvvtytt dgckagdvda kmrskgvknv vtyttdgcka gkvdadmkrg  3480
kdtyntsggk agrardvssk kkrkvdkkkr kvdkkkrkvg sdykdhdgdy kdhddykddd  3540
dkmakkkrkv gr                                                     3552
```

```
<210> SEQ ID NO 29
<211> LENGTH: 3189
<212> TYPE: DNA
<213> ORGANISM: Artificial sequence
<220> FEATURE:
<223> OTHER INFORMATION: NL_PPRcag_1
<220> FEATURE:
<221> NAME/KEY: misc_feature
<222> LOCATION: (2626)..(2626)
<223> OTHER INFORMATION: n is a, c, g, t or u
<220> FEATURE:
<221> NAME/KEY: misc_feature
<222> LOCATION: (2634)..(2634)
<223> OTHER INFORMATION: n is a, c, g, t or u
<220> FEATURE:
<221> NAME/KEY: misc_feature
<222> LOCATION: (2644)..(2644)
<223> OTHER INFORMATION: n is a, c, g, t or u
<220> FEATURE:
<221> NAME/KEY: misc_feature
<222> LOCATION: (2678)..(2678)
<223> OTHER INFORMATION: n is a, c, g, t or u
<220> FEATURE:
<221> NAME/KEY: misc_feature
<222> LOCATION: (2698)..(2698)
<223> OTHER INFORMATION: n is a, c, g, t or u
<220> FEATURE:
<221> NAME/KEY: misc_feature
<222> LOCATION: (2700)..(2700)
<223> OTHER INFORMATION: n is a, c, g, t or u
<220> FEATURE:
<221> NAME/KEY: misc_feature
<222> LOCATION: (2704)..(2704)
<223> OTHER INFORMATION: n is a, c, g, t or u
<220> FEATURE:
<221> NAME/KEY: misc_feature
<222> LOCATION: (2711)..(2711)
<223> OTHER INFORMATION: n is a, c, g, t or u
<220> FEATURE:
<221> NAME/KEY: misc_feature
<222> LOCATION: (2740)..(2740)
<223> OTHER INFORMATION: n is a, c, g, t or u
<220> FEATURE:
<221> NAME/KEY: misc_feature
<222> LOCATION: (2746)..(2746)
<223> OTHER INFORMATION: n is a, c, g, t or u
<220> FEATURE:
<221> NAME/KEY: misc_feature
<222> LOCATION: (2787)..(2787)
<223> OTHER INFORMATION: n is a, c, g, t or u
<220> FEATURE:
<221> NAME/KEY: misc_feature
<222> LOCATION: (2815)..(2815)
<223> OTHER INFORMATION: n is a, c, g, t or u
<220> FEATURE:
<221> NAME/KEY: misc_feature
<222> LOCATION: (2856)..(2856)
<223> OTHER INFORMATION: n is a, c, g, t or u
<220> FEATURE:
<221> NAME/KEY: misc_feature
<222> LOCATION: (2884)..(2884)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2953)..(2953)
<223> OTHER INFORMATION: n is a, c, g, t or u
<220> FEATURE:
<221> NAME/KEY: misc_feature
<222> LOCATION: (2994)..(2994)
<223> OTHER INFORMATION: n is a, c, g, t or u
<220> FEATURE:
<221> NAME/KEY: misc_feature
<222> LOCATION: (3022)..(3022)
```

```
<223> OTHER INFORMATION: n is a, c, g, t or u
<220> FEATURE:
<221> NAME/KEY: misc_feature
<222> LOCATION: (3063)..(3063)
<223> OTHER INFORMATION: n is a, c, g, t or u
<220> FEATURE:
<221> NAME/KEY: misc_feature
<222> LOCATION: (3091)..(3091)
<223> OTHER INFORMATION: n is a, c, g, t or u
<220> FEATURE:
<221> NAME/KEY: misc_feature
<222> LOCATION: (3132)..(3132)
<223> OTHER INFORMATION: n is a, c, g, t or u
<220> FEATURE:
<221> NAME/KEY: misc_feature
<222> LOCATION: (3158)..(3158)
<223> OTHER INFORMATION: n is a, c, g, t or u

<400> SEQUENCE: 29
atggccggag tgttcacact ggaggacttc gtgggcgact ggagacagac cgccggctac        60
aacctggacc aggtgctgga gcagggcgga gtgagcagcc tgtttcagaa cctgggcgtg       120
agcgtcaccc ccatccagag gatcgtgctg tccggcgaga atggcctgaa gatcgacatc       180
cacgtcatca tcccctacga gggcctgagc ggcgatcaga tgggccagat cgagaagatc       240
ttcaaggtgg tgtatcccgt cgacgaccac cacttcaagg tgatcctgca ttacggcacc       300
ctcgtgatcg acggcgtgac ccctaacatg atcgactact tcggcaggcc ctacgaggga       360
atcgccgtgt cgacggaaa gaagatcacc gtgaccggca ccctgtggaa cggaaacaag       420
atcatcgacg agaggctgat caaccccgac ggctccctgc tgttcagggt gaccatcaat       480
ggcgtgaccg gctggagact gtgcgagaga atcctggccg gaggcggagg aagcctcgtg       540
cccagaggat ccggcggagg cggctccagc cggctccata tgggaaactc cgtggtcaca       600
tacaacaccc tgatcgacgg cctgtgcaag agcggcaaga tcgaggaggc cctgaagctg       660
ttcaaggaga tggaggagaa gggcatcacc cccagcgtgg tcacatacac cacactgatc       720
gacggactgt gtaaagccgg cgacgtggac gaagccctcg agctgttcaa agagatgcgg       780
agcaagggcg tgaagcccaa cgtggtgaca tacaccaccc tgatcgacgg cctgtgcaag       840
gccggcaaag tggacgaggc cctggagctg ttcgacgaga tgaaggagag gggcatcaag       900
cccgacgtgg tcacatacaa caccctgatc gacggcctgt gcaagagcgg caagatcgag       960
gaggccctga gctgttcaa ggagatggag gagaagggca tcaccccag cgtggttaca      1020 tacaccacac tgatcgacgg actgtgtaaa gccggcgacg tggacgaagc cctcgagctg      1080
ttcaaagaga tgcggagcaa gggcgtgaag cccaacgtgg tcacatacac caccctgatc      1140
gacggcctgt gcaaggccgg caaggtggat gaggccctgg agctgttcga cgagatgaag      1200
gagaggggca tcaagcccga cgtggttaca tacaacaccc tgatcgacgg cctgtgcaag      1260
agcggcaaga tcgaggaggc cctgaagctg ttcaaggaga tggaggagaa gggcatcacc      1320
cccagcgtgg tcacatacac cacactgatc gacggactgt gtaaagccgg cgacgtggac      1380
gaagccctcg agctgttcaa agagatgcgg agcaagggcg tgaagcccaa cgtggtgaca      1440
tacaccaccc tgatcgacgg cctgtgcaag gccggcaaag tggacgaggc cctggagctg      1500
ttcgacgaga tgaaggagag gggcatcaag cccgacgtgg tcacatacaa caccctgatc      1560
gacggcctgt gcaagagcgg caagatcgag gaggccctga gctgttcaa ggagatggag      1620 gagaagggca tcaccccag cgtggttaca tacaccacac tgatcgacgg actgtgtaaa      1680
gccggcgacg tggacgaagc cctcgagctg ttcaaagaga tgcggagcaa gggcgtgaag      1740
cccaacgtgg tcacatacac caccctgatc gacggcctgt gcaaggccgg caaggtggat      1800
```

```
gaggccctgg agctgttcga cgagatgaag gagaggggca tcaagcccga cgtggtcaca      1860
tacaacaccc tgatcgacgg cctgtgcaag agcggcaaga tcgaggaggc cctgaagctg      1920
ttcaaggaga tggaggagaa gggcatcacc cccagcgtgg tcacatacac cacactgatc      1980
gacggactgt gtaaagccgg cgacgtggac gaagccctcg agctgttcaa agagatgcgg      2040
agcaagggcg tgaagcccaa cgtggttaca taccaccccc tgatcgacgg cctgtgcaag      2100
gccggcaaag tggacgaggc cctggagctg ttcgacgaga tgaaggagag gggcatcaag      2160
cccgacgtgg tcacatacaa caccctgatc gacggcctgt gcaagagcgg caagatcgag      2220
gaggccctga agctgttcaa ggagatggag gagaagggca tcaccccccag cgtggtgaca      2280 tacaccacac tgatcgacgg actgtgtaaa gccggcgacg tggacgaagc cctcgagctg      2340
ttcaaagaga tgcggagcaa gggcgtgaag cccaacgtgg tcacatacac caccctgatc      2400
gacggcctgt gcaaggccgg caaggtggat gaggccctgg agctgttcga cgagatgaag      2460 gagagggggca tcaagcccga cgagctgacc tacaacaccc tgatcagcgg cctgggcaag      2520
gccggcagag ccagagaccc ccccgtgctc agtagcggct ccggcggcag cggggggaggc      2580 gggcatcatc accatcacca cggacgctag magvtdvgdw rtagyndvgg vssngvsvtr      2640
vsgngkdhvy gsgdmgkkvv yvddhhkvhy gtvdgvtnmd ygrygavdgk ktvtgtwngn      2700
kdrndgsrvt ngvtgwrcra ggggsvrgsg gggssrhmgn svvtyntdgc ksgkakkmkg      2760
tsvvtyttdg ckagdvdakm rskgvknvvt yttdgckagk vdadmkrgkd vvtyntdgck      2820
sgkakkmkgt svvtyttdgc kagdvdakmr skgvknvvty ttdgckagkv dadmkrgkdv      2880
vtyntdgcks gkakkmkgts vvtyttdgck agdvdakmrs kgvknvvtyt tdgckagkvd      2940
admkrgkdvv tyntdgcksg kakkmkgtsv vtyttdgcka gdvdakmrsk gvknvvtytt      3000
dgckagkvda dmkrgkdvvt yntdgcksgk akkmkgtsvv tyttdgckag dvdakmrskg      3060
vknvvtyttd gckagkvdad mkrgkdvvty ntdgcksgka kkmkgtsvvt yttdgckagd      3120
vdakmrskgv knvvtyttdg ckagkvdadm krgkdtynts ggkagrardv ssgsggsggg      3180 ghhhhhhgr                                                             3189
```

<210> SEQ ID NO 30
<211> LENGTH: 3188
<212> TYPE: DNA
<213> ORGANISM: Artificial sequence
<220> FEATURE:
<223> OTHER INFORMATION: NL_PPRcag_2
<220> FEATURE:
<221> NAME/KEY: misc_feature
<222> LOCATION: (2626)..(2626)
<223> OTHER INFORMATION: n is a, c, g, t or u
<220> FEATURE:
<221> NAME/KEY: misc_feature
<222> LOCATION: (2634)..(2634)
<223> OTHER INFORMATION: n is a, c, g, t or u
<220> FEATURE:
<221> NAME/KEY: misc_feature
<222> LOCATION: (2644)..(2644)
<223> OTHER INFORMATION: n is a, c, g, t or u
<220> FEATURE:
<221> NAME/KEY: misc_feature
<222> LOCATION: (2678)..(2678)
<223> OTHER INFORMATION: n is a, c, g, t or u
<220> FEATURE:
<221> NAME/KEY: misc_feature
<222> LOCATION: (2698)..(2698)
<223> OTHER INFORMATION: n is a, c, g, t or u
<220> FEATURE:
<221> NAME/KEY: misc_feature
<222> LOCATION: (2700)..(2700)

```
<223> OTHER INFORMATION: n is a, c, g, t or u
<220> FEATURE:
<221> NAME/KEY: misc_feature
<222> LOCATION: (2704)..(2704)
<223> OTHER INFORMATION: n is a, c, g, t or u
<220> FEATURE:
<221> NAME/KEY: misc_feature
<222> LOCATION: (2711)..(2711)
<223> OTHER INFORMATION: n is a, c, g, t or u
<220> FEATURE:
<221> NAME/KEY: misc_feature
<222> LOCATION: (2740)..(2740)
<223> OTHER INFORMATION: n is a, c, g, t or u
<220> FEATURE:
<221> NAME/KEY: misc_feature
<222> LOCATION: (2746)..(2746)
<223> OTHER INFORMATION: n is a, c, g, t or u
<220> FEATURE:
<221> NAME/KEY: misc_feature
<222> LOCATION: (2786)..(2786)
<223> OTHER INFORMATION: n is a, c, g, t or u
<220> FEATURE:
<221> NAME/KEY: misc_feature
<222> LOCATION: (2814)..(2814)
<223> OTHER INFORMATION: n is a, c, g, t or u
<220> FEATURE:
<221> NAME/KEY: misc_feature
<222> LOCATION: (2855)..(2855)
<223> OTHER INFORMATION: n is a, c, g, t or u
<220> FEATURE:
<221> NAME/KEY: misc_feature
<222> LOCATION: (2883)..(2883)
<223> OTHER INFORMATION: n is a, c, g, t or u
<220> FEATURE:
<221> NAME/KEY: misc_feature
<222> LOCATION: (2924)..(2924)
<223> OTHER INFORMATION: n is a, c, g, t or u
<220> FEATURE:
<221> NAME/KEY: misc_feature
<222> LOCATION: (2952)..(2952)
<223> OTHER INFORMATION: n is a, c, g, t or u
<220> FEATURE:
<221> NAME/KEY: misc_feature
<222> LOCATION: (2993)..(2993)
<223> OTHER INFORMATION: n is a, c, g, t or u
<220> FEATURE:
<221> NAME/KEY: misc_feature
<222> LOCATION: (3021)..(3021)
<223> OTHER INFORMATION: n is a, c, g, t or u
<220> FEATURE:
<221> NAME/KEY: misc_feature
<222> LOCATION: (3062)..(3062)
<223> OTHER INFORMATION: n is a, c, g, t or u
<220> FEATURE:
<221> NAME/KEY: misc_feature
<222> LOCATION: (3090)..(3090)
<223> OTHER INFORMATION: n is a, c, g, t or u
<220> FEATURE:
<221> NAME/KEY: misc_feature
<222> LOCATION: (3131)..(3131)
<223> OTHER INFORMATION: n is a, c, g, t or u
<220> FEATURE:
<221> NAME/KEY: misc_feature
<222> LOCATION: (3157)..(3157)
<223> OTHER INFORMATION: n is a, c, g, t or u

<400> SEQUENCE: 30
atggccggag tgttcacact ggaggacttc gtgggcgact ggagacagac cgccggctac        60
aacctggacc aggtgctgga gcagggcgga gtgagcagcc tgtttcagaa cctgggcgtg       120
agcgtcaccc ccatccagag gatcgtgctg tccggcgaga atggcctgaa gatcgacatc       180
cacgtcatca tcccctacga gggcctgagc ggcgatcaga tgggccagat cgagaagatc       240
ttcaaggtgg tgtatcccgt cgacgaccac cacttcaagg tgatcctgca ttacggcacc       300
ctcgtgatcg acggcgtgac ccctaacatg atcgactact tcggcaggcc ctacgaggga       360
```

```
atcgccgtgt tcgacggaaa gaagatcacc gtgaccggca ccctgtggaa cggaaacaag      420
atcatcgacg agaggctgat caaccccgac ggctccctgc tgttcagggt gaccatcaat      480
ggcgtgaccg gctggagact gtgcgagaga atcctggccg gaggcggagg aagcctcgtg      540
cccagaggat ccggcggagg cggctccagc cggctccata tgggaaactc cgtggtcaca      600
tacaacaccc tgatcgacga actgtgcaag agcggcaaga tcgaggaggc cctgaagctg      660
ttcaaggaga tggaggagaa gggcatcacc cccagcgtgg tcacatacac cacactgatc      720
gacggactgt gtaaagccgg cgacgtggac gaagccctcg agctgttcaa agagatgcgg      780
agcaagggcg tgaagcccaa cgtggtgaca tacaccaccc tgatcgacgg cctgtgcaag      840
gccggcaaag tggacgaggc cctggagctg ttcgacgaga tgaaggagag gggcatcaag      900
cccgacgtgg tcacatacaa caccctgatc gacggcctgt gcaagagcgg caagatcgag      960
gaggccctga agctgttcaa ggagatggag gagaagggca tcaccccag cgtggttaca      1020 tacaccacac tgatcgacgg actgtgtaaa gccggcgacg tggacgaagc cctcgagctg      1080
ttcaaagaga tgcggagcaa gggcgtgaag cccaacgtgg tcacatacac caccctgatc      1140
gacggcctgt gcaaggccgg caaggtggat gaggccctgg agctgttcga cgagatgaag      1200
gagaggggca tcaagcccga cgtggttaca tacaacaccc tgatcgacgg cctgtgcaag      1260
agcggcaaga tcgaggaggc cctgaagctg ttcaaggaga tggaggagaa gggcatcacc      1320
cccagcgtgg tcacatacac cacactgatc gacggactgt gtaaagccgg cgacgtggac      1380
gaagccctcg agctgttcaa agagatgcgg agcaagggcg tgaagcccaa cgtggtgaca      1440
tacaccaccc tgatcgacgg cctgtgcaag gccggcaaag tggacgaggc cctggagctg      1500
ttcgacgaga tgaaggagag gggcatcaag cccgacgtgg tcacatacaa caccctgatc      1560
gacggcctgt gcaagagcgg caagatcgag gaggccctga agctgttcaa ggagatggag      1620
gagaagggca tcaccccag cgtggttaca tacaccacac tgatcgacgg actgtgtaaa      1680
gccggcgacg tggacgaagc cctcgagctg ttcaaagaga tgcggagcaa gggcgtgaag      1740
cccaacgtgg tcacatacac caccctgatc gacggcctgt gcaaggccgg caaggtggat      1800
gaggccctgg agctgttcga cgagatgaag gagaggggca tcaagcccga cgtggtcaca      1860
tacaacaccc tgatcgacgg cctgtgcaag agcggcaaga tcgaggaggc cctgaagctg      1920
ttcaaggaga tggaggagaa gggcatcacc cccagcgtgg tcacatacac cacactgatc      1980
gacggactgt gtaaagccgg cgacgtggac gaagccctcg agctgttcaa agagatgcgg      2040
agcaagggcg tgaagcccaa cgtggttaca tacaccaccc tgatcgacgg cctgtgcaag      2100
gccggcaaag tggacgaggc cctggagctg ttcgacgaga tgaaggagag gggcatcaag      2160
cccgacgtgg tcacatacaa caccctgatc gacggcctgt gcaagagcgg caagatcgag      2220
gaggccctga agctgttcaa ggagatggag gagaagggca tcaccccag cgtggtgaca      2280 tacaccacac tgatcgacgg actgtgtaaa gccggcgacg tggacgaagc cctcgagctg      2340
ttcaaagaga tgcggagcaa gggcgtgaag cccaacgtgg tcacatacac caccctgatc      2400
gacggcctgt gcaaggccgg caaggtggat gaggccctgg agctgttcga cgagatgaag      2460
gagaggggca tcaagcccga cgagctgacc tacaacaccc tgatcagcgg cctgggcaag      2520
gccggcagag ccagagaccc ccccgtgctc agtagcggct ccggcggcag cggggggaggc      2580 gggcatcatc accatcacca cggacgctag magvtdvgdw rtagyndvgg vssngvsvtr      2640
vsgngkdhvy gsgdmgkkvv yvddhhkvhy gtvdgvtnmd ygrygavdgk ktvtgtwngn      2700
```

-continued

```
kdrndgsrvt ngvtgwrcra ggggsvrgsg gggssrhmgn svvtyntdck sgkakkmkgt    2760
svvtyttdgc kagdvdakmr skgvknvvty ttdgckagkv dadmkrgkdv vtyntdgcks    2820
gkakkmkgts vvtyttdgck agdvdakmrs kgvknvvtyt tdgckagkvd admkrgkdvv    2880
tyntdgcksg kakkmkgtsv vtyttdgcka gdvdakmrsk gvknvvtytt dgckagkvda    2940
dmkrgkdvvt yntdgcksgk akkmkgtsvv tyttdgckag dvdakmrskg vknvvtyttd    3000
gckagkvdad mkrgkdvvty ntdgcksgka kkmkgtsvvt yttdgckagd vdakmrskgv    3060
knvvtyttdg ckagkvdadm krgkdvvtyn tdgcksgkak kmkgtsvvty ttdgckagdv    3120
dakmrskgvk nvvtyttdgc kagkvdadmk rgkdtyntsg gkagrardvs sgsggsgggg    3180 hhhhhhgr                                                            3188
```

```
<210> SEQ ID NO 31
<211> LENGTH: 3189
<212> TYPE: DNA
<213> ORGANISM: Artificial sequence
<220> FEATURE:
<223> OTHER INFORMATION: NL_PPRcag_3
<220> FEATURE:
<221> NAME/KEY: misc_feature
<222> LOCATION: (2626)..(2626)
<223> OTHER INFORMATION: n is a, c, g, t or u
<220> FEATURE:
<221> NAME/KEY: misc_feature
<222> LOCATION: (2634)..(2634)
<223> OTHER INFORMATION: n is a, c, g, t or u
<220> FEATURE:
<221> NAME/KEY: misc_feature
<222> LOCATION: (2644)..(2644)
<223> OTHER INFORMATION: n is a, c, g, t or u
<220> FEATURE:
<221> NAME/KEY: misc_feature
<222> LOCATION: (2678)..(2678)
<223> OTHER INFORMATION: n is a, c, g, t or u
<220> FEATURE:
<221> NAME/KEY: misc_feature
<222> LOCATION: (2698)..(2698)
<223> OTHER INFORMATION: n is a, c, g, t or u
<220> FEATURE:
<221> NAME/KEY: misc_feature
<222> LOCATION: (2700)..(2700)
<223> OTHER INFORMATION: n is a, c, g, t or u
<220> FEATURE:
<221> NAME/KEY: misc_feature
<222> LOCATION: (2704)..(2704)
<223> OTHER INFORMATION: n is a, c, g, t or u
<220> FEATURE:
<221> NAME/KEY: misc_feature
<222> LOCATION: (2711)..(2711)
<223> OTHER INFORMATION: n is a, c, g, t or u
<220> FEATURE:
<221> NAME/KEY: misc_feature
<222> LOCATION: (2740)..(2740)
<223> OTHER INFORMATION: n is a, c, g, t or u
<220> FEATURE:
<221> NAME/KEY: misc_feature
<222> LOCATION: (2746)..(2746)
<223> OTHER INFORMATION: n is a, c, g, t or u
<220> FEATURE:
<221> NAME/KEY: misc_feature
<222> LOCATION: (2748)..(2748)
<223> OTHER INFORMATION: n is a, c, g, t or u
<220> FEATURE:
<221> NAME/KEY: misc_feature
<222> LOCATION: (2787)..(2787)
<223> OTHER INFORMATION: n is a, c, g, t or u
<220> FEATURE:
<221> NAME/KEY: misc_feature
<222> LOCATION: (2815)..(2815)
<223> OTHER INFORMATION: n is a, c, g, t or u
<220> FEATURE:
<221> NAME/KEY: misc_feature
```

```
<222> LOCATION: (2856)..(2856)
<223> OTHER INFORMATION: n is a, c, g, t or u
<220> FEATURE:
<221> NAME/KEY: misc_feature
<222> LOCATION: (2884)..(2884)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2953)..(2953)
<223> OTHER INFORMATION: n is a, c, g, t or u
<220> FEATURE:
<221> NAME/KEY: misc_feature
<222> LOCATION: (2994)..(2994)
<223> OTHER INFORMATION: n is a, c, g, t or u
<220> FEATURE:
<221> NAME/KEY: misc_feature
<222> LOCATION: (3022)..(3022)
<223> OTHER INFORMATION: n is a, c, g, t or u
<220> FEATURE:
<221> NAME/KEY: misc_feature
<222> LOCATION: (3063)..(3063)
<223> OTHER INFORMATION: n is a, c, g, t or u
<220> FEATURE:
<221> NAME/KEY: misc_feature
<222> LOCATION: (3091)..(3091)
<223> OTHER INFORMATION: n is a, c, g, t or u
<220> FEATURE:
<221> NAME/KEY: misc_feature
<222> LOCATION: (3132)..(3132)
<223> OTHER INFORMATION: n is a, c, g, t or u
<220> FEATURE:
<221> NAME/KEY: misc_feature
<222> LOCATION: (3158)..(3158)
<223> OTHER INFORMATION: n is a, c, g, t or u

<400> SEQUENCE: 31
atggccggag tgttcacact ggaggacttc gtgggcgact ggagacagac cgccggctac        60
aacctggacc aggtgctgga gcagggcgga gtgagcagcc tgtttcagaa cctgggcgtg       120
agcgtcaccc ccatccagag gatcgtgctg tccggcgaga atggcctgaa gatcgacatc       180
cacgtcatca tcccctacga gggcctgagc ggcgatcaga tgggccagat cgagaagatc       240
ttcaaggtgg tgtatcccgt cgacgaccac cacttcaagg tgatcctgca ttacggcacc       300
ctcgtgatcg acggcgtgac ccctaacatg atcgactact tcggcaggcc ctacgaggga       360
atcgccgtgt cgacggaaa gaagatcacc gtgaccggca ccctgtggaa cggaaacaag       420
atcatcgacg agaggctgat caaccccgac ggctccctgc tgttcagggt gaccatcaat       480
ggcgtgaccg gctggagact gtgcgagaga atcctggccg gaggcggagg aagcctcgtg       540
cccagaggat ccggcggagg cggctccagc cggctccata tgggaaactc cgtggtcaca       600
tacaacacca acatcgacca gctgtgcaag agcggcaaga tcgaggaggc cctgaagctg       660
ttcaaggaga tggaggagaa gggcatcacc cccagcgtgg tcacatacac cacactgatc       720
gacggactgt gtaaagccgg cgacgtggac gaagccctcg agctgttcaa agagatgcgg       780
agcaagggcg tgaagcccaa cgtggtgaca tacaccaccc tgatcgacgg cctgtgcaag       840
gccggcaaag tggacgaggc cctggagctg ttcgacgaga tgaaggagag gggcatcaag       900
cccgacgtgg tcacatacaa caccctgatc gacggcctgt gcaagagcgg caagatcgag       960
gaggccctga agctgttcaa ggagatggag gagaagggca tcaccccag cgtggttaca      1020 tacaccacac tgatcgacgg actgtgtaaa gccggcgacg tggacgaagc cctcgagctg      1080
ttcaaagaga tgcggagcaa gggcgtgaag cccaacgtgg tcacatacac caccctgatc      1140
```

```
gacggcctgt gcaaggccgg caaggtggat gaggccctgg agctgttcga cgagatgaag        1200
gagaggggca tcaagcccga cgtggttaca tacaacaccc tgatcgacgg cctgtgcaag        1260
agcggcaaga tcgaggaggc cctgaagctg ttcaaggaga tggaggagaa gggcatcacc        1320
cccagcgtgg tcacatacac cacactgatc gacggactgt gtaaagccgg cgacgtggac        1380
gaagccctcg agctgttcaa agagatgcgg agcaagggcg tgaagcccaa cgtggtgaca        1440
tacaccaccc tgatcgacgg cctgtgcaag gccggcaaag tggacgaggc cctggagctg        1500
ttcgacgaga tgaaggagag gggcatcaag cccgacgtgg tcacatacaa caccctgatc        1560
gacggcctgt gcaagagcgg caagatcgag gaggccctga agctgttcaa ggagatggag        1620
gagaagggca tcaccccag cgtggttaca tacaccacac tgatcgacgg actgtgtaaa        1680
gccggcgacg tggacgaagc cctcgagctg ttcaaagaga tgcggagcaa gggcgtgaag        1740
cccaacgtgg tcacatacac caccctgatc gacggcctgt gcaaggccgg caaggtggat        1800
gaggccctgg agctgttcga cgagatgaag gagaggggca tcaagcccga cgtggtcaca        1860
tacaacaccc tgatcgacgg cctgtgcaag agcggcaaga tcgaggaggc cctgaagctg        1920
ttcaaggaga tggaggagaa gggcatcacc cccagcgtgg tcacatacac cacactgatc        1980
gacggactgt gtaaagccgg cgacgtggac gaagccctcg agctgttcaa agagatgcgg        2040
agcaagggcg tgaagcccaa cgtggttaca taccaccccc tgatcgacgg cctgtgcaag        2100
gccggcaaag tggacgaggc cctggagctg ttcgacgaga tgaaggagag gggcatcaag        2160
cccgacgtgg tcacatacaa caccctgatc gacggcctgt gcaagagcgg caagatcgag        2220
gaggccctga agctgttcaa ggagatggag gagaagggca tcaccccag cgtggtgaca        2280 tacaccacac tgatcgacgg actgtgtaaa gccggcgacg tggacgaagc cctcgagctg        2340
ttcaaagaga tgcggagcaa gggcgtgaag cccaacgtgg tcacatacac caccctgatc        2400
gacggcctgt gcaaggccgg caaggtggat gaggccctgg agctgttcga cgagatgaag        2460
gagaggggca tcaagcccga cgagctgacc tacaacaccc tgatcagcgg cctgggcaag        2520
gccggcagag ccagagaccc ccccgtgctc agtagcggct ccggcggcag cggggaggc        2580 gggcatcatc accatcacca cggacgctag magvtdvgdw rtagyndvgg vssngvsvtr        2640
vsgngkdhvy gsgdmgkkvv yvddhhkvhy gtvdgvtnmd ygrygavdgk ktvtgtwngn        2700
kdrndgsrvt ngvtgwrcra ggggsvrgsg gggssrhmgn svvtyntndc ksgkakkmkg        2760
tsvvtyttdg ckagdvdakm rskgvknvvt yttdgckagk vdadmkrgkd vvtyntdgck        2820
sgkakkmkgt svvtyttdgc kagdvdakmr skgvknvvty ttdgckagkv dadmkrgkdv        2880
vtyntdgcks gkakkmkgts vvtyttdgck agdvdakmrs kgvknvvtyt tdgckagkvd        2940
admkrgkdvv tyntdgcksg kakkmkgtsv vtyttdgcka gdvdakmrsk gvknvvtytt        3000
dgckagkvda dmkrgkdvvt yntdgcksgk akkmkgtsvv tyttdgckag dvdakmrskg        3060
vknvvtyttd gckagkvdad mkrgkdvvty ntdgcksgka kkmkgtsvvt yttdgckagd        3120
vdakmrskgv knvvtyttdg ckagkvdadm krgkdtynts ggkagrardv ssgsggsggg        3180 ghhhhhhgr                                                              3189
```

<210> SEQ ID NO 32
<211> LENGTH: 3189
<212> TYPE: DNA
<213> ORGANISM: Artificial sequence
<220> FEATURE:
<223> OTHER INFORMATION: NL_PPRcag_4
<220> FEATURE:
<221> NAME/KEY: misc_feature -continued

```
<222> LOCATION: (2626)..(2626)
<223> OTHER INFORMATION: n is a, c, g, t or u
<220> FEATURE:
<221> NAME/KEY: misc_feature
<222> LOCATION: (2634)..(2634)
<223> OTHER INFORMATION: n is a, c, g, t or u
<220> FEATURE:
<221> NAME/KEY: misc_feature
<222> LOCATION: (2644)..(2644)
<223> OTHER INFORMATION: n is a, c, g, t or u
<220> FEATURE:
<221> NAME/KEY: misc_feature
<222> LOCATION: (2678)..(2678)
<223> OTHER INFORMATION: n is a, c, g, t or u
<220> FEATURE:
<221> NAME/KEY: misc_feature
<222> LOCATION: (2698)..(2698)
<223> OTHER INFORMATION: n is a, c, g, t or u
<220> FEATURE:
<221> NAME/KEY: misc_feature
<222> LOCATION: (2700)..(2700)
<223> OTHER INFORMATION: n is a, c, g, t or u
<220> FEATURE:
<221> NAME/KEY: misc_feature
<222> LOCATION: (2704)..(2704)
<223> OTHER INFORMATION: n is a, c, g, t or u
<220> FEATURE:
<221> NAME/KEY: misc_feature
<222> LOCATION: (2711)..(2711)
<223> OTHER INFORMATION: n is a, c, g, t or u
<220> FEATURE:
<221> NAME/KEY: misc_feature
<222> LOCATION: (2740)..(2740)
<223> OTHER INFORMATION: n is a, c, g, t or u
<220> FEATURE:
<221> NAME/KEY: misc_feature
<222> LOCATION: (2746)..(2746)
<223> OTHER INFORMATION: n is a, c, g, t or u
<220> FEATURE:
<221> NAME/KEY: misc_feature
<222> LOCATION: (2748)..(2748)
<223> OTHER INFORMATION: n is a, c, g, t or u
<220> FEATURE:
<221> NAME/KEY: misc_feature
<222> LOCATION: (2787)..(2787)
<223> OTHER INFORMATION: n is a, c, g, t or u
<220> FEATURE:
<221> NAME/KEY: misc_feature
<222> LOCATION: (2815)..(2815)
<223> OTHER INFORMATION: n is a, c, g, t or u
<220> FEATURE:
<221> NAME/KEY: misc_feature
<222> LOCATION: (2856)..(2856)
<223> OTHER INFORMATION: n is a, c, g, t or u
<220> FEATURE:
<221> NAME/KEY: misc_feature
<222> LOCATION: (2884)..(2884)
<223> OTHER INFORMATION: n is a, c, g, t or u
<220> FEATURE:
<221> NAME/KEY: misc_feature
<222> LOCATION: (2925)..(2925)
<223> OTHER INFORMATION: n is a, c, g, t or u
<220> FEATURE:
<221> NAME/KEY: misc_feature
<222> LOCATION: (2953)..(2953)
<223> OTHER INFORMATION: n is a, c, g, t or u
<220> FEATURE:
<221> NAME/KEY: misc_feature
<222> LOCATION: (2994)..(2994)
<223> OTHER INFORMATION: n is a, c, g, t or u
<220> FEATURE:
<221> NAME/KEY: misc_feature
<222> LOCATION: (3022)..(3022)
<223> OTHER INFORMATION: n is a, c, g, t or u
<220> FEATURE:
<221> NAME/KEY: misc_feature
<222> LOCATION: (3063)..(3063)
<223> OTHER INFORMATION: n is a, c, g, t or u
<220> FEATURE:
```

<221> NAME/KEY: misc_feature
<222> LOCATION: (3091)..(3091)
<223> OTHER INFORMATION: n is a, c, g, t or u
<220> FEATURE:
<221> NAME/KEY: misc_feature
<222> LOCATION: (3132)..(3132)
<223> OTHER INFORMATION: n is a, c, g, t or u
<220> FEATURE:
<221> NAME/KEY: misc_feature
<222> LOCATION: (3158)..(3158)
<223> OTHER INFORMATION: n is a, c, g, t or u

<400> SEQUENCE: 32

```
atggccggag tgttcacact ggaggacttc gtgggcgact ggagacagac cgccggctac      60
aacctggacc aggtgctgga gcagggcgga gtgagcagcc tgtttcagaa cctgggcgtg     120
agcgtcaccc ccatccagag gatcgtgctg tccggcgaga atggcctgaa gatcgacatc     180
cacgtcatca tcccctacga gggcctgagc ggcgatcaga tgggccagat cgagaagatc     240
ttcaaggtgg tgtatcccgt cgacgaccac cacttcaagg tgatcctgca ttacggcacc     300
ctcgtgatcg acggcgtgac ccctaacatg atcgactact cggcaggcc  ctacgaggga     360 atcgccgtgt cgacggaaa  gaagatcacc gtgaccggca ccctgtggaa cggaaacaag     420
atcatcgacg agaggctgat caaccccgac ggctccctgc tgttcagggt gaccatcaat     480
ggcgtgaccg gctggagact gtgcgagaga atcctggccg gaggcggagg aagcctcgtg     540
cccagaggat ccggcggagg cggctccagc cggctccata tgggaaactc cgtggtcaca     600
tacaacacca acatcgacga actgtgcaag agcggcaaga tcgaggaggc cctgaagctg     660
ttcaaggaga tggaggagaa gggcatcacc cccagcgtgg tcacatacac cacactgatc     720
gacggactgt gtaaagccgg cgacgtggac gaagccctcg agctgttcaa agagatgcgg     780
agcaagggcg tgaagcccaa cgtggtgaca tacaccaccc tgatcgacgg cctgtgcaag     840
gccggcaaag tggacgaggc cctggagctg ttcgacgaga tgaaggagag gggcatcaag     900
cccgacgtgg tcacatacaa caccctgatc gacggcctgt gcaagagcgg caagatcgag     960
gaggccctga gctgttcaa  ggagatggag gagaagggca tcaccccag  cgtggttaca    1020 tacaccacac tgatcgacgg actgtgtaaa gccggcgacg tggacgaagc cctcgagctg    1080
ttcaaagaga tgcggagcaa gggcgtgaag cccaacgtgg tcacatacac caccctgatc    1140
gacggcctgt gcaaggccgg caaggtggat gaggccctgg agctgttcga cgagatgaag    1200
gagaggggca tcaagcccga cgtggttaca tacaacaccc tgatcgacgg cctgtgcaag    1260
agcggcaaga tcgaggaggc cctgaagctg ttcaaggaga tggaggagaa gggcatcacc    1320
cccagcgtgg tcacatacac cacactgatc gacggactgt gtaaagccgg cgacgtggac    1380
gaagccctcg agctgttcaa agagatgcgg agcaagggcg tgaagcccaa cgtggtgaca    1440
tacaccaccc tgatcgacgg cctgtgcaag gccggcaaag tggacgaggc cctggagctg    1500
ttcgacgaga tgaaggagag gggcatcaag cccgacgtgg tcacatacaa caccctgatc    1560
gacggcctgt gcaagagcgg caagatcgag gaggccctga gctgttcaa  ggagatggag    1620 gagaagggca tcaccccag  cgtggttaca tacaccacac tgatcgacgg actgtgtaaa    1680
gccggcgacg tggacgaagc cctcgagctg ttcaaagaga tgcggagcaa gggcgtgaag    1740
cccaacgtgg tcacatacac caccctgatc gacggcctgt gcaaggccgg caaggtggat    1800
gaggccctgg agctgttcga cgagatgaag gagaggggca tcaagcccga cgtggtcaca    1860
tacaacaccc tgatcgacgg cctgtgcaag agcggcaaga tcgaggaggc cctgaagctg    1920
ttcaaggaga tggaggagaa gggcatcacc cccagcgtgg tcacatacac cacactgatc    1980
```

```
gacggactgt gtaaagccgg cgacgtggac gaagccctcg agctgttcaa agagatgcgg      2040
agcaagggcg tgaagcccaa cgtggttaca tacaccaccc tgatcgacgg cctgtgcaag      2100
gccggcaaag tggacgaggc cctggagctg ttcgacgaga tgaaggagag gggcatcaag      2160
cccgacgtgg tcacatacaa caccctgatc gacggcctgt gcaagagcgg caagatcgag      2220
gaggccctga agctgttcaa ggagatggag gagaagggca tcacccccag cgtggtgaca      2280
tacaccacac tgatcgacgg actgtgtaaa gccggcgacg tggacgaagc cctcgagctg      2340
ttcaaagaga tgcggagcaa gggcgtgaag cccaacgtgg tcacatacac caccctgatc      2400
gacggcctgt gcaaggccgg caaggtggat gaggccctgg agctgttcga cgagatgaag      2460
gagaggggca tcaagcccga cgagctgacc tacaacaccc tgatcagcgg cctgggcaag      2520
gccggcagag ccagagaccc ccccgtgctc agtagcggct ccggcggcag cggggggaggc      2580 gggcatcatc accatcacca cggacgctag magvtdvgdw rtagyndvgg vssngvsvtr      2640
vsgngkdhvy gsgdmgkkvv yvddhhkvhy gtvdgvtnmd ygrygavdgk ktvtgtwngn      2700
kdrndgsrvt ngvtgwrcra ggggsvrgsg gggssrhmgn svvtyntndc ksgkakkmkg      2760
tsvvtyttdg ckagdvdakm rskgvknvvt yttdgckagk vdadmkrgkd vvtyntdgck      2820
sgkakkmkgt svvtyttdgc kagdvdakmr skgvknvvty ttdgckagkv dadmkrgkdv      2880
vtyntdgcks gkakkmkgts vvtyttdgck agdvdakmrs kgvknvvtyt tdgckagkvd      2940
admkrgkdvv tyntdgcksg kakkmkgtsv vtyttdgcka gdvdakmrsk gvknvvtytt      3000
dgckagkvda dmkrgkdvvt yntdgcksgk akkmkgtsvv tyttdgckag dvdakmrskg      3060
vknvvtyttd gckagkvdad mkrgkdvvty ntdgcksgka kkmkgtsvvt yttdgckagd      3120
vdakmrskgv knvvtyttdg ckagkvdadm krgkdtynts ggkagrardv ssgsggsggg      3180 ghhhhhhgr                                                             3189
```

```
<210> SEQ ID NO 33
<211> LENGTH: 3190
<212> TYPE: DNA
<213> ORGANISM: Artificial sequence
<220> FEATURE:
<223> OTHER INFORMATION: NL_PPRcag_5
<220> FEATURE:
<221> NAME/KEY: misc_feature
<222> LOCATION: (2626)..(2626)
<223> OTHER INFORMATION: n is a, c, g, t or u
<220> FEATURE:
<221> NAME/KEY: misc_feature
<222> LOCATION: (2634)..(2634)
<223> OTHER INFORMATION: n is a, c, g, t or u
<220> FEATURE:
<221> NAME/KEY: misc_feature
<222> LOCATION: (2644)..(2644)
<223> OTHER INFORMATION: n is a, c, g, t or u
<220> FEATURE:
<221> NAME/KEY: misc_feature
<222> LOCATION: (2678)..(2678)
<223> OTHER INFORMATION: n is a, c, g, t or u
<220> FEATURE:
<221> NAME/KEY: misc_feature
<222> LOCATION: (2698)..(2698)
<223> OTHER INFORMATION: n is a, c, g, t or u
<220> FEATURE:
<221> NAME/KEY: misc_feature
<222> LOCATION: (2700)..(2700)
<223> OTHER INFORMATION: n is a, c, g, t or u
<220> FEATURE:
<221> NAME/KEY: misc_feature
<222> LOCATION: (2704)..(2704)
<223> OTHER INFORMATION: n is a, c, g, t or u
<220> FEATURE:
```

-continued

```
<221> NAME/KEY: misc_feature
<222> LOCATION: (2711)..(2711)
<223> OTHER INFORMATION: n is a, c, g, t or u
<220> FEATURE:
<221> NAME/KEY: misc_feature
<222> LOCATION: (2740)..(2740)
<223> OTHER INFORMATION: n is a, c, g, t or u
<220> FEATURE:
<221> NAME/KEY: misc_feature
<222> LOCATION: (2746)..(2746)
<223> OTHER INFORMATION: n is a, c, g, t or u
<220> FEATURE:
<221> NAME/KEY: misc_feature
<222> LOCATION: (2748)..(2748)
<223> OTHER INFORMATION: n is a, c, g, t or u
<220> FEATURE:
<221> NAME/KEY: misc_feature
<222> LOCATION: (2788)..(2788)
<223> OTHER INFORMATION: n is a, c, g, t or u
<220> FEATURE:
<221> NAME/KEY: misc_feature
<222> LOCATION: (2816)..(2816)
<223> OTHER INFORMATION: n is a, c, g, t or u
<220> FEATURE:
<221> NAME/KEY: misc_feature
<222> LOCATION: (2857)..(2857)
<223> OTHER INFORMATION: n is a, c, g, t or u
<220> FEATURE:
<221> NAME/KEY: misc_feature
<222> LOCATION: (2885)..(2885)
<223> OTHER INFORMATION: n is a, c, g, t or u
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2954)..(2954)
<223> OTHER INFORMATION: n is a, c, g, t or u
<220> FEATURE:
<221> NAME/KEY: misc_feature
<222> LOCATION: (2995)..(2995)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3064)..(3064)
<223> OTHER INFORMATION: n is a, c, g, t or u
<220> FEATURE:
<221> NAME/KEY: misc_feature
<222> LOCATION: (3092)..(3092)
<223> OTHER INFORMATION: n is a, c, g, t or u
<220> FEATURE:
<221> NAME/KEY: misc_feature
<222> LOCATION: (3133)..(3133)
<223> OTHER INFORMATION: n is a, c, g, t or u
<220> FEATURE:
<221> NAME/KEY: misc_feature
<222> LOCATION: (3159)..(3159)
<223> OTHER INFORMATION: n is a, c, g, t or u

<400> SEQUENCE: 33
atggccggag tgttcacact ggaggacttc gtgggcgact ggagacagac cgccggctac      60
aacctggacc aggtgctgga gcagggcgga gtgagcagcc tgtttcagaa cctgggcgtg     120
agcgtcaccc ccatccagag gatcgtgctg tccggcgaga atggcctgaa gatcgacatc     180
cacgtcatca tccctacga gggcctgagc ggcgatcaga tgggccagat cgagaagatc      240
ttcaaggtgg tgtatcccgt cgacgaccac cacttcaagg tgatcctgca ttacggcacc     300
ctcgtgatcg acggcgtgac ccctaacatg atcgactact cggcaggcc ctacgaggga      360 atcgccgtgt cgacggaaa gaagatcacc gtgaccggca ccctgtggaa cggaaacaag     420
```

```
atcatcgacg agaggctgat caaccccgac ggctccctgc tgttcagggt gaccatcaat      480
ggcgtgaccg gctggagact gtgcgagaga atcctggccg gaggcggagg aagcctcgtg      540
cccagaggat ccggcggagg cggctccagc cggctccata tgggaaactc cgtggtcaca      600
tacaacacca acatcgacaa actgtgcaag agcggcaaga tcgaggaggc cctgaagctg      660
ttcaaggaga tggaggagaa gggcatcacc cccagcgtgg tcacatacac cacactgatc      720
gacggactgt gtaaagccgg cgacgtggac gaagccctcg agctgttcaa agagatgcgg      780
agcaagggcg tgaagcccaa cgtggtgaca tacaccaccc tgatcgacgg cctgtgcaag      840
gccggcaaag tggacgaggc cctggagctg ttcgacgaga tgaaggagag gggcatcaag      900
cccgacgtgg tcacatacaa caccctgatc gacggcctgt gcaagagcgg caagatcgag      960
gaggccctga agctgttcaa ggagatggag gagaagggca tcaccccag cgtggttaca      1020 tacaccacac tgatcgacgg actgtgtaaa gccggcgacg tggacgaagc cctcgagctg      1080
ttcaaagaga tgcggagcaa gggcgtgaag cccaacgtgg tcacatacac caccctgatc      1140
gacggcctgt gcaaggccgg caaggtggat gaggccctgg agctgttcga cgagatgaag      1200
gagaggggca tcaagcccga cgtggttaca tacaacaccc tgatcgacgg cctgtgcaag      1260
agcggcaaga tcgaggaggc cctgaagctg ttcaaggaga tggaggagaa gggcatcacc      1320
cccagcgtgg tcacatacac cacactgatc gacggactgt gtaaagccgg cgacgtggac      1380
gaagccctcg agctgttcaa agagatgcgg agcaagggcg tgaagcccaa cgtggtgaca      1440
tacaccaccc tgatcgacgg cctgtgcaag gccggcaaag tggacgaggc cctggagctg      1500
ttcgacgaga tgaaggagag gggcatcaag cccgacgtgg tcacatacaa caccctgatc      1560
gacggcctgt gcaagagcgg caagatcgag gaggccctga agctgttcaa ggagatggag      1620
gagaagggca tcaccccag cgtggttaca tacaccacac tgatcgacgg actgtgtaaa      1680
gccggcgacg tggacgaagc cctcgagctg ttcaaagaga tgcggagcaa gggcgtgaag      1740
cccaacgtgg tcacatacac caccctgatc gacggcctgt gcaaggccgg caaggtggat      1800
gaggccctgg agctgttcga cgagatgaag gagaggggca tcaagcccga cgtggtcaca      1860
tacaacaccc tgatcgacgg cctgtgcaag agcggcaaga tcgaggaggc cctgaagctg      1920
ttcaaggaga tggaggagaa gggcatcacc cccagcgtgg tcacatacac cacactgatc      1980
gacggactgt gtaaagccgg cgacgtggac gaagccctcg agctgttcaa agagatgcgg      2040
agcaagggcg tgaagcccaa cgtggttaca tacaccaccc tgatcgacgg cctgtgcaag      2100
gccggcaaag tggacgaggc cctggagctg ttcgacgaga tgaaggagag gggcatcaag      2160
cccgacgtgg tcacatacaa caccctgatc gacggcctgt gcaagagcgg caagatcgag      2220
gaggccctga agctgttcaa ggagatggag gagaagggca tcaccccag cgtggtgaca      2280 tacaccacac tgatcgacgg actgtgtaaa gccggcgacg tggacgaagc cctcgagctg      2340
ttcaaagaga tgcggagcaa gggcgtgaag cccaacgtgg tcacatacac caccctgatc      2400
gacggcctgt gcaaggccgg caaggtggat gaggccctgg agctgttcga cgagatgaag      2460
gagaggggca tcaagcccga cgagctgacc tacaacaccc tgatcagcgg cctgggcaag      2520
gccggcagag ccagagaccc ccccgtgctc agtagcggct ccggcggcag cggggggaggc      2580 gggcatcatc accatcacca cggacgctag magvtdvgdw rtagyndvgg vssngvsvtr      2640
vsgngkdhvy gsgdmgkkvv yvddhhkvhy gtvdgvtnmd ygrygavdgk ktvtgtwngn      2700
kdrndgsrvt ngvtgwrcra ggggsvrgsg gggssrhmgn svvtyntndk cksgkakkmk      2760
```

```
gtsvvtyttd gckagdvdak mrskgvknvv tyttdgckag kvdadmkrgk dvvtyntdgc      2820
ksgkakkmkg tsvvtyttdg ckagdvdakm rskgvknvvt yttdgckagk vdadmkrgkd      2880
vvtyntdgck sgkakkmkgt svvtyttdgc kagdvdakmr skgvknvvty ttdgckagkv      2940
dadmkrgkdv vtyntdgcks gkakkmkgts vvtyttdgck agdvdakmrs kgvknvvtyt      3000
tdgckagkvd admkrgkdvv tyntdgcksg kakkmkgtsv vtyttdgcka gdvdakmrsk      3060
gvknvvtytt dgckagkvda dmkrgkdvvt yntdgcksgk akkmkgtsvv tyttdgckag      3120
dvdakmrskg vknvvtyttd gckagkvdad mkrgkdtynt sggkagrard vssgsggsgg      3180 gghhhhhhgr                                                            3190

<210> SEQ ID NO 34
<211> LENGTH: 3190
<212> TYPE: DNA
<213> ORGANISM: Artificial sequence
<220> FEATURE:
<223> OTHER INFORMATION: NL_PPRcag_1
<220> FEATURE:
<221> NAME/KEY: misc_feature
<222> LOCATION: (2626)..(2626)
<223> OTHER INFORMATION: n is a, c, g, t or u
<220> FEATURE:
<221> NAME/KEY: misc_feature
<222> LOCATION: (2634)..(2634)
<223> OTHER INFORMATION: n is a, c, g, t or u
<220> FEATURE:
<221> NAME/KEY: misc_feature
<222> LOCATION: (2644)..(2644)
<223> OTHER INFORMATION: n is a, c, g, t or u
<220> FEATURE:
<221> NAME/KEY: misc_feature
<222> LOCATION: (2678)..(2678)
<223> OTHER INFORMATION: n is a, c, g, t or u
<220> FEATURE:
<221> NAME/KEY: misc_feature
<222> LOCATION: (2698)..(2698)
<223> OTHER INFORMATION: n is a, c, g, t or u
<220> FEATURE:
<221> NAME/KEY: misc_feature
<222> LOCATION: (2700)..(2700)
<223> OTHER INFORMATION: n is a, c, g, t or u
<220> FEATURE:
<221> NAME/KEY: misc_feature
<222> LOCATION: (2704)..(2704)
<223> OTHER INFORMATION: n is a, c, g, t or u
<220> FEATURE:
<221> NAME/KEY: misc_feature
<222> LOCATION: (2711)..(2711)
<223> OTHER INFORMATION: n is a, c, g, t or u
<220> FEATURE:
<221> NAME/KEY: misc_feature
<222> LOCATION: (2740)..(2740)
<223> OTHER INFORMATION: n is a, c, g, t or u
<220> FEATURE:
<221> NAME/KEY: misc_feature
<222> LOCATION: (2746)..(2746)
<223> OTHER INFORMATION: n is a, c, g, t or u
<220> FEATURE:
<221> NAME/KEY: misc_feature
<222> LOCATION: (2788)..(2788)
<223> OTHER INFORMATION: n is a, c, g, t or u
<220> FEATURE:
<221> NAME/KEY: misc_feature
<222> LOCATION: (2816)..(2816)
<223> OTHER INFORMATION: n is a, c, g, t or u
<220> FEATURE:
<221> NAME/KEY: misc_feature
<222> LOCATION: (2857)..(2857)
<223> OTHER INFORMATION: n is a, c, g, t or u
<220> FEATURE:
<221> NAME/KEY: misc_feature
<222> LOCATION: (2885)..(2885)
<223> OTHER INFORMATION: n is a, c, g, t or u
```

```
<220> FEATURE:
<221> NAME/KEY: misc_feature
<222> LOCATION: (2926)..(2926)
<223> OTHER INFORMATION: n is a, c, g, t or u
<220> FEATURE:
<221> NAME/KEY: misc_feature
<222> LOCATION: (2954)..(2954)
<223> OTHER INFORMATION: n is a, c, g, t or u
<220> FEATURE:
<221> NAME/KEY: misc_feature
<222> LOCATION: (2995)..(2995)
<223> OTHER INFORMATION: n is a, c, g, t or u
<220> FEATURE:
<221> NAME/KEY: misc_feature
<222> LOCATION: (3023)..(3023)
<223> OTHER INFORMATION: n is a, c, g, t or u
<220> FEATURE:
<221> NAME/KEY: misc_feature
<222> LOCATION: (3064)..(3064)
<223> OTHER INFORMATION: n is a, c, g, t or u
<220> FEATURE:
<221> NAME/KEY: misc_feature
<222> LOCATION: (3092)..(3092)
<223> OTHER INFORMATION: n is a, c, g, t or u
<220> FEATURE:
<221> NAME/KEY: misc_feature
<222> LOCATION: (3133)..(3133)
<223> OTHER INFORMATION: n is a, c, g, t or u
<220> FEATURE:
<221> NAME/KEY: misc_feature
<222> LOCATION: (3159)..(3159)
<223> OTHER INFORMATION: n is a, c, g, t or u

<400> SEQUENCE: 34
atggccggag tgttcacact ggaggacttc gtgggcgact ggagacagac cgccggctac      60
aacctggacc aggtgctgga gcagggcgga gtgagcagcc tgtttcagaa cctgggcgtg     120
agcgtcaccc ccatccagag gatcgtgctg tccggcgaga atggcctgaa gatcgacatc     180
cacgtcatca tcccctacga gggcctgagc ggcgatcaga tgggccagat cgagaagatc     240
ttcaaggtgg tgtatcccgt cgacgaccac cacttcaagg tgatcctgca ttacggcacc     300
ctcgtgatcg acggcgtgac ccctaacatg atcgactact cggcaggcc ctacgaggga     360 atcgccgtgt tcgacggaaa gaagatcacc gtgaccggca ccctgtggaa cggaaacaag     420
atcatcgacg agaggctgat caaccccgac ggctccctgc tgttcagggt gaccatcaat     480
ggcgtgaccg gctggagact gtgcgagaga atcctggccg gaggcggagg aagcctcgtg     540
cccagaggat ccggcggagg cggctccagc cggctccata tgggaaactc cgtggtcaca     600
tacaacaccg atatcgacgg cctgtgcaag agcggcaaga tcgaggaggc cctgaagctg     660
ttcaaggaga tggaggagaa gggcatcacc cccagcgtgg tcacatacac cacactgatc     720
gacggactgt gtaaagccgg cgacgtggac gaagccctcg agctgttcaa agagatgcgg     780
agcaagggcg tgaagcccaa cgtggtgaca tacaccaccc tgatcgacgg cctgtgcaag     840
gccggcaaag tggacgaggc cctggagctg ttcgacgaga tgaaggagag gggcatcaag     900
cccgacgtgg tcacatacaa caccctgatc gacggcctgt gcaagagcgg caagatcgag     960
gaggccctga agctgttcaa ggagatggag gagaagggca tcaccccag cgtggttaca    1020 tacaccacac tgatcgacgg actgtgtaaa gccggcgacg tggacgaagc cctcgagctg    1080
ttcaaagaga tgcggagcaa gggcgtgaag cccaacgtgg tcacatacac caccctgatc    1140
gacggcctgt gcaaggccgg caaggtggat gaggccctgg agctgttcga cgagatgaag    1200 gagagggca tcaagcccga cgtggttaca tacaacaccc tgatcgacgg cctgtgcaag    1260
agcggcaaga tcgaggaggc cctgaagctg ttcaaggaga tggaggagaa gggcatcacc    1320
```

```
cccagcgtgg tcacatacac cacactgatc gacggactgt gtaaagccgg cgacgtggac      1380
gaagccctcg agctgttcaa agagatgcgg agcaagggcg tgaagcccaa cgtggtgaca      1440
tacaccaccc tgatcgacgg cctgtgcaag gccggcaaag tggacgaggc cctggagctg      1500
ttcgacgaga tgaaggagag gggcatcaag cccgacgtgg tcacatacaa caccctgatc      1560
gacggcctgt gcaagagcgg caagatcgag gaggccctga agctgttcaa ggagatggag      1620
gagaagggca tcaccccag cgtggttaca tacaccacac tgatcgacgg actgtgtaaa      1680
gccggcgacg tggacgaagc cctcgagctg ttcaaagaga tgcggagcaa gggcgtgaag      1740
cccaacgtgg tcacatacac caccctgatc gacggcctgt gcaaggccgg caaggtggat      1800
gaggccctgg agctgttcga cgagatgaag gagaggggca tcaagcccga cgtggtcaca      1860
tacaacaccc tgatcgacgg cctgtgcaag agcggcaaga tcgaggaggc cctgaagctg      1920
ttcaaggaga tggaggagaa gggcatcacc cccagcgtgg tcacatacac cacactgatc      1980
gacggactgt gtaaagccgg cgacgtggac gaagccctcg agctgttcaa agagatgcgg      2040
agcaagggcg tgaagcccaa cgtggttaca tacaccaccc tgatcgacgg cctgtgcaag      2100
gccggcaaag tggacgaggc cctggagctg ttcgacgaga tgaaggagag gggcatcaag      2160
cccgacgtgg tcacatacaa caccctgatc gacggcctgt gcaagagcgg caagatcgag      2220
gaggccctga agctgttcaa ggagatggag gagaagggca tcaccccag cgtggtgaca      2280 tacaccacac tgatcgacgg actgtgtaaa gccggcgacg tggacgaagc cctcgagctg      2340
ttcaaagaga tgcggagcaa gggcgtgaag cccaacgtgg tcacatacac caccctgatc      2400
gacggcctgt gcaaggccgg caaggtggat gaggccctgg agctgttcga cgagatgaag      2460
gagaggggca tcaagcccga cgagctgacc tacaacaccc tgatcagcgg cctgggcaag      2520
gccggcagag ccagagaccc ccccgtgctc agtagcggct ccggcggcag cggggggaggc     2580 gggcatcatc accatcacca cggacgctag magvtdvgdw rtagyndvgg vssngvsvtr     2640
vsgngkdhvy gsgdmgkkvv yvddhhkvhy gtvdgvtnmd ygrygavdgk ktvtgtwngn     2700
kdrndgsrvt ngvtgwrcra ggggsvrgsg gggssrhmgn svvtyntddg cksgkakkmk     2760
gtsvvtyttd gckagdvdak mrskgvknvv tyttdgckag kvdadmkrgk dvvtyntdgc     2820
ksgkakkmkg tsvvtyttdg ckagdvdakm rskgvknvvt yttdgckagk vdadmkrgkd     2880
vvtyntdgck sgkakkmkgt svvtyttdgc kagdvdakmr skgvknvvty ttdgckagkv     2940
dadmkrgkdv vtyntdgcks gkakkmkgts vvtyttdgck agdvdakmrs kgvknvvtyt     3000
tdgckagkvd admkrgkdvv tyntdgcksg kakkmkgtsv vtyttdgcka gdvdakmrsk     3060
gvknvvtytt dgckagkvda dmkrgkdvvt yntdgcksgk akkmkgtsvv tyttdgckag     3120
dvdakmrskg vknvvtyttd gckagkvdad mkrgkdtynt sggkagrard vssgsggsgg     3180 gghhhhhhgr                                                            3190
```

<210> SEQ ID NO 35
<211> LENGTH: 1066
<212> TYPE: DNA
<213> ORGANISM: Artificial sequence
<220> FEATURE:
<223> OTHER INFORMATION: GFPnls
<220> FEATURE:
<221> NAME/KEY: misc_feature
<222> LOCATION: (878)..(878)
<223> OTHER INFORMATION: n is a, c, g, t or u
<220> FEATURE:
<221> NAME/KEY: misc_feature
<222> LOCATION: (934)..(934)
<223> OTHER INFORMATION: n is a, c, g, t or u

```
<220> FEATURE:
<221> NAME/KEY: misc_feature
<222> LOCATION: (946)..(946)
<223> OTHER INFORMATION: n is a, c, g, t or u
<220> FEATURE:
<221> NAME/KEY: misc_feature
<222> LOCATION: (954)..(954)
<223> OTHER INFORMATION: n is a, c, g, t or u
<220> FEATURE:
<221> NAME/KEY: misc_feature
<222> LOCATION: (959)..(959)
<223> OTHER INFORMATION: n is a, c, g, t or u
<220> FEATURE:
<221> NAME/KEY: misc_feature
<222> LOCATION: (961)..(961)
<223> OTHER INFORMATION: n is a, c, g, t or u
<220> FEATURE:
<221> NAME/KEY: misc_feature
<222> LOCATION: (964)..(964)
<223> OTHER INFORMATION: n is a, c, g, t or u
<220> FEATURE:
<221> NAME/KEY: misc_feature
<222> LOCATION: (972)..(972)
<223> OTHER INFORMATION: n is a, c, g, t or u
<220> FEATURE:
<221> NAME/KEY: misc_feature
<222> LOCATION: (976)..(976)
<223> OTHER INFORMATION: n is a, c, g, t or u
<220> FEATURE:
<221> NAME/KEY: misc_feature
<222> LOCATION: (980)..(980)
<223> OTHER INFORMATION: n is a, c, g, t or u
<220> FEATURE:
<221> NAME/KEY: misc_feature
<222> LOCATION: (989)..(989)
<223> OTHER INFORMATION: n is a, c, g, t or u
<220> FEATURE:
<221> NAME/KEY: misc_feature
<222> LOCATION: (996)..(996)
<223> OTHER INFORMATION: n is a, c, g, t or u
<220> FEATURE:
<221> NAME/KEY: misc_feature
<222> LOCATION: (1006)..(1006)
<223> OTHER INFORMATION: n is a, c, g, t or u

<400> SEQUENCE: 35
atggccggag tgagcaaggg cgaggagctg ttcaccgggg tggtgcccat cctggtcgag      60
ctggacggcg acgtaaacgg ccacaagttc agcgtgtccg gcgagggcga gggcgatgcc     120
acctacggca agctgaccct gaagttcatc tgcaccaccg gcaagctgcc cgtgccctgg     180
cccaccctcg tgaccaccct gacctacggc gtgcagtgct tcagccgcta ccccgaccac     240
atgaagcagc acgacttctt caagtccgcc atgcccgaag ctacgtcca ggagcgcacc      300 atcttcttca aggacgacgg caactacaag acccgcgccg aggtgaagtt cgagggcgac     360
accctggtga accgcatcga gctgaagggc atcgacttca aggaggacgg caacatcctg     420
gggcacaagc tggagtacaa ctacaacagc cacaacgtct atatcatggc cgacaagcag     480
aagaacggca tcaaggtgaa cttcaagatc cgccacaaca tcgaggacgg cagcgtgcag     540
ctcgccgacc actaccagca gaacaccccc atcggcgacg gccccgtgct gctgcccgac     600
aaccactacc tgagcaccca gtccgccctg agcaaagacc ccaacgagaa gcgcgatcac     660
atggtcctgc tggagttcgt gaccgccgcc gggatcactc tcggcatgga cgagctgtac     720
aagccaaaga aaaagagaaa ggttagccat ggctccggcg gcagcggggg aggtagcggg     780
gactataagg accacgacgg agactacaag gatcatgata ttgattacaa agacgatgac     840
gataagatgg ccggacgcta gmagvskgtg vvvdgdvngh ksvsgggdat ygktkcttgk     900
vwtvtttygv csrydhmkhd ksamgyvrtk ddgnyktrav kgdtvnrkgd kdgnghkyny     960
```

```
nshnvymadk kngkvnkrhn dgsvadhynt gdgvdnhyst saskdnkrdh mvvtaagtgm    1020
dykkkkrkvs hgsggsgggs gdykdhdgdy kdhddykddd dkmagr                   1066

<210> SEQ ID NO 36
<211> LENGTH: 1170
<212> TYPE: DNA
<213> ORGANISM: Artificial sequence
<220> FEATURE:
<223> OTHER INFORMATION: mClover3nls
<220> FEATURE:
<221> NAME/KEY: misc_feature
<222> LOCATION: (959)..(959)
<223> OTHER INFORMATION: n is a, c, g, t or u
<220> FEATURE:
<221> NAME/KEY: misc_feature
<222> LOCATION: (972)..(972)
<223> OTHER INFORMATION: n is a, c, g, t or u
<220> FEATURE:
<221> NAME/KEY: misc_feature
<222> LOCATION: (1029)..(1029)
<223> OTHER INFORMATION: n is a, c, g, t or u
<220> FEATURE:
<221> NAME/KEY: misc_feature
<222> LOCATION: (1037)..(1037)
<223> OTHER INFORMATION: n is a, c, g, t or u
<220> FEATURE:
<221> NAME/KEY: misc_feature
<222> LOCATION: (1042)..(1043)
<223> OTHER INFORMATION: n is a, c, g, t or u
<220> FEATURE:
<221> NAME/KEY: misc_feature
<222> LOCATION: (1054)..(1054)
<223> OTHER INFORMATION: n is a, c, g, t or u
<220> FEATURE:
<221> NAME/KEY: misc_feature
<222> LOCATION: (1058)..(1058)
<223> OTHER INFORMATION: n is a, c, g, t or u
<220> FEATURE:
<221> NAME/KEY: misc_feature
<222> LOCATION: (1062)..(1062)
<223> OTHER INFORMATION: n is a, c, g, t or u
<220> FEATURE:
<221> NAME/KEY: misc_feature
<222> LOCATION: (1072)..(1072)
<223> OTHER INFORMATION: n is a, c, g, t or u
<220> FEATURE:
<221> NAME/KEY: misc_feature
<222> LOCATION: (1079)..(1079)
<223> OTHER INFORMATION: n is a, c, g, t or u
<220> FEATURE:
<221> NAME/KEY: misc_feature
<222> LOCATION: (1089)..(1089)
<223> OTHER INFORMATION: n is a, c, g, t or u

<400> SEQUENCE: 36
atggccggag tgtccaaagg cgaggagctg tttaccggcg tcgtgcctat tctggtggag     60
ctggacggcg acgtgaacgg ccacaagttc tccgtgaggg gcgagggcga aggcgatgcc    120
acaaacggca agctgaccct caagttcatc tgcaccactg gtaaactgcc cgttccttgg    180
cccacactgg tgaccacctt cggctacggc gtggcttgtt tctctcgtta ccccgaccat    240
atgaagcagc acgacttctt caagtccgcc atgcccgagg gatacgtgca agaaaggacc    300
atctccttca aggacgatgg cacctacaag accagagccg aggtgaagtt cgagggcgac    360
acactggtga atcgtatcga actgaagggc atcgacttca agaggacggg caacattctg    420
ggccacaagc tggagtacaa cttcaacagc cactacgtgt acatcaccgc cgataagcag    480
aagaactgca tcaaggccaa cttcaagatt cgtcacaacg tggaggatgg ctccgtgcag    540
ctggccgatc actaccagca gaacacaccc atcggcgatg acccgtttt actgcccgac    600 aaccactatt taagccacca gagcaagctg tccaaggacc ccaacgagaa gcgtgatcat    660
```

```
atggtgctgc tcgagtttgt gaccgccgcc ggcatcaccc atggaatgga cgagctgtac      720
aagagccggc tccatatggg atccggcgga ctcagtagcc ccaagaagaa acgcaaagtc      780
gaggatccaa agaagaaaag gaaggttgaa gaccccaaga aaaagaggaa ggtgggttcc      840
gactataagg accacgacgg agactacaag gatcatgata ttgattacaa agacgatgac      900
gataagatgg ccccaaagaa gaagcggaag gtcggacgct agmagvskgt gvvvdgdvng      960
hksvrgggda tngktkcttg kvwtvttgyg vacsrydhmk hdksamgyvr tskddgtykt     1020
ravkgdtvnr kgdkdgnghk ynnshyvyta dkknckankr hnvdgsvadh yntgdgvdnh     1080
yshskskdnk rdhmvvtaag thgmdyksrh mgsggsskkk rkvdkkkrkv dkkkrkvgsd     1140
ykdhdgdykd hddykddddk makkkrkvgr                                       1170
```

```
<210> SEQ ID NO 37
<211> LENGTH: 862
<212> TYPE: DNA
<213> ORGANISM: Artificial sequence
<220> FEATURE:
<223> OTHER INFORMATION: NL control
<220> FEATURE:
<221> NAME/KEY: misc_feature
<222> LOCATION: (674)..(674)
<223> OTHER INFORMATION: n is a, c, g, t or u
<220> FEATURE:
<221> NAME/KEY: misc_feature
<222> LOCATION: (730)..(730)
<223> OTHER INFORMATION: n is a, c, g, t or u
<220> FEATURE:
<221> NAME/KEY: misc_feature
<222> LOCATION: (742)..(742)
<223> OTHER INFORMATION: n is a, c, g, t or u
<220> FEATURE:
<221> NAME/KEY: misc_feature
<222> LOCATION: (750)..(750)
<223> OTHER INFORMATION: n is a, c, g, t or u
<220> FEATURE:
<221> NAME/KEY: misc_feature
<222> LOCATION: (755)..(755)
<223> OTHER INFORMATION: n is a, c, g, t or u
<220> FEATURE:
<221> NAME/KEY: misc_feature
<222> LOCATION: (757)..(757)
<223> OTHER INFORMATION: n is a, c, g, t or u
<220> FEATURE:
<221> NAME/KEY: misc_feature
<222> LOCATION: (760)..(760)
<223> OTHER INFORMATION: n is a, c, g, t or u
<220> FEATURE:
<221> NAME/KEY: misc_feature
<222> LOCATION: (768)..(768)
<223> OTHER INFORMATION: n is a, c, g, t or u
<220> FEATURE:
<221> NAME/KEY: misc_feature
<222> LOCATION: (772)..(772)
<223> OTHER INFORMATION: n is a, c, g, t or u
<220> FEATURE:
<221> NAME/KEY: misc_feature
<222> LOCATION: (776)..(776)
<223> OTHER INFORMATION: n is a, c, g, t or u
<220> FEATURE:
<221> NAME/KEY: misc_feature
<222> LOCATION: (785)..(785)
<223> OTHER INFORMATION: n is a, c, g, t or u
<220> FEATURE:
<221> NAME/KEY: misc_feature
<222> LOCATION: (792)..(792)
<223> OTHER INFORMATION: n is a, c, g, t or u
<220> FEATURE:
<221> NAME/KEY: misc_feature
<222> LOCATION: (802)..(802)
<223> OTHER INFORMATION: n is a, c, g, t or u
```

-continued

```
<400> SEQUENCE: 37
atggccggag tgttcacact ggaggacttc gtgggcgact ggagacagac cgccggctac      60
aacctggacc aggtgctgga gcagggcgga gtgagcagcc tgtttcagaa cctgggcgtg     120
agcgtcaccc ccatccagag gatcgtgctg tccggcgaga atggcctgaa gatcgacatc     180
cacgtcatca tcccctacga gggcctgagc ggcgatcaga tgggccagat cgagaagatc     240
ttcaaggtgg tgtatcccgt cgacgaccac cacttcaagg tgatcctgca ttacggcacc     300
ctcgtgatcg acggcgtgac ccctaacatg atcgactact cggcaggcc  ctacgaggga     360 atcgccgtgt tcgacggaaa gaagatcacc gtgaccggca ccctgtggaa cggaaacaag     420
atcatcgacg agaggctgat caaccccgac ggctccctgc tgttcagggt gaccatcaat     480
ggcgtgaccg gctggagact gtgcgagaga atcctggccg gaggcggagg aagcctcgtg     540
cccagaggat ccggcggagg cggctccagc cggctccata tgggatccgg cggactcagt     600
agcggctccg gcggcagcgg gggaggcggg catcatcacc atcaccacgg acgctagmag     660
vskgtgvvvd gdvnghksvs gggdatygkt kcttgkvwtv tttygvcsry dhmkhdksam     720
gyvrtkddgn yktravkgdt vnrkgdkdgn ghkynynshn vymadkkngk vnkrhndgsv     780
adhyntgdgv dnhystsask dnkrdhmvvt aagtgmdykk kkrkvshgsg gsgggsgdyk     840
dhdgdykdhd dykddddkma gr                                             862

<210> SEQ ID NO 38
<211> LENGTH: 30
<212> TYPE: DNA
<213> ORGANISM: Artificial sequence
<220> FEATURE:
<223> OTHER INFORMATION: RNA probe

<400> SEQUENCE: 38
gacaugccag cagcagcagc agcaggacug                                       30

<210> SEQ ID NO 39
<211> LENGTH: 30
<212> TYPE: DNA
<213> ORGANISM: Artificial sequence
<220> FEATURE:
<223> OTHER INFORMATION: RNA probe

<400> SEQUENCE: 39
gacaugccgg cggcggcggc ggcgggacug                                       30

<210> SEQ ID NO 40
<211> LENGTH: 30
<212> TYPE: DNA
<213> ORGANISM: Artificial sequence
<220> FEATURE:
<223> OTHER INFORMATION: RNA probe

<400> SEQUENCE: 40
gacacugcug cugcugcugc ugcugaugca                                       30

<210> SEQ ID NO 41
<211> LENGTH: 30
<212> TYPE: DNA
<213> ORGANISM: Artificial sequence
<220> FEATURE:
<223> OTHER INFORMATION: RNA probe

<400> SEQUENCE: 41
gacaccgccg ccgccgccgc cgccggacug                                       30
```

-continued

```
<210> SEQ ID NO 42
<211> LENGTH: 30
<212> TYPE: DNA
<213> ORGANISM: Artificial sequence
<220> FEATURE:
<223> OTHER INFORMATION: RNA probe

<400> SEQUENCE: 42
gacaugcugg uguaucuugu cuuuagacug                                            30

<210> SEQ ID NO 43
<211> LENGTH: 63
<212> TYPE: DNA
<213> ORGANISM: Artificial sequence
<220> FEATURE:
<223> OTHER INFORMATION: Dest-a

<400> SEQUENCE: 43
gaagacataa actccgtggt cacatacaga gaccaaggtc tcagtggtca catacatgtc         60
ttc                                                                        63

<210> SEQ ID NO 44
<211> LENGTH: 47
<212> TYPE: DNA
<213> ORGANISM: Artificial sequence
<220> FEATURE:
<223> OTHER INFORMATION: Dest-b

<400> SEQUENCE: 44
gaagacatat acagagacca aggtctcagt ggtgacataa tgtcttc                        47

<210> SEQ ID NO 45
<211> LENGTH: 47
<212> TYPE: DNA
<213> ORGANISM: Artificial sequence
<220> FEATURE:
<223> OTHER INFORMATION: Dest-c

<400> SEQUENCE: 45
gaagacatca tacagagacc aaggtctcag tggttacata tgtcttc                        47

<210> SEQ ID NO 46
<211> LENGTH: 47
<212> TYPE: DNA
<213> ORGANISM: Artificial sequence
<220> FEATURE:
<223> OTHER INFORMATION: Dest-d

<400> SEQUENCE: 46
gaagacatac atacagagac caaggtctca gtggttacaa tgtcttc                        47

<210> SEQ ID NO 47
<211> LENGTH: 47
<212> TYPE: DNA
<213> ORGANISM: Artificial sequence
<220> FEATURE:
<223> OTHER INFORMATION: Dest-e

<400> SEQUENCE: 47
gaagacatta catacagaga ccaaggtctc agtggtgaca tgtcttc                        47

<210> SEQ ID NO 48
<211> LENGTH: 47
<212> TYPE: DNA
```

-continued

<213> ORGANISM: Artificial sequence
<220> FEATURE:
<223> OTHER INFORMATION: Dest-f

<400> SEQUENCE: 48
gaagacattg acatacagag accaaggtct cagtggttaa tgtcttc                          47

<210> SEQ ID NO 49
<211> LENGTH: 47
<212> TYPE: DNA
<213> ORGANISM: Artificial sequence
<220> FEATURE:
<223> OTHER INFORMATION: Dest-g

<400> SEQUENCE: 49
gaagacatgt tacatacaga gaccaaggtc tcagtggtca tgtcttc                          47

<210> SEQ ID NO 50
<211> LENGTH: 47
<212> TYPE: DNA
<213> ORGANISM: Artificial sequence
<220> FEATURE:
<223> OTHER INFORMATION: Dest-h

<400> SEQUENCE: 50
gaagacatgg tcacatacag agaccaaggt ctcagtggta tgtcttc                          47

<210> SEQ ID NO 51
<211> LENGTH: 47
<212> TYPE: DNA
<213> ORGANISM: Artificial sequence
<220> FEATURE:
<223> OTHER INFORMATION: Dest-i

<400> SEQUENCE: 51
gaagacattg gttacataca gagaccaagg tctcagtgga tgtcttc                          47

<210> SEQ ID NO 52
<211> LENGTH: 45
<212> TYPE: DNA
<213> ORGANISM: Artificial sequence
<220> FEATURE:
<223> OTHER INFORMATION: Dest-j

<400> SEQUENCE: 52
gaagacatgt ggtgacatac agagaccaag gtctcagtgg tcttc                            45

<210> SEQ ID NO 53
<211> LENGTH: 5
<212> TYPE: PRT
<213> ORGANISM: Artificial sequence
<220> FEATURE:
<223> OTHER INFORMATION: signal sequence

<400> SEQUENCE: 53

Met Gly Asn Ser Val
1               5

<210> SEQ ID NO 54
<211> LENGTH: 22
<212> TYPE: PRT
<213> ORGANISM: Artificial sequence
<220> FEATURE:
<223> OTHER INFORMATION: signal sequence

<400> SEQUENCE: 54

```
Glu Leu Thr Tyr Asn Thr Leu Ile Ser Gly Leu Gly Lys Ala Gly Arg
1               5                   10                  15

Ala Arg Asp Pro Pro Val
            20

<210> SEQ ID NO 55
<211> LENGTH: 4
<212> TYPE: PRT
<213> ORGANISM: Artificial sequence
<220> FEATURE:
<223> OTHER INFORMATION: signal sequence

<400> SEQUENCE: 55

Lys Asp Glu Leu
1

<210> SEQ ID NO 56
<211> LENGTH: 4
<212> TYPE: PRT
<213> ORGANISM: Artificial sequence
<220> FEATURE:
<223> OTHER INFORMATION: signal sequence

<400> SEQUENCE: 56

Lys Glu Glu Leu
1

<210> SEQ ID NO 57
<211> LENGTH: 19
<212> TYPE: PRT
<213> ORGANISM: Artificial sequence
<220> FEATURE:
<223> OTHER INFORMATION: signal sequence

<400> SEQUENCE: 57

Met Gly Trp Ser Cys Ile Ile Leu Phe Leu Val Ala Thr Ala Thr Gly
1               5                   10                  15

Ala His Ser

<210> SEQ ID NO 58
<211> LENGTH: 35
<212> TYPE: PRT
<213> ORGANISM: Artificial Sequence
<220> FEATURE:
<223> OTHER INFORMATION: 1st_A (v3.2_A)

<400> SEQUENCE: 58

Val Thr Tyr Thr Thr Asn Ile Asp Gln Leu Cys Lys Ala Gly Lys Val
1               5                   10                  15

Asp Glu Ala Leu Glu Leu Phe Lys Glu Met Arg Ser Lys Gly Val Lys
            20                  25                  30

Pro Asn Val
        35

<210> SEQ ID NO 59
<211> LENGTH: 35
<212> TYPE: PRT
<213> ORGANISM: Artificial Sequence
<220> FEATURE:
<223> OTHER INFORMATION: 1st_G (v3.2_G)

<400> SEQUENCE: 59

Val Thr Tyr Thr Thr Asn Ile Asp Gln Leu Cys Lys Ala Gly Lys Val
1               5                   10                  15
```

Asp Glu Ala Leu Glu Leu Phe Asp Glu Met Lys Glu Arg Gly Ile Lys
            20                  25                  30

Pro Asp Val
        35

<210> SEQ ID NO 60
<211> LENGTH: 35
<212> TYPE: PRT
<213> ORGANISM: Artificial Sequence
<220> FEATURE:
<223> OTHER INFORMATION: 1st_U (v3.2_U)

<400> SEQUENCE: 60

Val Thr Tyr Asn Thr Asn Ile Asp Gln Leu Cys Lys Ala Gly Arg Leu
1               5                   10                  15

Asp Glu Ala Glu Glu Leu Leu Glu Glu Met Glu Glu Lys Gly Ile Lys
            20                  25                  30

Pro Asp Val
        35

<210> SEQ ID NO 61
<211> LENGTH: 2271
<212> TYPE: DNA
<213> ORGANISM: Artificial Sequence
<220> FEATURE:
<223> OTHER INFORMATION: v2_polypucleotide

<400> SEQUENCE: 61
atgggtcatc accatcatca tcacgggtcc ctgcaggact cagaagtcaa tcaagaagct      60
aagccagagg tcaagccaga agtcaagcct gagactcaca tcaatttaaa ggtgtccgat     120
ggatcttcag agatcttctt caagatcaaa aagaccactc ctttaagaag gctgatggaa     180
gcgttcgcta aaagacaggg taaggaaatg gactccttaa gattcttgta cgacggtatt     240
agaattcaag ctgatcaggc ccctgaagat ttggacatgg aggataacga tattattgag     300
gctcaccgcg aacagattgg aggtatggga aactccgtgg tcacatacaa caccctgatc     360
gacggcctgt gcaagagcgg caagatcgag gaggccctga gctgttcaa ggagatggag      420 gagaagggca tcaccccag cgtggtcaca tacaccacac tgatcgacgg actgtgtaaa      480
gccggcgacg tggacgaagc cctcgagctg ttcaaagaga tgcggagcaa gggcgtgaag     540
cccaacgtgg tgacatacac caccctgatc gacggcctgt gcaaggccgg caaagtggac     600
gaggccctgg agctgttcga cgagatgaag gagagggca tcaagcccga cgtggtcaca      660
tacaacaccc tgatcgacgg cctgtgcaag agcggcaaga tcgaggaggc cctgaagctg     720
ttcaaggaga tggaggagaa gggcatcacc cccagcgtgg ttacatacac cacactgatc     780
gacggactgt gtaaagccgg cgacgtggac gaagccctcg agctgttcaa agagatgcgg     840
agcaagggcg tgaagcccaa cgtggtcaca tacaccaccc tgatcgacgg cctgtgcaag     900
gccggcaagg tggatgaggc cctggagctg ttcgacgaga tgaaggagag gggcatcaag     960
cccgacgtgg ttacatacaa caccctgatc gacggcctgt gcaagagcgg caagatcgag    1020
gaggccctga gctgttcaa ggagatggag gagaagggca tcaccccag cgtggtcaca      1080 tacaccacac tgatcgacgg actgtgtaaa gccggcgacg tggacgaagc cctcgagctg    1140
ttcaaagaga tgcggagcaa gggcgtgaag cccaacgtgg tgacatacac caccctgatc    1200
gacggcctgt gcaaggccgg caaagtggac gaggccctgg agctgttcga cgagatgaag    1260
gagaggggca tcaagcccga cgtggtcaca tacaacaccc tgatcgacgg cctgtgcaag    1320

-continued

```
agcggcaaga tcgaggaggc cctgaagctg ttcaaggaga tggaggagaa gggcatcacc      1380
cccagcgtgg ttacatacac cacactgatc gacggactgt gtaaagccgg cgacgtggac      1440
gaagccctcg agctgttcaa agagatgcgg agcaagggcg tgaagcccaa cgtggtcaca      1500
tacaccaccc tgatcgacgg cctgtgcaag gccggcaagg tggatgaggc cctggagctg      1560
ttcgacgaga tgaaggagag gggcatcaag cccgacgtgg tcacatacaa caccctgatc      1620
gacggcctgt gcaagagcgg caagatcgag gaggccctga agctgttcaa ggagatggag      1680
gagaagggca tcaccccccag cgtggtcaca tacaccacac tgatcgacgg actgtgtaaa      1740
gccggcgacg tggacgaagc cctcgagctg ttcaaagaga tgcggagcaa gggcgtgaag      1800
cccaacgtgg ttacatacac caccctgatc gacggcctgt gcaaggccgg caaagtggac      1860
gaggccctgg agctgttcga cgagatgaag gagagagggca tcaagcccga cgtggtcaca      1920
tacaacaccc tgatcgacgg cctgtgcaag agcggcaaga tcgaggaggc cctgaagctg      1980
ttcaaggaga tggaggagaa gggcatcacc cccagcgtgg tgacatacac cacactgatc      2040
gacggactgt gtaaagccgg cgacgtggac gaagccctcg agctgttcaa agagatgcgg      2100
agcaagggcg tgaagcccaa cgtggtcaca tacaccaccc tgatcgacgg cctgtgcaag      2160
gccggcaagg tggatgaggc cctggagctg ttcgacgaga tgaaggagag gggcatcaag      2220
cccgacgagc tgacctacaa caccctgatc agcggcctgg gcaaggccgg c              2271
```

<210> SEQ ID NO 62
<211> LENGTH: 757
<212> TYPE: PRT
<213> ORGANISM: Artificial Sequence
<220> FEATURE:
<223> OTHER INFORMATION: v2_protein

<400> SEQUENCE: 62

```
Met Gly His His His His His His Gly Ser Leu Gln Asp Ser Glu Val
1               5                   10                  15

Asn Gln Glu Ala Lys Pro Glu Val Lys Pro Glu Val Lys Pro Glu Thr
            20                  25                  30

His Ile Asn Leu Lys Val Ser Asp Gly Ser Ser Glu Ile Phe Phe Lys
        35                  40                  45

Ile Lys Lys Thr Thr Pro Leu Arg Arg Leu Met Glu Ala Phe Ala Lys
    50                  55                  60

Arg Gln Gly Lys Glu Met Asp Ser Leu Arg Phe Leu Tyr Asp Gly Ile
65                  70                  75                  80

Arg Ile Gln Ala Asp Gln Ala Pro Glu Asp Leu Asp Met Glu Asp Asn
                85                  90                  95

Asp Ile Ile Glu Ala His Arg Glu Gln Ile Gly Gly Met Gly Asn Ser
            100                 105                 110

Val Val Thr Tyr Asn Thr Leu Ile Asp Gly Leu Cys Lys Ser Gly Lys
        115                 120                 125

Ile Glu Glu Ala Leu Lys Leu Phe Lys Glu Met Glu Glu Lys Gly Ile
    130                 135                 140

Thr Pro Ser Val Val Thr Tyr Thr Thr Leu Ile Asp Gly Leu Cys Lys
145                 150                 155                 160

Ala Gly Asp Val Asp Glu Ala Leu Glu Leu Phe Lys Glu Met Arg Ser
                165                 170                 175

Lys Gly Val Lys Pro Asn Val Val Thr Tyr Thr Thr Leu Ile Asp Gly
            180                 185                 190

Leu Cys Lys Ala Gly Lys Val Asp Glu Ala Leu Glu Leu Phe Asp Glu
```

```
                    195                 200                 205
Met Lys Glu Arg Gly Ile Lys Pro Asp Val Val Thr Tyr Asn Thr Leu
    210                 215                 220
Ile Asp Gly Leu Cys Lys Ser Gly Lys Ile Glu Glu Ala Leu Lys Leu
225                 230                 235                 240
Phe Lys Glu Met Glu Glu Lys Gly Ile Thr Pro Ser Val Val Thr Tyr
                245                 250                 255
Thr Thr Leu Ile Asp Gly Leu Cys Lys Ala Gly Asp Val Asp Glu Ala
                260                 265                 270
Leu Glu Leu Phe Lys Glu Met Arg Ser Lys Gly Val Lys Pro Asn Val
            275                 280                 285
Val Thr Tyr Thr Thr Leu Ile Asp Gly Leu Cys Lys Ala Gly Lys Val
    290                 295                 300
Asp Glu Ala Leu Glu Leu Phe Asp Glu Met Lys Glu Arg Gly Ile Lys
305                 310                 315                 320
Pro Asp Val Val Thr Tyr Asn Thr Leu Ile Asp Gly Leu Cys Lys Ser
                325                 330                 335
Gly Lys Ile Glu Glu Ala Leu Lys Leu Phe Lys Glu Met Glu Glu Lys
            340                 345                 350
Gly Ile Thr Pro Ser Val Val Thr Tyr Thr Thr Leu Ile Asp Gly Leu
            355                 360                 365
Cys Lys Ala Gly Asp Val Asp Glu Ala Leu Glu Leu Phe Lys Glu Met
    370                 375                 380
Arg Ser Lys Gly Val Lys Pro Asn Val Val Thr Tyr Thr Thr Leu Ile
385                 390                 395                 400
Asp Gly Leu Cys Lys Ala Gly Lys Val Asp Glu Ala Leu Glu Leu Phe
                405                 410                 415
Asp Glu Met Lys Glu Arg Gly Ile Lys Pro Asp Val Val Thr Tyr Asn
            420                 425                 430
Thr Leu Ile Asp Gly Leu Cys Lys Ser Gly Lys Ile Glu Glu Ala Leu
            435                 440                 445
Lys Leu Phe Lys Glu Met Glu Glu Lys Gly Ile Thr Pro Ser Val Val
    450                 455                 460
Thr Tyr Thr Thr Leu Ile Asp Gly Leu Cys Lys Ala Gly Asp Val Asp
465                 470                 475                 480
Glu Ala Leu Glu Leu Phe Lys Glu Met Arg Ser Lys Gly Val Lys Pro
                485                 490                 495
Asn Val Val Thr Tyr Thr Thr Leu Ile Asp Gly Leu Cys Lys Ala Gly
                500                 505                 510
Lys Val Asp Glu Ala Leu Glu Leu Phe Asp Glu Met Lys Glu Arg Gly
            515                 520                 525
Ile Lys Pro Asp Val Val Thr Tyr Asn Thr Leu Ile Asp Gly Leu Cys
    530                 535                 540
Lys Ser Gly Lys Ile Glu Glu Ala Leu Lys Leu Phe Lys Glu Met Glu
545                 550                 555                 560
Glu Lys Gly Ile Thr Pro Ser Val Val Thr Tyr Thr Thr Leu Ile Asp
                565                 570                 575
Gly Leu Cys Lys Ala Gly Asp Val Asp Glu Ala Leu Glu Leu Phe Lys
            580                 585                 590
Glu Met Arg Ser Lys Gly Val Lys Pro Asn Val Val Thr Tyr Thr Thr
            595                 600                 605
Leu Ile Asp Gly Leu Cys Lys Ala Gly Lys Val Asp Glu Ala Leu Glu
    610                 615                 620
```

```
Leu Phe Asp Glu Met Lys Glu Arg Gly Ile Lys Pro Asp Val Val Thr
625                 630                 635                 640

Tyr Asn Thr Leu Ile Asp Gly Leu Cys Lys Ser Gly Lys Ile Glu Glu
                645                 650                 655

Ala Leu Lys Leu Phe Lys Glu Met Glu Glu Lys Gly Ile Thr Pro Ser
            660                 665                 670

Val Val Thr Tyr Thr Thr Leu Ile Asp Gly Leu Cys Lys Ala Gly Asp
        675                 680                 685

Val Asp Glu Ala Leu Glu Leu Phe Lys Glu Met Arg Ser Lys Gly Val
    690                 695                 700

Lys Pro Asn Val Val Thr Tyr Thr Thr Leu Ile Asp Gly Leu Cys Lys
705                 710                 715                 720

Ala Gly Lys Val Asp Glu Ala Leu Glu Leu Phe Asp Glu Met Lys Glu
                725                 730                 735

Arg Gly Ile Lys Pro Asp Glu Leu Thr Tyr Asn Thr Leu Ile Ser Gly
            740                 745                 750

Leu Gly Lys Ala Gly
        755
```

<210> SEQ ID NO 63
<211> LENGTH: 2274
<212> TYPE: DNA
<213> ORGANISM: Artificial Sequence
<220> FEATURE:
<223> OTHER INFORMATION: v3.2_polypucleotide

<400> SEQUENCE: 63

```
atgggtcatc accatcatca tcacgggtcc ctgcaggact cagaagtcaa tcaagaagct        60
aagccagagg tcaagccaga agtcaagcct gagactcaca tcaatttaaa ggtgtccgat       120
ggatcttcag agatcttctt caagatcaaa aagaccactc ctttaagaag gctgatggaa       180
gcgttcgcta aaagacaggg taaggaaatg gactccttaa gattcttgta cgacggtatt       240
agaattcaag ctgatcaggc ccctgaagat ttggacatgg aggataacga tattattgag       300 gctaccgcg aacagattgg aggtatggga aactccgtgg tcacatacaa caccaacatc        360
gaccagctgt gcaagagcgg caagatcgag gaggccctga gctgttcaa ggagatggag        420 gagaagggca tcaccccag cgtggtcaca tacaccacac tgatcgacgg actgtgtaaa        480
gccggcgacg tggacgaagc cctcgagctg ttcaaagaga tgcggagcaa gggcgtgaag       540
cccaacgtgg tgcatacac caccctgatc gacggcctgt gcaaggccgg caaagtggac       600
gaggccctgg agctgttcga cgagatgaag gagaggggca tcaagcccga cgtggtcaca       660
tacaacaccc tgatcgacgg cctgtgcaag agcggcaaga tcgaggaggc cctgaagctg       720
ttcaaggaga tggaggagaa gggcatcacc cccagcgtgg ttacatacac cacactgatc       780
gacggactgt gtaaagccgg cgacgtggac gaagccctcg agctgttcaa agagatgcgg       840
agcaagggcg tgaagcccaa cgtggtcaca tacaccaccc tgatcgacgg cctgtgcaag       900
gccggcaagg tggatgaggc cctggagctg ttcgacgaga tgaaggagag gggcatcaag       960
cccgacgtgg ttacatacaa caccctgatc gacggcctgt gcaagagcgg caagatcgag      1020
gaggccctga gctgttcaa ggagatggag gagaagggca tcaccccag cgtggtcaca       1080 tacaccacac tgatcgacgg actgtgtaaa gccggcgacg tggacgaagc cctcgagctg      1140
ttcaaagaga tgcggagcaa gggcgtgaag cccaacgtgg tgcatacac caccctgatc       1200 gacggcctgt gcaaggccgg caaagtggac gaggccctgg agctgttcga cgagatgaag      1260
```

-continued

```
gagaggggca tcaagcccga cgtggtcaca tacaacaccc tgatcgacgg cctgtgcaag      1320
agcggcaaga tcgaggaggc cctgaagctg ttcaaggaga tggaggagaa gggcatcacc      1380
cccagcgtgg ttacatacac cacactgatc gacggactgt gtaaagccgg cgacgtggac      1440
gaagccctcg agctgttcaa agagatgcgg agcaagggcg tgaagcccaa cgtggtcaca      1500
tacaccaccc tgatcgacgg cctgtgcaag gccggcaagg tggatgaggc cctggagctg      1560
ttcgacgaga tgaaggagag gggcatcaag cccgacgtgg tcacatacaa caccctgatc      1620
gacggcctgt gcaagagcgg caagatcgag gaggccctga agctgttcaa ggagatggag      1680
gagaagggca tcaccccag cgtggtcaca tacaccacac tgatcgacgg actgtgtaaa      1740
gccggcgacg tggacgaagc cctcgagctg ttcaaagaga tgcggagcaa gggcgtgaag      1800
cccaacgtgg ttacatacac caccctgatc gacggcctgt gcaaggccgg caaagtggac      1860
gaggccctgg agctgttcga cgagatgaag gagaggggca tcaagcccga cgtggtcaca      1920
tacaacaccc tgatcgacgg cctgtgcaag agcggcaaga tcgaggaggc cctgaagctg      1980
ttcaaggaga tggaggagaa gggcatcacc cccagcgtgg tgacatacac cacactgatc      2040
gacggactgt gtaaagccgg cgacgtggac gaagccctcg agctgttcaa agagatgcgg      2100
agcaagggcg tgaagcccaa cgtggtcaca tacaccaccc tgatcgacgg cctgtgcaag      2160
gccggcaagg tggatgaggc cctggagctg ttcgacgaga tgaaggagag gggcatcaag      2220
cccgacgagg agctgaccta caacaccctg atcagcggcc tgggcaaggc cggc            2274
```

```
<210> SEQ ID NO 64
<211> LENGTH: 757
<212> TYPE: PRT
<213> ORGANISM: Artificial Sequence
<220> FEATURE:
<223> OTHER INFORMATION: v3.2_protein

<400> SEQUENCE: 64

Met Gly His His His His His His Gly Ser Leu Gln Asp Ser Glu Val
1               5                   10                  15

Asn Gln Glu Ala Lys Pro Glu Val Lys Pro Glu Val Lys Pro Glu Thr
            20                  25                  30

His Ile Asn Leu Lys Val Ser Asp Gly Ser Ser Glu Ile Phe Phe Lys
        35                  40                  45

Ile Lys Lys Thr Thr Pro Leu Arg Arg Leu Met Glu Ala Phe Ala Lys
    50                  55                  60

Arg Gln Gly Lys Glu Met Asp Ser Leu Arg Phe Leu Tyr Asp Gly Ile
65                  70                  75                  80

Arg Ile Gln Ala Asp Gln Ala Pro Glu Asp Leu Asp Met Glu Asp Asn
                85                  90                  95

Asp Ile Ile Glu Ala His Arg Glu Gln Ile Gly Gly Met Gly Asn Ser
            100                 105                 110

Val Val Thr Tyr Asn Thr Asn Ile Asp Gln Leu Cys Lys Ser Gly Lys
        115                 120                 125

Ile Glu Glu Ala Leu Lys Leu Phe Lys Glu Met Glu Glu Lys Gly Ile
    130                 135                 140

Thr Pro Ser Val Val Thr Tyr Thr Thr Leu Ile Asp Gly Leu Cys Lys
145                 150                 155                 160

Ala Gly Asp Val Asp Glu Ala Leu Glu Leu Phe Lys Glu Met Arg Ser
                165                 170                 175

Lys Gly Val Lys Pro Asn Val Val Thr Tyr Thr Thr Leu Ile Asp Gly
```

-continued

```
                180                 185                 190

Leu Cys Lys Ala Gly Lys Val Asp Glu Ala Leu Glu Leu Phe Asp Glu
        195                 200                 205

Met Lys Glu Arg Gly Ile Lys Pro Asp Val Val Thr Tyr Asn Thr Leu
        210                 215                 220

Ile Asp Gly Leu Cys Lys Ser Gly Lys Ile Glu Glu Ala Leu Lys Leu
225                 230                 235                 240

Phe Lys Glu Met Glu Glu Lys Gly Ile Thr Pro Ser Val Val Thr Tyr
                245                 250                 255

Thr Thr Leu Ile Asp Gly Leu Cys Lys Ala Gly Asp Val Asp Glu Ala
                260                 265                 270

Leu Glu Leu Phe Lys Glu Met Arg Ser Lys Gly Val Lys Pro Asn Val
        275                 280                 285

Val Thr Tyr Thr Thr Leu Ile Asp Gly Leu Cys Lys Ala Gly Lys Val
        290                 295                 300

Asp Glu Ala Leu Glu Leu Phe Asp Glu Met Lys Glu Arg Gly Ile Lys
305                 310                 315                 320

Pro Asp Val Val Thr Tyr Asn Thr Leu Ile Asp Gly Leu Cys Lys Ser
                325                 330                 335

Gly Lys Ile Glu Glu Ala Leu Lys Leu Phe Lys Glu Met Glu Glu Lys
        340                 345                 350

Gly Ile Thr Pro Ser Val Val Thr Tyr Thr Thr Leu Ile Asp Gly Leu
        355                 360                 365

Cys Lys Ala Gly Asp Val Asp Glu Ala Leu Glu Leu Phe Lys Glu Met
        370                 375                 380

Arg Ser Lys Gly Val Lys Pro Asn Val Val Thr Tyr Thr Thr Leu Ile
385                 390                 395                 400

Asp Gly Leu Cys Lys Ala Gly Lys Val Asp Glu Ala Leu Glu Leu Phe
                405                 410                 415

Asp Glu Met Lys Glu Arg Gly Ile Lys Pro Asp Val Val Thr Tyr Asn
                420                 425                 430

Thr Leu Ile Asp Gly Leu Cys Lys Ser Gly Lys Ile Glu Glu Ala Leu
        435                 440                 445

Lys Leu Phe Lys Glu Met Glu Glu Lys Gly Ile Thr Pro Ser Val Val
        450                 455                 460

Thr Tyr Thr Thr Leu Ile Asp Gly Leu Cys Lys Ala Gly Asp Val Asp
465                 470                 475                 480

Glu Ala Leu Glu Leu Phe Lys Glu Met Arg Ser Lys Gly Val Lys Pro
                485                 490                 495

Asn Val Val Thr Tyr Thr Thr Leu Ile Asp Gly Leu Cys Lys Ala Gly
                500                 505                 510

Lys Val Asp Glu Ala Leu Glu Leu Phe Asp Glu Met Lys Glu Arg Gly
        515                 520                 525

Ile Lys Pro Asp Val Val Thr Tyr Asn Thr Leu Ile Asp Gly Leu Cys
        530                 535                 540

Lys Ser Gly Lys Ile Glu Glu Ala Leu Lys Leu Phe Lys Glu Met Glu
545                 550                 555                 560

Glu Lys Gly Ile Thr Pro Ser Val Val Thr Tyr Thr Thr Leu Ile Asp
                565                 570                 575

Gly Leu Cys Lys Ala Gly Asp Val Asp Glu Ala Leu Glu Leu Phe Lys
                580                 585                 590

Glu Met Arg Ser Lys Gly Val Lys Pro Asn Val Val Thr Tyr Thr Thr
                595                 600                 605
```

-continued

```
Leu Ile Asp Gly Leu Cys Lys Ala Gly Lys Val Asp Glu Ala Leu Glu
    610             615             620

Leu Phe Asp Glu Met Lys Glu Arg Gly Ile Lys Pro Asp Val Val Thr
625             630             635             640

Tyr Asn Thr Leu Ile Asp Gly Leu Cys Lys Ser Gly Lys Ile Glu Glu
                645             650             655

Ala Leu Lys Leu Phe Lys Glu Met Glu Glu Lys Gly Ile Thr Pro Ser
            660             665             670

Val Val Thr Tyr Thr Thr Leu Ile Asp Gly Leu Cys Lys Ala Gly Asp
        675             680             685

Val Asp Glu Ala Leu Glu Leu Phe Lys Glu Met Arg Ser Lys Gly Val
    690             695             700

Lys Pro Asn Val Val Thr Tyr Thr Thr Leu Ile Asp Gly Leu Cys Lys
705             710             715             720

Ala Gly Lys Val Asp Glu Ala Leu Glu Leu Phe Asp Glu Met Lys Glu
            725             730             735

Arg Gly Ile Lys Pro Asp Glu Leu Thr Tyr Asn Thr Leu Ile Ser Gly
            740             745             750

Leu Gly Lys Ala Gly
```

PPR PROTEIN CAUSING LESS AGGREGATION AND USE OF THE SAME

TECHNICAL FIELD

The present invention relates to a nucleic acid manipulation technique using a protein capable of binding to an intended nucleic acid. The present invention is useful in a wide range of fields, including medicine (drug discovery support, therapeutic treatment etc.), agriculture (agricultural, fishery and livestock production, breeding etc.), and chemistry (biological material production etc.).

BACKGROUND TECHNIQUES

PPR proteins are proteins comprising repeat of PPR motifs each having about 35 amino acids length, and one PPR motif can specifically bind to one base. The combination of the first, fourth, and ii-th (second from the end before the next motif) amino acids in a PPR motif determines to which one of adenine, cytosine, guanine, and uracil (or thymine) the motif binds (Patent documents 1 and 2). Among the naturally occurring RNA-binding PPR motifs, the combinations corresponding to each of the bases most frequently occurring are: first valine, fourth threonine, and ii-th asparagine for adenine; first valine, fourth asparagine, and ii-th serine for cytosine; first valine, fourth threonine, and ii-th aspartic acid for guanine, and first valine, fourth asparagine, and ii-th aspartic acid for uracil (Non-patent documents 1 to 5). By using these combinations of amino acids, PPR proteins that can specifically bind to an arbitrary sequence can be designed.

PRIOR ART REFERENCES

Patent Documents

Patent document 1: International Publication WO2013/058404
Patent document 2: International Publication WO2014/175284
Patent document 3: Japanese Patent Application No. 2019-100551

Non-Patent Documents

Non-patent document 1: Coquille, S. et al., An artificial PPR scaffold for programmable RNA recognition, Nature Communications 5, Article number: 5729 (2014)
Non-patent document 2: Shen, C. et al., Specific RNA Recognition by Designer Pentatricopeptide Repeat Protein, Molecular Plant 8, 667-670 (2015)
Non-patent document 3: Shen, C. et al., Structural basis for specific single-stranded RNA recognition by designer pentatricopeptide repeat proteins, Nature Communications, Volume 7, Article number: 11285 (2016)
Non-patent document 4: Miranda, R. G. et al., RNA-binding specificity landscapes of designer pentatricopeptide repeat proteins elucidate principles of PPR-RNA interactions, Nucleic Acids Research, 46(5), 2613-2623 (2018)
Non-patent document 5: Yan, J. et al., Delineation of pentatricopeptide repeat codes for target RNA prediction, Nucleic Acids Research, gkz075 (2019)

SUMMARY OF THE INVENTION

Object to be Achieved by the Invention

The inventors of the present invention have examined preparation of PPR proteins having high performance and formed by linking many, for example, 15 or more, of PPR motifs using the amino acid combinations mentioned above (Patent Document 3). On the other hand, according to the examination of the inventors of the present invention, it was found that some of the PPR proteins prepared in such a manner show aggregation property. In particular, when the PPR proteins were expressed in cultured animal cells, aggregation may be observed.

Means for Achieving the Object

Therefore, the inventors of the present invention examined to solve this problem by amino acid mutation in the PPR motifs. Then, they found that the aggregation properties of PPR proteins can be improved by changing the 6th, preferably the 6th and 9th, amino acids of the first motif (on the N-terminal side) of the PPR protein to hydrophilic amino acids, and accomplished the present invention.

The present invention provides the followings.

[1] A PPR motif, which is any one of the following PPR motifs:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, and 34, and having a cytosine-binding property;

(C-3) a PPR motif having a sequence identity of at least 80% to any one of the sequences of SEQ ID NOS: 4 to 7, provided that the amino acids at positions 1, 4, 6, and 34 are identical, and having a cytosine-binding property;

(A-1) a PPR motif consisting of the sequence of SEQ ID NO: 8 having a substitution of the amino acid at position 6 with asparagine or aspartic acid;

(A-2) a PPR motif consisting of the sequence of (A-1) having a substitution, deletion, or addition of 1 to 9 amino acids other than the amino acids at positions 1, 4, 6, and 34, and having an adenine-binding property;

(A-3) a PPR motif having a sequence identity of at least 80% to the sequence of (A-1), provided that the amino acids at positions 1, 4, 6, and 34 are identical, and having an adenine-binding property;

(G-1) a PPR motif consisting of the sequence of SEQ ID NO: 9 having a substitution of the amino acid at position 6 with asparagine or aspartic acid;

(G-2) a PPR motif consisting of the sequence of (G-1) having a substitution, deletion, or addition of 1 to 9 amino acids other than the amino acids at positions 1, 4, 6, and 34, and having a guanine-binding property;

(G-3) a PPR motif having a sequence identity of at least 80% to the sequence of (G-1), provided that the amino acids at positions 1, 4, 6, and 34 are identical, and having a guanine-binding property;

(U-1) a PPR motif consisting of the sequence of SEQ ID NO: 10 having a substitution of the amino acid at position 6 with asparagine or aspartic acid;

(U-2) a PPR motif consisting of the sequence of (U-1) having a substitution, deletion, or addition of 1 to 9 amino acids other than the amino acids at positions 1, 4, 6, and 34, and having a uracil-binding property; and (U-3) a PPR motif having a sequence identity of at least 80% to the sequence of (U-1), provided that the amino acids at positions 1, 4, 6, and 34 are identical, and having a uracil-binding property.

[2] A PPR motif, which is any one of the following PPR motifs:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, 9, and 34, and having a cytosine-binding property;

(C-3) a PPR motif having a sequence identity of at least 80% to any one of the sequences of SEQ ID NOS: 4 to 7, provided that the amino acids at positions 1, 4, 6, 9, and 34 are identical, and having a cytosine-binding property;

(A-1) a PPR motif consisting of the sequence of SEQ ID NO: 8 having such substitutions of the amino acids at positions 6 and 9 that any one of the combinations defined below is satisfied;

(A-2) a PPR motif consisting of the sequence of (A-1) having a substitution, deletion, or addition of 1 to 9 amino acids other than the amino acids at positions 1, 4, 6, 9, and 34, and having an adenine-binding property;

(A-3) a PPR motif having a sequence identity of at least 80% to the sequence of (A-1), provided that the amino acids at positions 1, 4, 6, 9, and 34 are identical, and having an adenine-binding property;

(G-1) a PPR motif consisting of the sequence of SEQ ID NO: 9 having such substitutions of the amino acids at positions 6 and 9 that any one of the combinations defined below is satisfied;

(G-2) a PPR motif consisting of the sequence of (G-1) having a substitution, deletion, or addition of 1 to 9 amino acids other than the amino acids at positions 1, 4, 6, 9, and 34, and having a guanine-binding property;

(G-3) a PPR motif having a sequence identity of at least 80% to the sequence of (G-1), provided that the amino acids at positions 1, 4, 6, 9, and 34 are identical, and having a guanine-binding property;

(U-1) a PPR motif consisting of the sequence of SEQ ID NO: 10 having such substitutions of the amino acids at positions 6 and 9 that any one of the combinations defined below is satisfied;

(U-2) a PPR motif consisting of the sequence of (U-1) having a substitution, deletion, or addition of 1 to 9 amino acids other than the amino acids at positions 1, 4, 6, 9, and 34, and having a uracil-binding property; and (U-3) a PPR motif having a sequence identity of at least 80% to the sequence of (U-1), provided that the amino acids at positions 1, 4, 6, 9, and 34 are identical, and having a uracil-binding property.

a combination of asparagine as the amino acid at position 6 and glutamic acid as the amino acid at position 9, a combination of asparagine as the amino acid at position 6 and glutamine as the amino acid at position 9, a combination of asparagine as the amino acid at position 6 and lysine as the amino acid at position 9, and a combination of aspartic acid as the amino acid at position 6 and glycine as the amino acid at position 9.

[3] The PPR motif according to 1 or 2, which is any one of the following PPR motifs:

(C-4) a PPR motif consisting of the sequence of SEQ ID NO: 4;

(A-4) a PPR motif consisting of the sequence of SEQ ID NO: 58;

(G-4) a PPR motif consisting of the sequence of SEQ ID NO: 59; and (U-4) a PPR motif consisting of the sequence of SEQ ID NO: 60.

[4] Use of the PPR motif according to any one of 1 to 3 in a PPR protein as the first PPR motif from the N-terminus.

[5] The use according to 4, which is for reducing aggregation of the PPR protein.

[6] A protein capable of binding to a target nucleic acid having a specific nucleotide sequence, which comprises 1 to 30 of PPR motifs represented by the formula 1 mentioned below, and wherein the $A_6$ amino acid of the first PPR motif ($M_1$) from the N-terminus is a hydrophilic amino acid:

[Formula 1]

$$\text{(Helix A)-X-(Helix B)-L} \quad \text{(Formula 1)}$$

wherein, in the formula:

Helix A is a moiety of 12-amino acid length capable of forming an α-helix structure, and is represented by the formula 2;

[Formula 2]

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \quad \text{(Formula 2)}$$

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[Formula 3]

$$L_{vii}\text{-}L_{vi}\text{-}L_v\text{-}L_{iv}\text{-}L_{iii}\text{-}L_{ii}\text{-}L_i \quad \text{(Formula 3)}$$

wherein, in the formula 3, the amino acids are numbered "i" (−1), "ii" (−2), and so on from the C-terminus side, provided that $L_{iii}$ to $L_{vii}$ may not exist.

[7] The protein according to 6, wherein the $A_9$ amino acid of $M_1$ is a hydrophilic amino acid or glycine.

[8] The protein according to 6 or 7, wherein the $A_6$ amino acid of $M_1$ is asparagine or aspartic acid.

[9] The protein according to any one of 6 to 8, wherein the $A_9$ amino acid of $M_1$ is glutamine, glutamic acid, lysine, or glycine.

[10] The protein according to any one of 6 to 9, wherein the $A_6$ amino acid of $M_1$ and the $A_9$ amino acid of $M_1$ correspond to any of the following combinations:

combination of asparagine as the $A_6$ amino acid and glutamic acid as the $A_9$ amino acid, combination of asparagine as the $A_6$ amino acid and glutamine as the $A_9$ amino acid, combination of asparagine as the $A_6$ amino acid and lysine as the $A_9$ amino acid, and combination of aspartic acid as the $A_6$ amino acid and glycine as the $A_9$ amino acid.

[11] A fusion protein of at least one selected from the group consisting of a fluorescent protein, a nuclear localization signal peptide, and a tag protein, and a PPR protein containing the PPR motif according to any one of 1 to 3 as the first PPR motif from the N-terminus, or the protein according to any one of 6 to 10.

[12] A method for modifying a PPR protein containing the PPR motif according to 6 and capable of binding to a target nucleic acid having a specific nucleotide sequence, which comprises making the $A_6$ amino acid of the first PPR motif ($M_1$) from the N-terminus more hydrophilic.

[13] A method for detecting a nucleic acid, which uses a PPR protein containing the PPR motif according to any one of 1 to 3 as the first PPR motif from the N-terminus, the protein according to any one of 6 to 10, or the fusion protein according to 11.

[14] A nucleic acid encoding the PPR motif according to any one of 1 to 3, a PPR protein containing the PPR motif according to any one of 1 to 3 as the first PPR motif from the N-terminus, or the protein according to any one of 6 to 10.

[15] A vector comprising the nucleic acid according to 14.

[16] A cell (except for human individual) containing the vector according to 15.

[17] A method for manipulating a nucleic acid, which uses the PPR motif according to any one of 1 to 3, a PPR protein containing the PPR motif according to any one of 1 to 3 as the first PPR motif from the N-terminus, the protein according to any one of 6 to 10, or the vector according to 15 (implementation in human individual is excluded).

[18] A method for producing an organism, which comprises the manipulation method according to 17.

The present invention also provides the followings.

[1] A PPR motif, which is any one of the following PPR motifs:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, and 34, and having a cytosine-binding property;

(C-3) a PPR motif having a sequence identity of at least 80% to any one of the sequences of SEQ ID NOS: 4 to 7, provided that the amino acids at positions 1, 4, 6, and 34 are identical, and having a cytosine-binding property;

(A-1) a PPR motif consisting of the sequence of SEQ ID NO: 8 having a substitution of the amino acid at position 6 with asparagine or aspartic acid;

(A-2) a PPR motif consisting of the sequence of (A-1) having a substitution, deletion, or addition of 1 to 9 amino acids other than the amino acids at positions 1, 4, 6, and 34, and having an adenine-binding property;

(A-3) a PPR motif having a sequence identity of at least 80% to the sequence of (A-1), provided that the amino acids at positions 1, 4, 6, and 34 are identical, and having an adenine-binding property;

(G-1) a PPR motif consisting of the sequence of SEQ ID NO: 9 having a substitution of the amino acid at position 6 with asparagine or aspartic acid;

(G-2) a PPR motif consisting of the sequence of (G-1) having a substitution, deletion, or addition of 1 to 9 amino acids other than the amino acids at positions 1, 4, 6, and 34, and having a guanine-binding property;

(G-3) a PPR motif having a sequence identity of at least 80% to the sequence of (G-1), provided that the amino acids at positions 1, 4, 6, and 34 are identical, and having a guanine-binding property;

(U-1) a PPR motif consisting of the sequence of SEQ LD NO: 10 having a substitution of the amino acid at position 6 with asparagine or aspartic acid;

(U-2) a PPR motif consisting of the sequence of (U-1) having a substitution, deletion, or addition of 1 to 9 amino acids other than the amino acids at positions 1, 4, 6, and 34, and having a uracil-binding property; and (U-3) a PPR motif having a sequence identity of at least 80% to the sequence of (U-1), provided that the amino acids at positions 1, 4, 6, and 34 are identical, and having a uracil-binding property.

[2] A PPR motif, which is any one of the following PPR motifs:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, 9, and 34, and having a cytosine-binding property;

(C-3) a PPR motif having a sequence identity of at least 80% to any one of the sequences of SEQ ID NOS: 4 to 7, provided that the amino acids at positions 1, 4, 6, 9, and 34 are identical, and having a cytosine-binding property;

(A-1) a PPR motif consisting of the sequence of SEQ ID NO: 8 having such substitutions of the amino acids at positions 6 and 9 that any one of the combinations defined below is satisfied;

(A-2) a PPR motif consisting of the sequence of (A-1) having a substitution, deletion, or addition of 1 to 9 amino acids other than the amino acids at positions 1, 4, 6, 9, and 34, and having an adenine-binding property;

(A-3) a PPR motif having a sequence identity of at least 80% to the sequence of (A-1), provided that the amino acids at positions 1, 4, 6, 9, and 34 are identical, and having an adenine-binding property;

(G-1) a PPR motif consisting of the sequence of SEQ ID NO: 9 having such substitutions of the amino acids at positions 6 and 9 that any one of the combinations defined below is satisfied;

(G-2) a PPR motif consisting of the sequence of (G-1) having a substitution, deletion, or addition of 1 to 9 amino acids other than the amino acids at positions 1, 4, 6, 9, and 34, and having a guanine-binding property;

(G-3) a PPR motif having a sequence identity of at least 80% to the sequence of (G-1), provided that the amino acids at positions 1, 4, 6, 9, and 34 are identical, and having a guanine-binding property;

(U-1) a PPR motif consisting of the sequence of SEQ ID NO: 10 having such substitutions of the amino acids at positions 6 and 9 that any one of the combinations defined below is satisfied;

(U-2) a PPR motif consisting of the sequence of (U-1) having a substitution, deletion, or addition of 1 to 9 amino acids other than the amino acids at positions 1, 4, 6, 9, and 34, and having a uracil-binding property; and (U-3) a PPR motif having a sequence identity of at least 80% to the sequence of (U-1), provided that the amino acids at positions 1, 4, 6, 9, and 34 are identical, and having a uracil-binding property.

a combination of asparagine as the amino acid at position 6 and glutamic acid as the amino acid at position 9, a combination of asparagine as the amino acid at position 6 and glutamine as the amino acid at position 9, a combination of asparagine as the amino acid at position 6 and lysine as the amino acid at position 9, and a combination of aspartic acid as the amino acid at position 6 and glycine as the amino acid at position 9.

[3] Use of the PPR motif according to 1 or 2 in a PPR protein as the first PPR motif from the N-terminus.

[4] The use according to 3, which is for reducing aggregation of the PPR protein.

[5] A protein capable of binding to a target nucleic acid having a specific nucleotide sequence, which comprises 1 to 30 of PPR motifs represented by the formula 1 mentioned below, and wherein the $A_6$ amino acid of the first PPR motif ($M_1$) from the N-terminus is a hydrophilic amino acid:

[Formula 4]

(Helix A)-X-(Helix B)-L                    (Formula 1)

wherein, in the formula:

Helix A is a moiety of 12-amino acid length capable of forming an α-helix structure, and is represented by the formula 2;

[Formula 5]

$A_1$-$A_2$-$A_3$-$A_4$-$A_5$-$A_6$-$A_7$-$A_8$-$A_9$-$A_{10}$-$A_{11}$-$A_{12}$          (Formula 2)

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[Formula 6]

$L_{vii}$-$L_{vi}$-$L_v$-$L_{iv}$-$L_{iii}$-$L_{ii}$-$L_i$              (Formula 3)

wherein, in the formula 3, the amino acids are numbered "i" (−1), "ii" (−2), and so on from the C-terminus side, provided that $L_{iii}$ to $L_{vii}$ may not exist.

[6] The protein according to 5, wherein the $A_9$ amino acid of $M_1$ is a hydrophilic amino acid or glycine.

[7] The protein according to 5 or 6, wherein the $A_6$ amino acid of $M_1$ is asparagine or aspartic acid.

[8] The protein according to any one of 5 to 7, wherein the $A_9$ amino acid of $M_1$ is glutamine, glutamic acid, lysine, or glycine.

[9] The protein according to any one of 5 to 8, wherein the $A_6$ amino acid of $M_1$ and the $A_9$ amino acid of $M_1$ correspond to any of the following combinations:

combination of asparagine as the $A_6$ amino acid and glutamic acid as the $A_9$ amino acid, combination of asparagine as the $A_6$ amino acid and glutamine as the $A_9$ amino acid, combination of asparagine as the $A_6$ amino acid and lysine as the $A_9$ amino acid, and combination of aspartic acid as the $A_6$ amino acid and glycine as the $A_9$ amino acid.

[10] A fusion protein of at least one selected from the group consisting of a fluorescent protein, a nuclear localization signal peptide, and a tag protein, and a PPR protein containing the PPR motif according to 1 or 2 as the first PPR motif from the N-terminus, or the protein according to any one of 5 to 9.

[11] A method for modifying a PPR protein containing the PPR motif according to 3 and capable of binding to a target nucleic acid having a specific nucleotide sequence, which comprises making the $A_6$ amino acid of the first PPR motif ($M_1$) from the N-terminus more hydrophilic.

[12] A method for detecting a nucleic acid, which uses a PPR protein containing the PPR motif according to 1 or 2 as the first PPR motif from the N-terminus, the protein according to any one of 5 to 9, or the fusion protein according to 10.

[13] A nucleic acid encoding the PPR motif according to 1 or 2, a PPR protein containing the PPR motif according to 1 or 2 as the first PPR motif from the N-terminus, or the protein according to any one of 5 to 9.

[14] A vector comprising the nucleic acid according to 13.

[15] A cell (except for human individual) containing the vector according to 14.

[16] A method for manipulating a nucleic acid, which uses the PPR motif according to 1 or 2, a PPR protein containing the PPR motif according to 1 or 2 as the first PPR motif from the N-terminus, the protein according to any one of 5 to 9, or the vector according to 14 (implementation in human individual is excluded).

[17] A method for producing an organism, which comprises the manipulation method according to 16.

BRIEF DESCRIPTION OF THE DRAWINGS

FIGS. 1A and 1B The method for designing a PPR motif. FIG. 1A: The 6th and 9th amino acids of the first motif are exposed to the outside. FIG. 1B: For the 6th and 9th amino acids of the first motif that recognize cytosine, there were chosen leucine and glycine (C_6L9G) as a typical combination, and leucine and glutamic acid (C_6L9E), asparagine and glutamine (C_6N9Q), asparagine and glutamic acid (C_6N9E), asparagine and lysine (C_6N9K), and aspartic acid and glycine (C_6D9G) as mutant types.

FIG. 2 Aggregation and localization into nuclei of each PPR protein. Intracellular expression of PPR fused with GFP and a nuclear localization signal sequence was confirmed on the basis of fluorescence microscopy images. When the protein was fused with EGFP, it was observed that PPRcag_1 (6L9G) and PPRcag_2 (6L9E) did not localize to the nuclei, but strongly aggregated around the nuclei. On the other hand, PPRcag_3 (6N9Q), PPRcag_4 (6N9E), PPRcag_5 (6N9K), and PPRcag_6 (6D9G) did not localize to the nuclei, although their aggregation was weak. When mClover3 was fused, it was observed that PPRcag_1 (6N9G) and PPRcag_2 (6L9E) localized to the nuclei, but they aggregated in the nuclei. PPRcag_3 (6N9Q), PPRcag_4 (6N9E), PPRcag_5 (6N9K), and PPRcag_6 (6D9G) localized to the nuclei, and showed no aggregation.

FIG. 3 Binding experiment of PPR protein and RNA. It was found that all PPR proteins including amino acid mutations of the 6th and 9th amino acids specifically bind to the target CAGx6. In comparison with PPRcag_1, the binding power to the target sequence was substantially the same for PPRcag_2, about 80% for PPRcag_3, about 60% for PPRcag_4, about 120% for PPRcag_5, and about 130% for PPRcag_6.

FIG. 4 The effect of the first PPR motif from the N-terminus on aggregation. Each PPR protein was prepared in an E. coli expression system, purified, and separated by gel filtration chromatography. The smaller volume of the elution fraction (Elution vol.) means a larger molecular size. The proteins using v2 were eluted in 8 to 10 mL of elution fractions, whereas the peaks of the proteins using v3.2 were observed in elution fractions of 12 to 14 mL. These results suggested possibility that the proteins using v2 aggregated due to the larger protein size thereof, and it was found that the aggregation was improved in the proteins using v3.2.

MODES FOR CARRYING OUT THE INVENTION

[PPR Motif and PPR Protein]

Definition

The PPR motif referred to in the present invention means a polypeptide constituted by 30 to 38 amino acids and having an amino acid sequence of an E value not larger than a predetermined value (desirably E-03) obtained for PF01535 in Pfam or PS51375 in Prosite as determined by amino acid sequence analysis with a protein domain search program on the Web, unless especially stated. The position numbers of amino acids constituting the PPR motif defined in the present invention are substantially synonymous with those of PF01535, and they correspond to those obtained by subtracting 2 from the numbers of the amino acid positions of PS51375 (for example, the position 1 referred to in the present invention corresponds to the position 3 of PS51375). Further, the term "ii" (−2)-th amino acid means the second amino acid from the end (C-terminus side) of the amino acids constituting the PPR motif, or the second amino acid towards the N-terminus side from the first amino acid of the following PPR motif, i.e., −2nd amino acid. When the following PPR motif is not definitely identified, the amino acid 2 amino acids before the first amino acid of the following helical structure is the amino acid of "ii". For Pfam, http://pfam.sanger.ac.uk/can be referred to, and for Prosite, http://www.expasy.org/prosite/can be referred to.

Although the conservativeness of the conserved amino acid sequence of the PPR motif is low at the amino acid level, two of the α-helixes as the secondary structure are well conserved. Although a typical PPR motif is constituted by 35 amino acids, the length thereof is as variable as is from 30 to 38 amino acids.

More specifically, the PPR motif referred to in the present invention consists of a polypeptide of a 30- to 38-amino acid length represented by the formula 1.

[Formula 7]

$$(\text{Helix A})\text{-X-}(\text{Helix B})\text{-L} \qquad \text{(Formula 1)}$$

wherein, in the formula:

Helix A is a moiety of 12-amino acid length capable of forming an α-helix structure, and is represented by the formula 2;

[Formula 8]

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \qquad \text{(Formula 2)}$$

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[Formula 9]

$$L_{vii}\text{-}L_{vi}\text{-}L_v\text{-}L_{iv}\text{-}L_{iii}\text{-}L_{ii}\text{-}L_i \qquad \text{(Formula 3)}$$

wherein, in the formula 3, the amino acids are numbered "i" (−1), "ii" (−2), and so on from the C-terminus side, provided that $L_{iii}$ to $L_{vii}$ may not exist.

The term PPR protein used in the present invention refers to a PPR protein comprising one or more, preferably two or more, of the above-mentioned PPR motifs, unless especially indicated. The term protein used in this description refers to any substance consisting of a polypeptide (chain consisting of a plurality of amino acids bound via peptide bonds), unless especially indicated, and includes those consisting of a polypeptide of a comparatively low molecular weight. The term amino acid used in the present invention refers to a usual amino acid molecule, and also refers to an amino acid residue constituting a peptide chain. Which one is referred to shall be clear to those skilled in the art from the context.

In the present invention, the term specificity/specific used for the binding property of the PPR motif to a base in the target nucleic acid means that the binding activity to any one of the four bases is higher than the binding activities to the other bases, unless especially stated.

In the present invention, the term nucleic acid refers to RNA or DNA. Although the PPR protein may have specificity for bases in RNA or DNA, it does not bind to nucleic acid monomers.

In the PPR motif, combination of three of the 1st, 4th, and ii-th amino acids is important for specific binding to a base, and to which base the motif binds can be determined according to this combination (Patent document 1 and 2 mentioned above).

Specifically, with respect to the RNA-binding PPR motifs, the relationship between the combinations of three of the 1st, 4th, and ii-th amino acids and the bases to which they can bind is as follows (see Patent document 1 mentioned above).

(3-1) When the combination of the three amino acids of $A_1$, $A_4$, and $L_{ii}$ consists of valine, asparagine, and aspartic acid in this order, the PPR motif has such a selective RNA base-binding ability that the motif strongly binds to U, less strongly to C, and still less strongly to A or G.

(3-2) When the combination of the three amino acids of $A_1$, $A_4$, and $L_{ii}$ consists of valine, threonine, and asparagine in this order, the PPR motif has such a selective RNA base-binding ability that the motif strongly binds to A, less strongly to G, and still less strongly to C, but dose not bind to U.

(3-3) When the combination of the three amino acids of $A_1$, $A_4$, and $L_{ii}$ consists of valine, asparagine, and asparagine in this order, the PPR motif has such a selective RNA base-binding ability that the motif strongly binds to C, and less strongly to A or U, but does not bind to G.

(3-4) When the combination of the three amino acids of $A_1$, $A_4$, and $L_{ii}$ consists of glutamic acid, glycine, and aspartic acid in this order, the PPR motif has such a selective RNA base-binding ability that the motif strongly binds to G, but does not bind to A, U, and C.

(3-5) When the combination of the three amino acids of $A_1$, $A_4$, and $L_{ii}$ consists of isoleucine, asparagine, and asparagine in this order, the PPR motif has such a selective RNA base-binding ability that the motif strongly binds to C, less strongly to U, and still less strongly to A, but does not bind to G.

(3-6) When the combination of the three amino acids of $A_1$, $A_4$, and $L_{ii}$ consists of valine, threonine, and aspartic acid in this order, the PPR motif has such a selective RNA base-binding ability that the motif strongly binds to G, and less strongly to U, but does not bind to A and C.

(3-7) When the combination of the three amino acids of $A_1$, $A_4$, and $L_{ii}$ consists of lysine, threonine, and aspartic acid in this order, the PPR motif has such a selective RNA base-binding ability that the motif strongly binds to G, and less strongly to A, but does not bind to U and C.

(3-8) When the combination of the three amino acids of $A_1$, $A_4$, and $L_{ii}$ consists of phenylalanine, serine, and asparagine in this order, the PPR motif has such a selective RNA base-binding ability that the motif strongly binds to A, less strongly to C, and still less strongly to G and U.

(3-9) When the combination of the three amino acids of $A_1$, $A_4$, and $L_{ii}$ consists of valine, asparagine, and serine in this order, the PPR motif has such a selective RNA base-binding ability that the motif strongly binds to C, and less strongly to U, but does not bind to A and G.

(3-10) When the combination of the three amino acids of $A_1$, $A_4$, and $L_{ii}$ consists of phenylalanine, threonine, and asparagine in this order, the PPR motif has such a selective RNA base-binding ability that the motif strongly binds to A, but does not bind to G, U, and C.

(3-11) When the combination of the three amino acids of $A_1$, $A_4$, and $L_{ii}$ consists of isoleucine, asparagine, and aspartic acid in this order, the PPR motif has such a selective RNA base-binding ability that the motif strongly binds to U, and less strongly to A, but does not bind to G and C.

(3-12) When the combination of the three amino acids of $A_1$, $A_4$, and $L_{ii}$ consists of threonine, threonine, and asparagine in this order, the PPR motif has such a selective RNA base-binding ability that the motif strongly binds to A, but does not bind to G, U, and C.

(3-13) When the combination of the three amino acids of $A_1$, $A_4$, and $L_{ii}$ consists of isoleucine, methionine, and aspartic acid in this order, the PPR motif has such a selective RNA base-binding ability that the motif strongly binds to U, and less strongly to C, but does not bind to A and G.

(3-14) When the combination of the three amino acids of $A_1$, $A_4$, and $L_{ii}$ consists of phenylalanine, proline, and aspartic acid in this order, the PPR motif has such a selective RNA base-binding ability that the motif strongly binds to U, and less strongly to C, but does not bind to A and G.

(3-15) When the combination of the three amino acids of $A_1$, $A_4$, and $L_{ii}$ consists of tyrosine, proline, and aspartic acid in this order, the PPR motif has such a selective RNA base-binding ability that the motif strongly binds to U, but does not bind to A, G, and C.

(3-16) When the combination of the three amino acids of $A_1$, $A_4$, and $L_{ii}$ consists of leucine, threonine, and aspartic acid in this order, the PPR motif has such a selective RNA base-binding ability that the motif strongly binds to G, but does not bind to A, U, and C.

Specifically, with respect to the DNA-binding PPR motifs, the relationship between combinations of the three of the 1st, 4th, and ii-th amino acids and the bases to which they can bind is as follows (see Patent document 2 mentioned above).

(2-1) When the combination of the three amino acids of $A_1$, $A_4$, and $L_{ii}$ consists of an arbitrary amino acid, glycine, and aspartic acid in this order, the PPR motif selectively binds to G.

(2-2) When the combination of the three amino acids of $A_1$, $A_4$, and $L_{ii}$ consists of glutamic acid, glycine, and aspartic acid in this order, the PPR motif selectively binds to G.

(2-3) When the combination of the three amino acids of $A_1$, $A_4$, and $L_{ii}$ consists of an arbitrary amino acid, glycine, and asparagine in this order, the PPR motif selectively binds to A.

(2-4) When the combination of the three amino acids of $A_1$, $A_4$, and $L_{ii}$ consists of glutamic acid, glycine, and asparagine in this order, the PPR motif selectively binds to A.

(2-5) When the combination of the three amino acids of $A_1$, $A_4$, and $L_{ii}$ consists of an arbitrary amino acid, glycine, and serine in this order, the PPR motif selectively binds to A, and less selectively to C.

(2-6) When the combination of the three amino acids of $A_1$, $A_4$, and $L_{ii}$ consists of an arbitrary amino acid, isoleucine, and an arbitrary amino acid in this order, the PPR motif selectively binds to T and C.

(2-7) When the combination of the three amino acids of $A_1$, $A_4$, and $L_{ii}$ consists of an arbitrary amino acid, isoleucine, and asparagine in this order, the PPR motif selectively binds to T, and less selectively to C.

(2-8) When the combination of the three amino acids of $A_1$, $A_4$, and $L_{ii}$ consists of an arbitrary amino acid, leucine, and an arbitrary amino acid in this order, the PPR motif selectively binds to T and C.

(2-9) When the combination of the three amino acids of $A_1$, $A_4$, and $L_{ii}$ consists of an arbitrary amino acid, leucine, and aspartic acid in this order, the PPR motif selectively binds to C.

(2-10) When the combination of the three amino acids of $A_1$, $A_4$, and $L_{ii}$ consists of an arbitrary amino acid, leucine, and lysine in this order, the PPR motif selectively binds to T.

(2-11) When the combination of the three amino acids of $A_1$, $A_4$, and $L_{ii}$ consists of an arbitrary amino acid, methionine, and an arbitrary amino acid in this order, the PPR motif selectively binds to T.

(2-12) When the combination of the three amino acids of $A_1$, $A_4$, and $L_{ii}$ consists of an arbitrary amino acid, methionine, and aspartic acid in this order, the PPR motif selectively binds to T.

(2-13) When the combination of the three amino acids of $A_1$, $A_4$, and $L_{ii}$ consists of isoleucine, methionine, and aspartic acid in this order, the PPR motif selectively binds to T, and less selectively to C.

(2-14) When the combination of the three amino acids of $A_1$, $A_4$, and $L_{ii}$ consists of an arbitrary amino acid, asparagine, and an arbitrary amino acid in this order, the PPR motif selectively binds to C and T.

(2-15) When the combination of the three amino acids of $A_1$, $A_4$, and $L_{ii}$ consists of an arbitrary amino acid, asparagine, and aspartic acid in this order, the PPR motif selectively binds to T.

(2-16) When the combination of the three amino acids of $A_1$, $A_4$, and $L_{ii}$ consists of phenylalanine, asparagine, and aspartic acid in this order, the PPR motif selectively binds to T.

(2-17) When the combination of the three amino acids of $A_1$, $A_4$, and $L_{ii}$ consists of glycine, asparagine, and aspartic acid in this order, the PPR motif selectively binds to T.

(2-18) When the combination of the three amino acids of $A_1$, $A_4$, and $L_{ii}$ consists of isoleucine, asparagine, and aspartic acid in this order, the PPR motif selectively binds to T.

(2-19) When the combination of the three amino acids of $A_1$, $A_4$, and $L_{ii}$ consists of threonine, asparagine, and aspartic acid in this order, the PPR motif selectively binds to T.

(2-20) When the combination of the three amino acids of $A_1$, $A_4$, and $L_{ii}$ consists of valine, asparagine, and aspartic acid in this order, the PPR motif selectively binds to T, and less selectively to C.

(2-21) When the combination of the three amino acids of $A_1$, $A_4$, and $L_{ii}$ consists of tyrosine, asparagine, and aspartic acid in this order, the PPR motif selectively binds to T, and less selectively to C.

(2-22) When the combination of the three amino acids of $A_1$, $A_4$, and $L_{ii}$ consists of an arbitrary amino acid, asparagine, and asparagine in this order, the PPR motif selectively binds to C.

(2-23) When the combination of the three amino acids of $A_1$, $A_4$, and $L_{ii}$ consists of isoleucine, asparagine, and asparagine in this order, the PPR motif selectively binds to C.

(2-24) When the combination of the three amino acids of $A_1$, $A_4$, and $L_{ii}$ consists of serine, asparagine, and asparagine in this order, the PPR motif selectively binds to C.

(2-25) When the combination of the three amino acids of $A_1$, $A_4$, and $L_{ii}$ consists of valine, asparagine, and asparagine in this order, the PPR motif selectively binds to C.

(2-26) When the combination of the three amino acids of $A_1$, $A_4$, and $L_{ii}$ consists of an arbitrary amino acid, asparagine, and serine in this order, the PPR motif selectively binds to C.

(2-27) When the combination of the three amino acids of $A_1$, $A_4$, and $L_{ii}$ consists of valine, asparagine, and serine in this order, the PPR motif selectively binds to C.

(2-28) When the combination of the three amino acids of $A_1$, $A_4$, and $L_{ii}$ consists of an arbitrary amino acid, asparagine, and threonine in this order, the PPR motif selectively binds to C.

(2-29) When the combination of the three amino acids of $A_1$, $A_4$, and $L_{ii}$ consists of valine, asparagine, and threonine in this order, the PPR motif selectively binds to C.

(2-30) When the combination of the three amino acids of $A_1$, $A_4$, and $L_{ii}$ consists of an arbitrary amino acid, asparagine, and tryptophan in this order, the PPR motif selectively binds to C, and less selectively to T.

(2-31) When the combination of the three amino acids of $A_1$, $A_4$, and $L_{ii}$ consists of isoleucine, asparagine, and tryptophan in this order, the PPR motif selectively binds to T, and less selectively to C.

(2-32) When the combination of the three amino acids of $A_1$, $A_4$, and $L_{ii}$ consists of an arbitrary amino acid, proline, and an arbitrary amino acid in this order, the PPR motif selectively binds to T.

(2-33) When the combination of the three amino acids of $A_1$, $A_4$, and $L_{ii}$ consists of an arbitrary amino acid, proline, and aspartic acid in this order, the PPR motif selectively binds to T.

(2-34) When the combination of the three amino acids of $A_1$, $A_4$, and $L_{ii}$ consists of phenylalanine, proline, and aspartic acid in this order, the PPR motif selectively binds to T.

(2-35) When the combination of the three amino acids of $A_1$, $A_4$, and $L_{ii}$ consists of tyrosine, proline, and aspartic acid in this order, the PPR motif selectively binds to T.

(2-36) When the combination of the three amino acids of $A_1$, $A_4$, and $L_{ii}$ consists of an arbitrary amino acid, serine, and an arbitrary amino acid in this order, the PPR motif selectively binds to A and G.

(2-37) When the combination of the three amino acids of $A_1$, $A_4$, and $L_{ii}$ consists of an arbitrary amino acid, serine, and asparagine in this order, the PPR motif selectively binds to A.

(2-38) When the combination of the three amino acids of $A_1$, $A_4$, and $L_{ii}$ consists of phenylalanine, serine, and asparagine in this order, the PPR motif selectively binds to A.

(2-39) When the combination of the three amino acids of $A_1$, $A_4$, and $L_{ii}$ consists of valine, serine, and asparagine in this order, the PPR motif selectively binds to A.

(2-40) When the combination of the three amino acids of $A_1$, $A_4$, and $L_{ii}$ consists of an arbitrary amino acid, threonine, and an arbitrary amino acid in this order, the PPR motif selectively binds to A and G.

(2-41) When the combination of the three amino acids of $A_1$, $A_4$, and $L_{ii}$ consists of an arbitrary amino acid, threonine, and aspartic acid in this order, the PPR motif selectively binds to G.

(2-42) When the combination of the three amino acids of $A_1$, $A_4$, and $L_{ii}$ consists of valine, threonine, and aspartic acid in this order, the PPR motif selectively binds to G.

(2-43) When the combination of the three amino acids of $A_1$, $A_4$, and $L_{ii}$ consists of an arbitrary amino acid, threonine, and asparagine in this order, the PPR motif selectively binds to A.

(2-44) When the combination of the three amino acids of $A_1$, $A_4$, and $L_{ii}$ consists of phenylalanine, threonine, and asparagine in this order, the PPR motif selectively binds to A.

(2-45) When the combination of the three amino acids of $A_1$, $A_4$, and $L_{ii}$ consists of isoleucine, threonine, and asparagine in this order, the PPR motif selectively binds to A.

(2-46) When the combination of the three amino acids of $A_1$, $A_4$, and $L_{ii}$ consists of valine, threonine, and asparagine in this order, the PPR motif selectively binds to A.

(2-47) When the combination of the three amino acids of $A_1$, $A_4$, and $L_{ii}$ consists of an arbitrary amino acid, valine, and an arbitrary amino acid in this order, the PPR motif binds to A, C, and T, but does not bind to G.

(2-48) When the combination of the three amino acids of $A_1$, $A_4$, and $L_{ii}$ consists of isoleucine, valine, and aspartic acid in this order, the PPR motif selectively binds to C, and less selectively to A.

(2-49) When the combination of the three amino acids of $A_1$, $A_4$, and $L_{ii}$ consists of an arbitrary amino acid, valine, and glycine in this order, the PPR motif selectively binds to C.

(2-50) When the combination of the three amino acids of $A_1$, $A_4$, and $L_{ii}$ consists of an arbitrary amino acid, valine, and threonine in this order, the PPR motif selectively binds to T.

(Particularly Preferred Combinations of the Three Amino Acids)

For the RNA-binding PPR motifs, there are typical combinations of the 1st, 4th, and ii-th amino acids that can recognize and specifically bind to each base. Specifically, the combination that recognizes adenine consists of 1 st valine, 4th threonine, and ii-th asparagine; the combination that recognizes cytosine consists of 1st valine, 4th asparagine, and ii-th serine; the combination that recognizes guanine consists of 1st valine, 4th threonine, and ii-th aspartic acid, and the combination that recognizes uracil consists of 1st is valine, 4th is asparagine, and ii-th aspartic acid (Non-patent documents 1 to 5 mentioned above). In one of the preferred embodiments of the present invention, these combinations are used.

(Improvement of Aggregation Property)

The inventors of the present invention found that the amino acid at position 6 of the PPR motif is extremely frequently hydrophobic amino acid (especially leucine) and the amino acid at position 9 is extremely frequently a non-hydrophilic amino acid (especially glycine) on the basis of the amino acid information of existing naturally occurring PPR motifs. On the basis of structures of the PPR proteins for which crystal structures have already been obtained (Non-patent document 6: Coquille et al., 2014 Nat. Commun., PDB ID: 4PJQ, 4WN4, 4WSL, 4PJR, Non-patent document 7: Shen et al., 2015 Nat. Commun., PDB ID: 519D, 519F, 519G, 519H), they imagined that since those 6th and 9th amino acids in the first motif (N-terminus side) are exposed to the outside, the proteins show aggregation property due to these exposed hydrophobic amino acids (FIG. 1A). On the other hand, they considered that, in the second and following motifs, the 6th and 9th amino acids are buried inside the protein, and form a hydrophobic core, and therefore if hydrophilic residues are placed as the 6th and 9th amino acids of all the motifs, the protein structure may collapse. Therefore, they decided to decrease the aggregation property of PPR by using hydrophilic amino acid (asparagine, aspartic acid, glutamine, glutamic acid, lysine, arginine, serine, and threonine) as the 6th amino acid, preferably the 6th and 9th amino acids, in only the first motif.

Specific procedure is as follows.

In the first PPR motif ($M_1$) from the N-terminus of a protein capable of binding to a target nucleic acid having a specific nucleotide sequence:

(1) a hydrophilic amino acid is used as the $A_6$ amino acid, preferably asparagine or aspartic acid is used as the $A_6$ amino acid, (2) further, a hydrophilic amino acid or glycine, preferably glutamine, glutamic acid, lysine, or glycine, is used as the $A_9$ amino acid, or (3) the $A_6$ amino acid and $A_9$ amino acid are constituted by any of the following combinations;

combination of asparagine as the $A_6$ amino acid and glutamic acid as the $A_9$ amino acid, combination of asparagine as the $A_6$ amino acid and glutamine as the $A_9$ amino acid, combination of asparagine as the $A_6$ amino acid and lysine as the $A_9$ amino acid, and combination of aspartic acid as the $A_6$ amino acid and glycine as the $A_9$ amino acid.

(Novel PPR Motif)

The present invention provides novel PPR motifs with improved aggregation property and novel PPR proteins containing the same, which were found as described above.

The novel PPR motifs provided by the present invention are followings:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, and 34, and having a cytosine-binding property;

(C-3) a PPR motif having a sequence identity of at least 80% to any one of the sequences of SEQ ID NOS: 4 to 7, provided that the amino acids at positions 1, 4, 6, and 34 are identical, and having a cytosine-binding property;

(A-1) a PPR motif consisting of the sequence of SEQ ID NO: 8 having a substitution of the amino acid at position 6 with asparagine or aspartic acid;

(A-2) a PPR motif consisting of the sequence of (A-1) having a substitution, deletion, or addition of 1 to 9 amino acids other than the amino acids at positions 1, 4, 6, and 34, and having an adenine-binding property;

(A-3) a PPR motif having a sequence identity of at least 80% to the sequence of (A-1), provided that the amino acids at positions 1, 4, 6, and 34 are identical, and having an adenine-binding property;

(G-1) a PPR motif consisting of the sequence of SEQ ID NO: 9 having a substitution of the amino acid at position 6 with asparagine or aspartic acid;

(G-2) a PPR motif consisting of the sequence of (G-1) having a substitution, deletion, or addition of 1 to 9 amino acids other than the amino acids at positions 1, 4, 6, and 34, and having a guanine-binding property;

(G-3) a PPR motif having a sequence identity of at least 80% to the sequence of (G-1), provided that the amino acids at positions 1, 4, 6, and 34 are identical, and having a guanine-binding property;

(U-1) a PPR motif consisting of the sequence of SEQ ID NO: 10 having a substitution of the amino acid at position 6 with asparagine or aspartic acid;

(U-2) a PPR motif consisting of the sequence of (U-1) having a substitution, deletion, or addition of 1 to 9 amino acids other than the amino acids at positions 1, 4, 6, and 34, and having a uracil-binding property; and (U-3) a PPR motif having a sequence identity of at least 80% to the sequence of (U-1), provided that the amino acids at positions 1, 4, 6, and 34 are identical, and having a uracil-binding property.

Among such PPR motifs, the followings are particularly preferred:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, 9, and 34, and having a cytosine-binding property;

(C-3) a PPR motif having a sequence identity of at least 80% to any one of the sequences of SEQ ID NOS: 4 to 7, provided that the amino acids at positions 1, 4, 6, 9, and 34 are identical, and having a cytosine-binding property;

(A-1) a PPR motif consisting of the sequence of SEQ ID NO: 8 having such substitutions of the amino acids at positions 6 and 9 that any one of the combinations defined below is satisfied;

(A-2) a PPR motif consisting of the sequence of (A-1) having a substitution, deletion, or addition of 1 to 9 amino acids other than the amino acids at positions 1, 4, 6, 9, and 34, and having an adenine-binding property;

(A-3) a PPR motif having a sequence identity of at least 80% to the sequence of (A-1), provided that the amino acids at positions 1, 4, 6, 9, and 34 are identical, and having an adenine-binding property;

(G-1) a PPR motif consisting of the sequence of SEQ ID NO: 9 having such substitutions of the amino acids at positions 6 and 9 that any one of the combinations defined below is satisfied;

(G-2) a PPR motif consisting of the sequence of (G-1) having a substitution, deletion, or addition of 1 to 9 amino acids other than the amino acids at positions 1, 4, 6, 9, and 34, and having a guanine-binding property;

(G-3) a PPR motif having a sequence identity of at least 80% to the sequence of (G-1), provided that the amino acids at positions 1, 4, 6, 9, and 34 are identical, and having a guanine-binding property;

(U-1) a PPR motif consisting of the sequence of SEQ ID NO: 10 having such substitutions of the amino acids at positions 6 and 9 that any one of the combinations defined below is satisfied;

(U-2) a PPR motif consisting of the sequence of (U-1) having a substitution, deletion, or addition of 1 to 9 amino acids other than the amino acids at positions 1, 4, 6, 9, and 34, and having a uracil-binding property;

(U-3) a PPR motif having a sequence identity of at least 80% to the sequence of (U-1), provided that the amino acids at positions 1, 4, 6, 9, and 34 are identical, and having a uracil-binding property:

a combination of asparagine as the amino acid at position 6 and glutamic acid as the amino acid at position 9, a combination of asparagine as the amino acid at position 6 and glutamine as the amino acid at position 9, a combination of asparagine as the amino acid at position 6 and lysine as the amino acid at position 9, and a combination of aspartic acid as the amino acid at position 6 and glycine as the amino acid at position 9.

The specific sequences of SEQ ID NOS: 4 to 10 are shown in FIGS. 1A and 1B, and in the sequence listing.

Among such PPR motifs, more preferred are the followings:

(C-4) a PPR motif consisting of the sequence of SEQ ID NO: 4;

(A-4) a PPR motif consisting of the sequence of SEQ ID NO: 58;

(G-4) a PPR motif consisting of the sequence of SEQ ID NO: 59; and (U-4) a PPR motif consisting of the sequence of SEQ ID NO: 60.

The sequences of SEQ ID NOS: 58 to 60 are shown below and in the sequence listing.

Sequence of SEQ ID NO: 58:
VTYTTNIDQLCKAGKVDEALELFKEMRSKGVKPNV

Sequence of SEQ ID NO: 59:
VTYTTNIDQLCKAGKVDEALELFDEMKERGIKPDV

Sequence of SEQ ID NO: 60:
VTYNTNIDQLCKAGRLDEAEELLEEMEEKGIKPDV (PPR Protein with Improved Aggregation Property)

The present invention also provides PPR proteins with improved aggregation properties found as described above.

In one of the preferred embodiments, the $A_9$ amino acid of $M_1$ is a non-hydrophobic amino acid or glycine, whatever the other amino acids of $M_1$ are, and whatever the amino acid sequences of the motifs other than $M_1$ are. The non-hydrophobic amino acid is a hydrophilic amino acid, or cysteine or histidine; preferably a hydrophilic amino acid, i.e., arginine, asparagine, aspartic acid, glutamic acid, glutamine, lysine, serine, or threonine; more preferably glutamine, glutamic acid, or lysine.

In one of the preferred embodiments, the $A_9$ amino acid of $M_1$ is glutamine, glutamic acid, lysine, or glycine, whatever the other amino acids of $M_1$ are, and whatever the amino acid sequences of the motifs other than $M_1$ are.

In one of the preferred embodiments, the $A_6$ amino acid of $M_1$ is a non-hydrophobic amino acid, whatever the other amino acids of $M_1$ are, and whatever the amino acid sequences of the motifs other than $M_1$ are. The non-hydrophobic amino acid is, for example, a hydrophilic amino acid, or cysteine or histidine; preferably a hydrophilic amino acid, i.e., arginine, asparagine, aspartic acid, glutamic acid, glutamine, lysine, serine, or threonine; more preferably asparagine, or aspartic acid.

In one of the particularly preferred embodiments, the $A_6$ and $A_9$ amino acids of $M_1$ consist of any of the following combination, whatever the other amino acids of $M_1$ are, and whatever the amino acid sequences of the motifs other than $M_1$ are:

combination of asparagine as the $A_6$ amino acid and glutamic acid as the $A_9$ amino acid, combination of asparagine as the $A_6$ amino acid and glutamine as the $A_9$ amino acid, combination of asparagine as the $A_6$ amino acid and lysine as the $A_9$ amino acid, and combination of aspartic acid as the $A_6$ amino acid and glycine as the $A_9$ amino acid.

In one of the preferred embodiments of the RNA-binding protein, the $A_6$ and $A_9$ amino acids of $M_1$ satisfy the above conditions, and at least one, preferably half or more, more preferably all, of the included PPR motifs satisfy any of the following conditions:

when the base to be bound is cytosine, $A_1$ is valine, $A_4$ is asparagine, and $A_{ii}$ is serine;

when the base to be bound is adenine, $A_1$ is valine, $A_4$ is threonine, and $A_{ii}$ is asparagine;

when the base to be bonded is guanine, $A_1$ is valine, $A_4$ is threonine, and $A_{ii}$ is aspartic acid; and when the base to be bound is uracil or thymine, $A_1$ is valine, $A_4$ is asparagine, and $A_{ii}$ is aspartic acid.

In one of the preferred embodiments of the RNA-binding protein, $M_1$ is the novel PPR motif described above.

In one of the particularly preferred embodiments, $M_1$ is a PPR motif consisting of any of the following polypeptides:

a polypeptide consisting of any one of the sequences of SEQ ID NOS: 4 to 7 for cytosine as the base to be bound;

a polypeptide consisting of the sequence of SEQ ID NO: 8 having such substitutions of the amino acids at positions 6 and 9 that any one of the combinations defined in the following paragraph is satisfied for adenine as the base to be bound;

a polypeptide consisting of the sequence of SEQ ID NO: 9 having such substitutions of the amino acids at positions 6 and 9 that any one of the combinations defined in the following paragraph is satisfied for guanine as the base to be bound; and a polypeptide consisting of the sequence of SEQ ID NO: 10 having such substitutions of the amino acids at positions 6 and 9 that any one of the combinations defined in the following paragraph is satisfied for uracil as the base to be bound;

At least one of the PPR motifs other than M, is a PPR motif consisting of any one of the following polypeptides:

a polypeptide consisting of the sequence of SEQ ID NO: 2 for cytosine as the base to be bound;

a polypeptide consisting of the sequence of SEQ ID NO: 8 for adenine as the base to be bound;

a polypeptide consisting of the sequence of SEQ ID NO: 9 for guanine as the base to be bound; and a polypeptide consisting of the sequence of SEQ ID NO: 10 for uracil as the base to be bound.

The combinations referred to in the above paragraph are any of the followings:

a combination of asparagine as the $A_6$ amino acid and glutamic acid as the $A_9$ amino acid at position 9, a combination of asparagine as the $A_6$ amino acid and glutamine as the $A_9$ amino acid, a combination of asparagine as the $A_6$ amino acid and lysine as the $A_9$ amino acid, and a combination of aspartic acid as the $A_6$ amino acid and glycine as the $A_9$ amino acid.

In one of the particularly preferred embodiments, $M_1$ is a PPR motif consisting of any one of the following polypeptides:

a polypeptide consisting of the sequence of SEQ ID NO: 4 for cytosine as the base to be bound;

a polypeptide consisting of the sequence of SEQ ID NO: 58 for adenine as the base to be bound;

a polypeptide consisting of the sequence of SEQ ID NO: 59 for guanine as the base to be bound; and a polypeptide consisting of the sequence of SEQ ID NO: 60 for uracil as the base to be bound.

At least one of the PPR motifs other than $M_1$ is a PPR motif consisting of any one of the following polypeptides:

a polypeptide consisting of the sequence of SEQ ID NO: 2 for cytosine as the base to be bound;

a polypeptide consisting of the sequence of SEQ ID NO: 8 having a substitution of the amino acid at position 15 with lysine for adenine as the base to be bound;

a polypeptide consisting of the sequence of SEQ ID NO: 9 for guanine as the base to be bound; and a polypeptide consisting of the sequence of SEQ ID NO: 10 for uracil as the base to be bound.

(Use of Skeleton of High Performance PPR Motif)

In one of the preferred embodiments of the present invention, the amino acids in the PPR motifs for cytosine, adenine, guanine, and uracil (or thymine) other than the amino acids at positions 1, 4, 6, 9 and ii can be particular amino acids. Precisely, from the *Arabidopsis thaliana* PPR motif sequences, there were collected the PPR motifs in which the combination of amino acids at positions 1, 4, and ii is VTN as adenine-recognizing PPR motifs, those in which the same is VSN as the cytosine-recognizing PPR motifs, those in which the same is VTD as the guanine-recognizing PPR motifs, and those in which the same is VND as the uracil-recognizing PPR motifs, and types and occurring numbers of the amino acids at every position are summarized. Then, by selecting amino acid highly frequently occurring at each position, the performance of the PPR motif can be enhanced.

For the purpose of using highly frequently occurring amino acids as the amino acids other than the 1st, 4th, 6th, 9th and ii-th amino acids as described above, for obtaining an RNA-binding PPR protein, the amino acid sequences of the following PPR motifs can be referred to:

a PPR motif consisting of any one of the sequences of SEQ ID NOS: 4 to 7 as a PPR motif for cytosine;

a PPR motif consisting of the sequence of SEQ ID NO: 8 as the PPR motif for adenine;

a PPR motif consisting of the sequence of SEQ ID NO: 9 as the PPR motif for guanine; and a PPR motif consisting of the sequence of SEQ ID NO: 10 as the PPR motif for guanine;

Explanation of Technical Terms, Etc

The term "identity" used in the present invention for base sequence (also referred to as nucleotide sequence) or amino acid sequence means percentage of number of matched bases or amino acids shared between two sequences aligned in an optimal manner, unless especially stated. In other words, the identity can be calculated in accordance with the equation: Identity=(Number of matched positions/Total number of positions)×100, and it can be calculated by using commercially available algorithms. Such algorithms are also incorporated in the NBLAST and XBLAST programs described in Altschul et al., J. Mol. Biol., 215 (1990) 403-410. In more detail, the search and analysis for the identity of nucleotide or amino acid sequences can be performed with algorithms or programs well known to those skilled in the art (e.g., BLASTN, BLASTP, BLASTX, and ClustalW). In the case of using a program, parameters can be appropriately set by those skilled in the art, or the default parameters of each program can also be used. The specific procedures of these analysis methods are also well known to those skilled in the art.

In this description, when the expression of having an identity (or identity is high) is used for a nucleotide sequence or amino acid sequence, it means for both cases to have an identity of, at least 70%, preferably 80% or higher, more preferably 85% or higher, still more preferably 90% or higher, further preferably 95% or higher, still further preferably 97.5% or higher, even more preferably 99% or higher, unless especially stated.

As for the term "sequence having a substitution, deletion, or addition" used in the present invention concerning PPR motif or protein, the number of amino acids substituted or the like is not particularly limited in any motif or protein, so long as the motif or protein consisting of the amino acid sequence has the desired function, unless especially stated. The number of amino acids to be substituted, or the like may be about 1 to 9 or 1 to 4, or even larger number of amino acids may be substituted or the like if they are substituted with amino acids having similar properties. The means for preparing polynucleotides or proteins for such amino acid sequences are well known to those skilled in the art.

Amino acids having similar properties refer to amino acids with similar physical properties such as hydropathy, charge, pKa, and solubility, and refer to such amino acid as mentioned below, for example.

Hydrophobic amino acids; alanine, valine, glycine, iso-
leucine, leucine, phenylalanine, proline, tryptophan,
tyrosine.

Non-hydrophobic amino acids; arginine, asparagine,
aspartic acid, glutamic acid, glutamine, lysine, serine,
threonine, cysteine, histidine, methionine.

Hydrophilic amino acids; arginine, asparagine, aspartic
acid, glutamic acid, glutamine, lysine, serine, threo-
nine.

Acidic amino acids: aspartic acid, glutamic acid.

Basic amino acids: lysine, arginine, histidine.

Neutral amino acids: alanine, asparagine, cysteine, gluta-
mine, glycine, isoleucine, leucine, methionine, phenyl-
alanine, proline, serine, threonine, tryptophan, tyrosine,
valine.

Sulfur-containing amino acids: methionine, cysteine.

Aromatic ring-containing amino acids: tyrosine, trypto-
phan, phenylalanine.

The term "preparation" used for genes, nucleic acids,
polynucleotides, proteins, motifs, etc. can be rephrased as
"production" or "manufacturing". In addition, the term
"construction" is sometimes used to refer to preparation of
genes or the like by combining parts, and "construction" can
also be rephrased as "production" or "manufacturing".

The PPR motif, protein containing the same, or nucleic
acids encoding the same of the present invention can be
prepared by those skilled in the art using conventional
techniques, and the explanations in the section of Examples
of this description.

[Characteristics and Use of PPR Proteins]

(Improvement of Aggregation Property of PPR Proteins)

The PPR proteins produced by using the novel PPR
motifs of the present invention show reduced aggregation in
cells. Aggregation of a PPR protein can be evaluated by
those skilled in the art by expressing the PPR protein in cells
and confirming presence or absence of aggregation. The
confirmation is more easily performed by fusing the PPR
protein to a fluorescent protein and expressing them.
According to the examination of the inventors of the present
invention, by appropriately modifying the amino acids in the
1st motif of the PPR protein, the aggregation property of the
PPR protein in the cells is improved, and localization of the
same to the nuclei is improved.

(Binding Power)

PPR proteins prepared by using the novel PPR motifs of
the present invention may have not only reduced intracel-
lular aggregation property, but also RNA binding perfor-
mance equivalent to or higher than those of PPR proteins for
the same target RNA prepared by using existing PPR motifs.
Equivalent means to be 55% or higher, preferably about
75%.

The binding power to a target sequence can be evaluated
by EMSA (Electrophoretic Mobility Shift Assay) or a
method using Biacore. EMSA is a method utilizing a prop-
erty of nucleic acid that when a sample consisting of a
nucleic acid bound with a protein is electrophoresed, the
mobility of the nucleic acid molecule changes from that of
the nucleic acid not bound. Molecular interaction analyzers,
such as Biacore as a typical example, enable kinetic analy-
sis, and therefore allow detailed protein-nucleic acid binding
analysis.

The binding power to a target sequence can also be
evaluated by adding a solution containing a candidate pro-
tein to a solid-phased target nucleic acid, and detecting or
quantifying the protein that bound to the target nucleic acid.
This method is sometimes referred to as the RPB-ELISA
(RNA-protein binding ELISA) method, since it is utilizes ELISA (Enzyme-Linked Immuno Sorbent Assay). The step
of adding a solution containing a candidate protein to a
solid-phased target nucleic acid can be specifically carried
out by flowing a solution containing the objective binding
protein on the target nucleic acid molecule immobilized on
a plate. Immobilization of the target nucleic acid molecule
can be achieved by using various existing immobilization
methods, such as by providing a nucleic acid probe con-
taining a biotin-modified target nucleic acid molecule to a
streptavidin-coated well plate. For detailed conditions of the
experiments, the experiment methods descried in detail in
the section of Examples in this description can be referred
to. In RPB-ELISA, a value obtained by subtracting back-
ground signal (luminescence signal value obtained with an
objective PPR protein without adding the target RNA) from
luminescence obtained with a sample containing the objec-
tive PPR protein and the target RNA thereof can be used as
the binding power of the objective PPR protein and the
target RNA thereof.

[Use of PPR Protein]

(Complex and Fusion Protein)

The PPR motif or PPR protein provided by the present
invention can be made into a complex by binding a func-
tional region. The PPR motif or PPR protein can also be
linked with a proteinaceous functional region to form a
fusion protein. The functional region refers to a part having
such a function as a specific biological function exerted in a
living body or cell, for example, enzymatic function, cata-
lytic function, inhibitory function, promotion function, etc.,
or a function as a marker. Such a region consists of, for
example, a protein, peptide, nucleic acid, physiologically
active substance, or drug. In the following explanations, the
complex of the present invention may be explained with
reference to a fusion protein as an example, but those skilled
in the art may also understand complexes other than fusion
protein according to the explanations.

In one of the preferred embodiments, the functional
region is a ribonuclease (RNase). Examples of RNase are
RNase A (e.g., bovine pancreatic ribonuclease A, PDB
2AAS), and RNase H.

In one of the preferred embodiments, the functional
region is a fluorescent protein. Examples of fluorescent
protein are mCherry, EGFP, GFP, Sirius, EBFP, ECFP,
mTurquoise, TagCFP, AmCyan, mTFP1, MidoriishiCyan,
CFP, TurboGFP, AcGFP, TagGFP, Azami-Green, ZsGreen,
EmGFP, HyPer, TagYFP, EYFP, Venus, YFP, PhiYFP,
PhiYFP-m, TurboYFP, ZsYellow, mBanana, KusabiraOr-
ange, mOrange, TurboRFP, DsRed-Express, DsRed2,
TagRFP, DsRed-Monomer, AsRed2, mStrawberry, Tur-
boFP602, mRFPI, JRed, KillerRed, HcRed, KeimaRed,
mRasberry, mPlum, PS-CFP, Dendra2, Kaede, EosFP, and
KikumcGR. A preferred example is mClover3 in view of
improvement of aggregation and/or efficient localization to
the nuclei as a fusion protein.

In one preferred embodiment, when the target is mRNA,
the functional region is a functional domain that enhances
expression amount of a protein from the target mRNA
(WO2017/209122). The functional domain that enhances
expression amount of a protein from mRNA may be, for
example, all or a functional part of a functional domain of
a protein known to directly or indirectly promote translation
of mRNA. More specifically, it may be a domain that directs
ribosomes to mRNA, domain associated with initiating or
promoting translation of mRNA, domain associated with
transporting mRNA out of the nucleus, domain associated
with binding to the endoplasmic reticulum membrane,
domain containing an endoplasmic reticulum (ER) retention signal sequence, or domain containing an endoplasmic reticulum signal sequence. More specifically, the domain that directs ribosomes to mRNA mentioned above may be a domain comprising all or a functional part of a polypeptide selected from the group consisting of density-regulated protein (DENR), malignant T-cell amplified sequence 1 (MCT-1), transcriptionally-controlled tumor protein (TPT1), and Lerepo4 (zinc finger CCCH-domain). The domain associated with translation initiation or translation promotion of mRNA mentioned above may be a domain comprising all or a functional part of a polypeptide selected from the group consisting of eIF4E and eIF4G. The domain associated with transporting mRNA out of the nucleus mentioned above may be a domain containing all or a functional part of stem-loop binding protein (SLBP). The domain associated with binding to the endoplasmic reticulum membrane mentioned above may be a domain comprising all or a functional part of a polypeptide selected from the group consisting of SEC61B, translocation associated protein alpha (TRAP-alpha), SR-alpha, Dial (cytochrome b5 reductase 3), and p180. The endoplasmic reticulum retention signal (ER retention signal) sequence mentioned above may be a signal sequence comprising the KDEL (SEQ ID NO: 55) or KEEL (SEQ ID NO: 56) sequence. The endoplasmic reticulum signal sequence mentioned above may be a signal sequence including (SEQ ID NO: 57)
MGWSCIILFLVATATGAHS.

In the present invention, the functional region may be fused to the PPR protein on the N-terminal side or the C-terminal side, or on both the N-terminal side and the C-terminal side. The complex or fusion protein may include a plurality of functional regions (e.g., 2 to 5). Further, the complex or fusion protein according to the present invention may consist of the functional region and PPR protein indirectly fused via a linker or the like.

(Nucleic Acid Encoding PPR Protein Etc., Vector, and Cell) The present invention also provides a nucleic acid encoding the PPR motif, PPR protein or fusion protein mentioned above, and a vector containing such a nucleic acid (e.g., vector for amplification, and expression vector). As the host of the vector for amplification, *E. coli* or yeast may be used. In this description, expression vector means a vector containing, for example, a DNA having a promoter sequence, DNA encoding a desired protein, and DNA having a terminator sequence from the upstream side, but they need not necessarily be arranged in this order, so long as the desired function is exerted. In the present invention, recombinant vectors prepared by using various vectors that may be normally used by those skilled in the art may be used.

The PPR protein or fusion protein of the present invention can function in eukaryotic (e.g., animal, plant, microbe (yeast, etc.), and protozoan) cells. The fusion protein of the present invention can function, in particular, in animal cells (in vitro or in vivo). Examples of animal cells into which the PPR protein or fusion protein of the present invention, or a vector expressing it can be introduced include, for example, cells derived from humans, monkeys, pigs, cows, horses, dogs, cats, mice, and rats. Examples of cultured cells into which the PPR protein or fusion protein of the present invention or a vector expressing it can be introduced include, for example, Chinese hamster ovary (CHO) cells, COS-1 cells, COS-7 cells, VERO (ATCC CCL-81) cells, BHK cells, canine kidney-derived MDCK cells, hamster AV-12-

664 cells, HeLa cells, WI38 cells, 293 cells, 293T cells, and PER.C6 cells, but not limited to these.

(Use)
With the PPR protein or fusion protein of the present invention, a functional region may be delivered to the inside of a living body or cells and made to function in a nucleic acid sequence-specific manner. A complex linked with a marker such as GFP may be used to visualize a desired RNA in a living body.

With the PPR protein or fusion protein of the present invention, a nucleic acid can be modified or disrupted in a nucleic acid sequence-specific manner in the inside of cells or living bodies, and a new function may be conferred. In particular, RNA-binding PPR proteins are involved in all the RNA processing steps found in the organelles, such as cleavage, RNA edition, translation, splicing, and RNA stabilization. Accordingly, such uses of the method concerning modification of PPR proteins provided by the present invention, as well as the PPR motif and PPR protein provided by the present invention as mentioned below can be expected in a variety of fields.

(1) Medical Care
Creation of a PPR protein that recognizes and binds to a specific RNA associated with a specific disease. Analysis of a target sequence and associated proteins for a specific RNA. The results of the analysis can be used to identify compounds for the treatment of the disease.

For example, it is known that, in animals, abnormalities in the PPR protein identified as LRPPRC cause Leigh syndrome, French Canadian type (LSFC, Leigh syndrome, subacute necrotizing encephalomyelopathy). The present invention may contribute to the treatment (prevention, therapeutic treatment, or inhibition of progression) of LSFC. Many of the existing PPR proteins work to specify edition sites for RNA manipulation (conversion of genetic information on RNA, often C to U). The PPR proteins of this type have an additional motif that is suggested to interact with RNA editing enzymes on the C-terminal side. PPR proteins having this structure are expected to enable introduction of base polymorphism or treatment of a disease or condition caused by base polymorphism.

Creation of cells with controlled RNA repression/expression. Such cells include stem cells of which differentiation or undifferentiation state is monitored (e.g., iPS cells), model cells for evaluation of cosmetics, and cells in which the expression of functional RNA can be turned on or off for the purpose of elucidating action mechanism and pharmacological testing for drug discovery.

Preparation of a PPR protein that specifically binds to a specific RNA associated with a particular disease. Such a PPR protein is introduced into a cell using a plasmid, virus vector, mRNA, or purified protein, and an RNA function that causes a disease can be changed (improved) by binding of the PPR protein to the target RNA in the cell. Examples of the mechanism of changing the function include, for example, change of the RNA structure by binding, knockdown by decomposition, change of the splicing reaction by splicing, base substitution, and so forth.

(2) Agriculture, Forestry and Fishery
Improvement of yield and quality of crops, forest products and marine products.

Breeding of organisms with improved disease resistance, improved environmental tolerance, or improved or new function.

For example, concerning hybrid first generation (F1) plant crops, an F1 plant may be artificially created by using stabilization of mitochondrial RNA and translation control by PPR proteins so that yield and quality of the crops may be improved. RNA manipulation and genome edition using PPR proteins more accurately and quickly enable variety improvement and breeding (genetic improvement of organisms) of organisms compared with conventional techniques. In addition, it can be said that RNA manipulation and genome editing using PPR proteins are similar to the classical breeding methods such as selection of mutants and backcrossing, since they do not transform traits with a foreign gene as in genetic recombination, but they are techniques using RNA and genomes originally possessed by plants and animals. Therefore, they can also surely and quickly cope with global-scale food and environmental problems.

(3) Chemistry

Control of protein expression amount by manipulating DNA and RNA in the production of useful substances using microorganisms, cultured cells, plant bodies, and animal bodies (e.g., insect bodies). Productivity of useful substances can be thereby improved. Examples of the useful substances are proteinaceous substances such as antibodies, vaccines, and enzymes, as well as relatively low-molecular weight compounds such as pharmaceutical intermediates, fragrances, and dyes.

Improvement of production efficiency of biofuel by modification of metabolic pathways of algae and microorganisms.

EXAMPLES

Example 1: Intracellular Analysis of Fluorescent Protein-Fused PPR Proteins (Design of Motifs)

```
The target sequence was
                                (SEQ ID NO: 1)
CAGCAGCAGCAGCAGCAG
``` including six repeats of CAG sequence. The base recognized by a PPR motif is determined by the 1st, 4th and ii-th amino acids in the sequence. The PPR motif that recognizes cytosine contained 1st is valine, 4th asparagine, and ii-th serine, the PPR motif that recognizes adenine contained 1st is valine, 4th threonine, and ii-th asparagine, and the PPR motif that recognizes guanine contained 1st is valine, 4th threonine, and ii-th aspartic acid, respectively. For the PPR motif that recognizes uracil, 1st valine, 4th asparagine, and ii-th aspartic acid can be used.

Further, as the 6th and 9th amino acids of the 1st motif that recognizes cytosine (Mutated motif in FIG. 1A), there were selected leucine and glycine (C_6L9G, PPRcag_1, SEQ ID NO: 2 mentioned above) as a typical combination, and leucine and glutamic acid (C_6L9E, PPRcag_2, SEQ ID NO: 3), asparagine and glutamine (C_6N9Q, PPRcag_3, SEQ ID NO: 4), asparagine and glutamic acid (C_6N9E, PPRcag_4, SEQ ID NO: 5), asparagine and lysine (C_6N9K, PPRcag_5, SEQ ID NO: 6), and aspartic acid and glycine (C_6D9G, PPRcag_6, SEQ ID NO: 7) were selected as mutant types (FIG. 1B). These PPR motif sequences were arranged so that the encoded proteins bind to the CAGCAGCAGCAGCAGCAG sequence (SEQ ID NO: 1 mentioned above), and PPR genes (SEQ ID NOS: 11 to 16) were prepared. In order to efficiently and accurately ligate the 18 of DNAs encoding the respective PPR motifs, the highly frequently found amino acids were selected as the amino acids other than the 1st, 4th, 6th, 9th, and ii-th amino acids in the PPR motifs for cytosine, adenine, and guanine, respectively, as described above (SEQ ID NOS: 8 and 9, see Patent document 1 mentioned above).

(Preparation of Plasmids)

Plasmids containing each of the PPR genes were constructed by using the Golden Gate method. In more detail, 10 kinds of intermediate vectors Dest-a, b, c, d, e, f, g, h, i, and j, designed to be seamlessly ligated in sequence, were prepared, and 20 kinds of motifs consisting of one motif or two motifs (single PPR motifs corresponding to A, C, G, and U, and double PPR motifs corresponding to AA, AC, AG, AU, CA, CC, CG, CU, GA, GC, GG, GU, UA, UC, UG, and UU) were inserted into 10 kinds of the vectors to produce 200 kinds of parts.

There were prepared

```
                                (SEQ ID NO: 43)
gaagacataaactccgtggtcacATACagagaccaaggtctcaGTGGtcac
atacatgtcttc
as Dest-a, (SEQ ID NO: 44)
gaagacatATACagagaccaaggtctcaGTGGtgacataatgtcttc
as Dest-b, (SEQ ID NO: 45)
gaagacatcATACagagaccaaggtctcaGTGGttacatatgtcttc
as Dest-c, (SEQ ID NO: 46)
gaagacatacATACagagaccaaggtctcaGTGGttacaatgtcttc
as Dest-d, (SEQ ID NO: 47)
gaagacattacATACagagaccaaggtctcaGTGGtgacatgtcttc
as Dest-e, (SEQ ID NO: 48)
gaagacattgacATACagagaccaaggtctcaGTGGttaatgtcttc
as Dest-f, (SEQ ID NO: 49)
gaagacatgttacATACagagaccaaggtctcaGTGGtcatgtcttc
as Dest-g, (SEQ ID NO: 50)
gaagacatggtcacATACagagaccaaggtctcaGTGGtatgtcttc
as Dest-h, (SEQ ID NO: 51)
gaagacattggttacATACagagaccaaggtctcaGTGGatgtcttc
as Dest-i,
and (SEQ ID NO: 52)
gaagacatgtggtgacATACagagaccaaggtctcaGTGGtcttc
as Dest-j
by a gene synthesis technique, and cloned into
pUC57-kan.
```

Dest-a to Dest-j were selected according to the target sequence, and cloned into the vector by the Golden Gate reaction. The vector used here was designed so that the amino acid sequence of MGNSV (SEQ ID NO: 53) was added to the N-terminus of the 18 PPR sequences linked together, and ELTYNTLISGLGKAGRARDPPV (SEQ ID NO: 54) to the C-terminus of the same. It was confirmed that the correct size genes were cloned, and the sequences of the cloned genes were confirmed by sequencing.

(Detection of Expression in Cells)

The expression plasmid pcDNA3.1 for expression in cultured animal cells contains the CMV promoter and SV40 poly-A signal sequence, and a gene to be expressed can be inserted between them. To detect the expression of PPR proteins in cells, PPR proteins fused with a fluorescent protein were expressed, and aggregation and nuclear localization thereof in the cells were analyzed on the basis of fluorescent images thereof. Fused protein genes comprising those for EGFP, nuclear localization signal sequence, PPR protein, and FLAG epitope tag fused together in this order from the N-terminus side were inserted into pcDNA3.1 (SEQ ID NOS: 17 to 22). Protein genes comprising those for mClover3, PPR protein, nuclear localization signal sequence, and FLAG epitope tag fused together in this order from the N-terminus side were also inserted into pcDNA3.1 (SEQ ID NOS: 23 to 28). Plasmids not containing PPR were also prepared as control (SEQ ID NOS: 35 and 36).

The HEK293T cells were inoculated at a density of $1 \times 10^6$ cells in 10 cm dish containing 9 mL of DMEM, and 1 mL of FBS, and cultured in an environment of 37° C. and 5% $CO_2$ for 2 days, and then the cells were collected. The collected cells were inoculated on a PLL-coated 96-well plate at a density of $4 \times 10^4$ cells/well, and cultured in an environment of 37° C. and 5% $CO_2$ for 1 day. A mixture of 200 ng of the plasmid DNA, 0.6 μL of Fugene (registered trademark)-HD (Promega, E2311), and 200 μL of Opti-MEM was prepared, the whole volume thereof was added to each well, and culture was performed in an environment of 37° C. and 5% $CO_2$ for 1 day. After the culture, the medium was removed, each well was washed once with 50 μL of PBS, then 1 μL of Hoechst (1 mg/mL, Dojin Chemical, 346-07951) and 50 μL of PBS were added to each well, the plate was left under an environment of 37° C. and 5% $CO_2$ for 10 minutes, and then each well was washed with 50 μL of PBS. After the washing, 50 μL of PBS was added, and GFP fluorescence and Hoechst fluorescence images of each well were obtained by using a DMi8 fluorescence microscope (Leica).

The results are shown in FIG. 2. Expression in the cells of the PPR proteins fused with EGFP and nuclear localization signal sequence was confirmed, and as a result, it was confirmed that PPRcag_1 (6L9G) and PPRcag_2 (6L9E) did not localize to the nuclei, but strongly aggregated around the nuclei. On the other hand, PPRcag_3 (6N9Q), PPRcag_4 (6N9E), PPRcag_5 (6N9K), and PPRcag_6 (6D9G) did not localize to the nuclei, although their aggregation was week. When mClover3 was fused, it was confirmed that PPRcag_1 (6L9G) and PPRcag_2 (6L9E) localized to the nuclei, but aggregated in the nuclei. In contrast, PPRcag_3 (6N9Q), PPRcag_4 (6N9E), PPRcag_5 (6N9K), and PPRcag_6 (6D9G) localized to the nuclei, and did not aggregate. Therefore, it was found that 6N9E, 6N9Q, 6N9K, and 6D9G mutations are favorable for improving aggregation, and mClover3 is better than EGFP for efficient localization to the nuclei.

Example 2: RNA Binding Analysis of CAG-Binding PPR Proteins

To confirm binding of PPRcag_1, PPRcag_2, PPRcag_3, PPRcag_4, PPRcag_5, and PPRcag_6 to their target RNAs, recombinant proteins were prepared, and binding experiments were performed.

Protein genes were designed for the respective PPR proteins fused with luciferase on the N-terminus side and 6×histidine tag sequence on the C-terminus side, and cloned into an *E. coli* expression plasmid (SEQ ID NOS: 29 to 34). Nluc-Hisx6 protein gene not containing PPR protein was also prepared as a control (SEQ ID NOS: 37).

The *E. coli* Rosetta (DE3) strain was transformed with the completed plasmids. The *E. coli* was cultured in 2 mL of the LB medium containing 100 pg/mL ampicillin at 37° C. for 12 hours. When $OD_{600}$ reached 0.5 to 0.8, the culture medium was transferred to an incubator at 15° C., and left standing for 30 minutes. Then, 100 μL of an JPTG solution was added (IPTG final concentration, 0.1 mM), and the culture was further continued at 15° C. for 16 hours. An *E. coli* pellet was collected by centrifugation at 5,000×g and 4° C. for 10 minutes, 1.5 mL of a lysis buffer (20 mM Tris-HCl, pH 8.0, 150 mM NaCl, 0.5% NP-40, 1 mM $MgCl_2$, 2 mg/mL lysozyme, 1 mM PMSF, 2 μL of DNase) was added to the pellet, and the mixture was frozen at −80° C. for 20 minutes. The cells were cryodisrupted with permeabilization at 25° C. for 30 minutes. The disrupted cell mixture was then centrifuged at 3,700 rpm and 4° C. for 15 minutes, and the supernatant containing soluble PPR protein (*E. coli* lysate) was collected.

The binding experiment for PPR protein and RNA was performed by an experimental method for binding of PPR protein and biotinylated RNA on a streptavidin plate.

There were synthesized RNA probes of 30-base RNAs containing the target CAGx6 sequence, untargeted CGGx6, CUGx6, and CCGx6, and the Dlb (UGGUGUAUCUUGU-CUUUA) sequence (positions 8 to 25 of SEQ ID NO: 42) modified with biotin at the 5'-end (in that order, SEQ ID NOS: 38 to 42, respectively) (Grainer). To a streptavidin-coated plate (Thermo Fisher, Cat. No. 15502), the 5'-end biotinylated RNA probes were added, reaction was allowed at room temperature for 30 minutes, and the plate was washed with a probe washing buffer (20 mM Tris-HCl, pH 7.6, 150 mM NaCl, 5 mM $MgCl_2$, 0.5% NP-40, 1 mM DTT, 0.1% BSA). For background measurement, wells to which biotinylated RNA was not added, but the lysis buffer was added were also prepared. Then, a blocking buffer (20 mM Tris-HCl, pH 7.6, 150 mM NaCl, 5 mM $MgCl_2$, 0.5% NP-40, 1 mM DTF, 1% BSA) was added, and the plate surface was blocked at room temperature for 30 minutes. Then, 100 μL of the *E. coli* lysate containing luciferase-fused PPR protein having a luminescence of $1.5 \times 10^8$ LU/μL was added, and the binding reaction was allowed at room temperature for 30 minutes. Then, the plate was washed 5 times with 200 μL of a washing buffer (20 mM Tris-HCl, pH 7.6, 150 mM NaCl, 5 mM $MgCl_2$, 0.5% NP-40, 1 mM DTT). To each well, 40 μL of luciferase substrate (Promega, E151A) diluted 2,500-fold with the washing buffer was added, reaction was allowed for 5 minutes, and then luminescence was measured with a plate reader (PerkinElmer, Cat. No. 5103-35).

The results are shown in FIG. 3. It was found that all PPRs specifically bind to the target, CAGx6. The binding powers of PPRcag_2, PPRcag_3, PPRcag_4, PPRcag_5, and PPRcag_6 to the target sequence were substantially equivalent, about 80%, about 60%, about 120%, and about 130%, respectively, compared with that of PPRcag_1. These results indicate that the binding performance was not substantially changed by the mutations except for PPRcag_4.

Example 3: Control of Aggregation of PPR Protein

A PPR protein using V2 motif (SEQ ID NO: 61 for nucleotide sequence, and SEQ ID NO: 62 for amino acid sequence) and a PPR protein using v3.2 motif (SEQ ID NO: 63 for nucleotide sequence, and SEQ ID NO: 64 for amino acid sequence) were prepared in an *E. coli* expression system, respectively, purified, and separated by gel filtration chromatography. The v2 motif refers to the PPR motifs having the sequence of SEQ ID NO: 2, and SEQ ID NOS: 8 to 10, and the v3.2 motif refers to the PPR motifs having the sequence of SEQ ID NO: 4 and SEQ ID NOS: 58 to 60 in the case of the first motif from the N-terminus side, or in the other cases, the PPR motif for adenine comprising the sequence of SEQ ID NO: 8 having a substitution of 15th aspartic acid with lysine, or the PPR motifs for bases other than adenine comprising a sequence selected from SEQ ID NOS: 2, 9, and 10.

(Expression and Purification of Proteins)

The *E. coli* Rosetta strain was transformed with pE-SUMOpro Kan plasmid containing a DNA sequence encoding the objective PPR protein, and cultured at 37° C., then the temperature was lowered to 20° C. when $OD_{600}$ reached 0.6, and IPTG was added at a final concentration of 0.5 mM so that the objective PPR was expressed in the *E. coli* cells as SUMO-fused protein. The cells were cultured overnight, then collected by centrifugation, and resuspended in a lysis buffer (50 mM Tris-HCl, pH 8.0, 500 mM NaCl). The *E. coli* cells were disrupted by sonication, and centrifuged at 17,000 g for 30 minutes, then the supernatant fraction was applied to an Ni-Agarose column, the column was washed with the lysis buffer containing 20 mM imidazole, and then the SUMO-fused objective PPR protein was eluted with the lysis buffer containing 400 mM imidazole. After the elution, the SUMO protein was cleaved from the objective PPR protein with Ulp1, and at the same time, the protein solution was substituted with an ion-exchange buffer (50 mM Tris-HCl, pH 8.0, 200 mM NaCl) by dialysis. Subsequently, cation exchange chromatography was performed by using SP column. After application to the column, proteins were eluted with gradually increasing NaCl concentration of from 200 mM to 1 M. The fraction containing the objective PPR protein was subjected to final purification by gel filtration chromatography using Superdex 200 column. The objective PPR protein eluted from the ion exchange column was applied to the gel filtration column equilibrated with a gel filtration buffer (25 mM HEPES, pH 7.5, 200 mM NaCl, 0.5 mM tris(2-carboxyethyl)phosphine (TCEP)). Finally, the fraction containing the objective PPR protein was concentrated, frozen in liquid nitrogen, and stored at −80° C. until used for the next analysis.

(Gel Filtration Chromatography)

The purified recombinant PPR protein was prepared at a concentration of 1 mg/ml. For gel filtration chromatography, Superdex 200 increase 10/300 GL (GE Healthcare) was used. To the gel filtration column equilibrated with 25 mM HEPES pH7.5, 200 mM NaCl, 0.5 mM tris(2-carboxyethyl)phosphine (TCEP), the prepared protein was applied, and the absorbance of the solution eluted from the gel filtration column was measured at 280 nm to analyze the properties of the protein.

(Results)

The results are shown in FIG. 4. The smaller volume of the elution fraction (Elution vol.) means a larger molecular size. The proteins using v2 were eluted in 8 to 10 mL of elution fractions, whereas the peaks of the proteins using v3.2 were observed in elution fractions of 12 to 14 mL. This result suggested possibility that the proteins using v2 aggregated due to the larger protein size thereof, and the aggregation was improved in the proteins using v3.2.

The invention claimed is:

1. A PPR motif, which is any one of the following PPR motifs:

(C-1) a PPR motif consisting of any one of the sequences of SEQ ID NOS: 4 to 7;

(C-2) a PPR motif consisting of any one of the sequences of SEQ ID NOS: 4 to 7 having a substitution, deletion, or addition of 1 to 9 amino acids other than the amino acids at positions 1, 4, 6, and 34;

(C-3) a PPR motif having a sequence identity of at least 80% to any one of the sequences of SEQ ID NOS: 4 to 7, provided that the amino acids at positions 1, 4, 6, and 34 are identical;

(A-1) a PPR motif consisting of the sequence of SEQ ID NO: 8 having a substitution of the amino acid at position 6 with asparagine or aspartic acid:

(A-2) a PPR motif consisting of the sequence of (A-1) having a substitution, deletion, or addition of 1 to 9 amino acids other than the amino acids at positions 1, 4, 6, and 34;

(A-3) a PPR motif having a sequence identity of at least 80% to the sequence of (A-1), provided that the amino acids at positions 1, 4, 6, and 34 are identical;

(G-1) a PPR motif consisting of the sequence of SEQ ID NO: 9 having a substitution of the amino acid at position 6 with asparagine or aspartic acid;

(G-2) a PPR motif consisting of the sequence of (G-1) having a substitution, deletion, or addition of 1 to 9 amino acids other than the amino acids at positions 1, 4, 6, and 34;

the amino acids at positions 1, 4, 6, and 34 are identical;

(G-3) a PPR motif having a sequence identity of at least 80% to the sequence of (G-1), provided that the amino acids at positions 1, 4, 6, and 34 are identical:

(U-1) a PPR motif consisting of the sequence of SEQ ID NO: 10 having a substitution of the amino acid at position 6 with asparagine or aspartic acid: (U-2) a PPR motif consisting of the sequence of (U-1) having a substitution, deletion, or addition of 1 to 9 amino acids other than the amino acids at positions 1, 4, 6, and 34; and (U-3) a PPR motif having a sequence identity of at least 80% to the sequence of (U-1), provided that the amino acids at positions 1, 4, 6, and 34 are identical.

2. A PPR motif, which is any one of the following PPR motifs:

(G-1) a PPR motif consisting of the sequence of SEQ ID NO: 9 having such substitutions of the amino acids at positions 6 and 9 that any one of the combinations defined below is satisfied;

(U-1) a PPR motif consisting of the sequence of SEQ ID NO: 10 having such substitutions of the amino acids at positions 6 and 9 that any one of the combinations defined below is satisfied;

wherein the conditions for SEQ ID NO: 8-10 are selected from a combination of asparagine as the amino acid at position 6 and glutamic acid as the amino acid at position 9, a combination of asparagine as the amino acid at position 6 and glutamine as the amino acid at position 9, a combination of asparagine as the amino acid at position 6 and lysine as the amino acid at position 9, and a combination of aspartic acid as the amino acid at position 6 and glycine as the amino acid at position 9.

3. The PPR motif according to claim 1, which is any one of the following PPR motifs:

(C-4) a PPR motif consisting of the sequence of SEQ ID NO: 4;

(A-4) a PPR motif consisting of the sequence of SEQ ID NO: 58;

(G-4) a PPR motif consisting of the sequence of SEQ ID NO: 59; and (U-4) a PPR motif consisting of the sequence of SEQ ID NO: 60.

4. A method of reducing aggregation of a PPR protein comprising inserting a motif according to claim 2 or 3 at the N-terminus of the PPR protein.

5. A fusion protein comprising: at least one selected from the group consisting of a fluorescent protein, a nuclear localization signal peptide, and a tag protein; and a PPR protein containing the PPR motif according to claim 1.

6. A method for detecting a nucleic acid, which comprises a step of adding a solution containing a PPR motif according to claim 2 or 3 at the N-terminus of the protein to a solid-phased target nucleic acid, and detecting or quantifying the protein that bound to the target nucleic acid.

* * * * *

188